(12) United States Patent
Weiss

(10) Patent No.: US 7,229,788 B1
(45) Date of Patent: Jun. 12, 2007

(54) PROTEASE SUSCEPTIBILITY II

(75) Inventor: Anthony Steven Weiss, New South Wales (AU)

(73) Assignee: The University of Sydney, Sydney (AU)

( * ) Notice: Subject to any disclaimer, the term of this patent is extended or adjusted under 35 U.S.C. 154(b) by 0 days.

(21) Appl. No.: 09/743,818

(22) PCT Filed: Jul. 19, 1999

(86) PCT No.: PCT/AU99/00580

§ 371 (c)(1),
(2), (4) Date: Apr. 26, 2001

(87) PCT Pub. No.: WO00/04043

PCT Pub. Date: Jan. 27, 2000

(30) Foreign Application Priority Data

Jul. 17, 1998 (AU) .................................. PP4723

(51) Int. Cl.
C12N 15/00 (2006.01)
C07K 1/00 (2006.01)
C07K 14/00 (2006.01)

(52) U.S. Cl. ...................... 435/69.1; 435/183; 530/350
(58) Field of Classification Search ................ 530/350; 435/69.1, 183
See application file for complete search history.

(56) References Cited

U.S. PATENT DOCUMENTS

| 5,726,040 | A | 3/1998 | Ensley |
| 5,969,106 | A | 10/1999 | Rothstein et al. |
| 6,232,458 | B1 | 5/2001 | Weiss .......................... 536/235 |
| 6,451,326 | B2 | 9/2002 | Ensley |

FOREIGN PATENT DOCUMENTS

| AU | 83252/98 B2 | 2/1999 |
| WO | WO94/14958 A1 | 7/1994 |
| WO | WO99/03886 A2 | 1/1999 |

OTHER PUBLICATIONS

Voet & Voet, Biochemsitry, N.Y. John Wiley & Sons, 1990, p. 116.*
Tassabehji Mayada et al, An Elastin Gene Mutation Producing Abnormal Tropoelastin and abnormal Eleastic Fibres in a Patient with Autosomal Dominant Cutis Laxa, Human Molecular Genetics, vol. 7, No. 6, pp. 1021-1028, (Jun. 1998).
Sechler Jan et al, Elastin Gene Mutations in Transgenic Mice, CIBA Foundation Symposium; The Molecular Biology and Pathology of Elastic Tissues; John Wiley and Sons Ltd., Baffin Lane, Chicester PO 19 IUD, England; John Wiley and Sons, Inc., 605 Third Avenue, New York, New York 10158-0012, USA series: CIBA Found, (1995) pp. 148-165.
Boyd et al, Mammalian Tropoelastin Multiple Domains of the Protein Define An Evolutionarily Divergent Amino Acid Sequence, Matrix, vol. 11, No. 4, pp. 235-241, (Aug. 1991).

(7) Page Supplementary Partial European Search Report dated Aug. 26, 2004.
Richard Pierce et al, "Elements of the Rat Tropoelastin Gene Associated with Alternative Splicing", Genomics, 12:651-658 (1992).
Faustino Bisaccia et al, "The Amino Acid Sequence Coded by the Rarely Expressed Exon 26a of Human Elastin contains a Stable β-Turn with Chemotactic Activity for Monocytes", Biochemistry, 37(31):11128-11135 (1998).
Jui-Yoa Chang, "Thrombin Specificity—Requirement for Apolar Amino acids Adjacent to the Thrombin Cleavage Site of Polypeptide Substrate", Eur. J. Biochem., 151:217-224 (1985).
Leonard Grosso et al, "PGAIPG, a Repeated Hexapeptide of Bovine and Human Tropoelastin, is Chemotactic for Neutrophils and Lewis Lung Carcinoma Cells", Archives of Biochemistry and Biophysics, 305(2):401-404 (Sep. 1993).
Carl Franzglau et al, "Role of Tropoelastin Fragmentation in Elastogenesis in Rat Smooth Muscle Cells", J. Biol. Chem., 264(25):15115-15119 (Sep. 5, 1989).
Akinobu Hayashi et al, "Presence of Elastin-related 45-kDa Fragment in Culture Medium: Specific Cleavage Product of Tropoelastin in Vascular Smooth Muscle Cell Culture", Biochimicsa et biophysica Acta, 1244:325-330 (1995).
Jun Kobayashi et al, "Serum-Induced Vascular Smooth Muscle Cell Elastolytic activity Through Tyrosine Kinase Intracellular Signalling", Journal of Cellular Physiology, 160:121-131 (1994).
Robert Mecham et al, "Intrinsic Enzyme Activity Associated with Tropoelastin", Biochim. Biophys. Acta., 446:245-254 (1976).
Robert Mecham et al, "Trypsin-like Neutral Protease Associated with Soluble Elastin", Biochemistry, 16(17):3825-3831 (1977).
Robert Mecham et al, "Proteolysis of Tropoelastin", Adv. Expt. Med. Biol., 79:209-216 (1977).
Celeste Rich et al, "Isolation of Tropoelastin a from Lathyritic Chick Aortae", Biochem. J., 271:581-584 (1984).
Nadia Romero et al, "Role of Plasma and Serum Proteases in the Degradation of Elastin", Arch. Biochem. Biophys., 244:161-168 (Jan. 1986).
Robert Rucker, "Isolation of Soluble Elastin from Copper-Deficient Chick Aorta", Methods in Enzymology, 82:650-657 (1982).
L. Sandberg et al, "Production and Isolation of Soluble Elastin from Copper-Deficient Swine", Methods in Enzymology, 82:657-665 (1982).
A. Torres et al, "Isolation and Amino Acid Sequence of Some Thrombin Produced Porcine Tropoelastin Peptides", Adv. Expt. Med. Biol., 79:267-276 (1977).

(Continued)

*Primary Examiner*—Nashaat T. Hashed
*Assistant Examiner*—Holly Schnizer
(74) *Attorney, Agent, or Firm*—Howson & Howson LLP

(57) ABSTRACT

The present invention relates to: manipulation of the amino acid sequence of tropoelastin, particularly human tropoelastin, to modify its protease susceptibility; to tropoelastin derivatives having modified protease susceptibility; to peptidomimetic molecules which contain amino acid sequences which correspond to or incorporate the protease susceptible sequences of tropoelastin; and to uses of the tropoelastin derivatives and peptidomimetic molecules.

The invention also relates to nucleic acid molecules and genetic constructs encoding the amino acid sequences of the derivatives and peptidomimetic molecules of the invention.

23 Claims, 26 Drawing Sheets

OTHER PUBLICATIONS

Stephen McGowan et al, "Serine Proteinase Inhibitors Influence the Stability of Tropoelastin mRNA in Neonatal Rat Lung Fibroblast Cultures", Am. J. Physiol., 270::376-L385 (1996).
Aleksander Hinek et al, "67-kD Elastin-Binding Protein is a Protective "Companion" of Extracellular Insoluble Elastin and Intracellular Tropoelastin", J. Cell Biol., 126(2):563-574 (Jul. 1994).
Jeffrey Davidson et al, "Regulation of Elastin Synthesis in Organ and Cell Culture", Methods in Enzymology, 144:214-232 (1987).
Robert Mecham et al, "Elastin Binds to a Multifunctional 67-Kilodalton Peripheral Membrane Protein", Biochemistry, 28:3716-3722 (1989).
Judith Foster et al, "The Regulation of Lung Elastin Synthesis", Am. J. Physio., 259:L13-L23 (1990).
Amanda Ewart et al, "Hemizygosity at the Elastin Locus in a Developmental Disorder, Williams Syndrome", Nature Genetics, 5:11-16 (Sep. 1993).
J. Tarlton et al, "Postsurgical Wound Progression Monitored by Temporal Changes in the Expression of Matrix Metalloproteinase-9", British Journal of Dermatology, 137:506-516 (1997).
Zena Indik et al, "Structure of the 3'Region of the Human Elastin Gene: Great Abundance of ALU Repetitive Sequences and Few Coding Sequences", Connective Tissue Research, 16:197-211 (1987).
J. Michael Frangiskakis et al, "LIM-kinase 1 Hemizygosity Implicated in Impaired Visuospatial Constructive Cognition", Cell, 86:59-69 (Jul. 12, 1996).
Michael Fazio et al, "Isolation and Characterization of Human Elastin cDNAs, and Age-Associated Variation in Elastin Gene Expression in Cultured Skin Fibroblasts", Laboratory Investigation, 58(3):270-277 (1988).
Lucy Osborne et al, "Identification of Genes from a 500-kb Region at 7q11.23 That is Commonly Deleted in Williams Syndrome Patients", Genomics, 36:328-336 (1996).
Muhammad Bashir et al, "Characterization of the Complete Human Elastin Gene", J. Biol. Chem., 264(16):8887-8891 (May 25, 1989).
James Slack et al, "An Upstream Regulatory Region mediates High-Level, Tissue-Specific Expression of the Human α1(I) Collagen Gene in Transgenic Mice", Molecular and Cellular Biology, 11(4):2066-2074 (Apr. 1991).
Juhani Janne et al, "Transgenic Animals as Bioproducers of Therapeutic Proteins", Annals of Medicine, 24:273-280 (1992).
R. Merrifield, "Solid Phase Peptide Synthesis. I. The Synthesis of a Tetrapeptide", J. Am. Chem. Soc., 85:2149-2154 (Jul. 20, 1963).
Reinhard Knorr et al, "New Coupling Reagents in Peptide Chemistry", Tetrahedron Letters, 30(15):1927-1930 (1989).
Joel Rosenbloom et al, "Regulation of Elastin Gene Expression", Ann. New York Acad. Sci., 624:116-136 (1990).
Joel Rosenbloom et al, "Structure of the Elastin Gene", Ciba Found. Symp., 192:59-80 (1995).
William Parks et al, "Tropoelastin Heterogeneity: Implications for Protein Function and Disease", Am. J. Respir. Cell Mol. Biol., 2:399-406 (1990).
Joseph Cappello et al, "Genetic Engineering of Structural Protein Polymers", Biotechnol. Prog., 6:198-202 (1990).
Veli-Matti Kahari et al, "Deletion Analyses of 5'-Flanking Region of the Human Elastin Gene", J. Biol. Chem., 265(16):9485-9490 (Jun. 1990).
William Parks et al, "Cellular Expresson of Tropoelastin mRNA Splice Variants", Matrix, 12:156-162 (1992).
Joel Rosenbloom et al, "Elastin Genes and Regulation of their Expression", in Critical Review in Eukaryotic Gene Expression, CRC Press Inc., 1(3):145-156 (1991).
David McPherson et al, "Production and Purification of a Recombinant Elastomeric Polypeptide, G-(VPGVG)$_{19}$-VPGV, from Escherichia coli", Biotechnol. Prog., 8:347-352 (1992).
Mayada Tassabehji et al, "Elastin: Genomic Structure and Point Mutations in Patients with Supravavular Aortic Stenosis", Human Molecular Genetics, 6(7):1029-1036 (1997).
Martin Holzenberger et al, "Quantitation of Tropoelastin mRNA and Assessment of Alternative Splicing in Human Skin Fibroblasts by Reverse Transcriptase-Polymerase Chain Reaction", PCR Methods and Applications, 3:107-114 (1993).
Stephen Martin et al, "Total Synthesis and Expression in Escherichia coli of a Gene Encoding Human Tropoelastin", Gene, 154:159-166 (1995).
Zena Indik et al, "Alternative Splicing of Human Elastin mRNA Indicated by Sequence Analysis of Cloned Genomic and Complementary DNA", Proc. Natl. Acad. Sci. USA, 84:5680-5684 (Aug. 1987).
Zena Indik et al, "Production of Recombinant Human Tropoelastin:Characterization and Demonstration of Immunologic and Chemotactic Activity", Archives of Biochemistry and Biophysics, 280(1):80-86 (Jul. 1990).
Louise Oliver et al, "The Gene Coding for Tropoelastin is Represented as a Single Copy Sequence in the Haploid Sheep Genome", Collagen Rel. Res., 7:77-89 (1987).
J. Sambrook et al, Molecular Cloning: a Labortory Manual, 2$^{nd}$ ed., Cold Spring Harbor Laboratory Press, Cold Spring Harbor, NY (1989).
Giorgio Bressan et al, "Repeating Structure of Chick Tropoelastin Revealed by Complementary DNA Cloning", Biochemistry, 26(6):1497-1503 (Mar. 1987).
Kaliannan Raju et al, "Primary Structures of Bovine Elastin a, b, and c Deduced from the Sequences of cDNA Clones", J. Biol. Chem., 262:5755-5762 (1987).
David Lipman et al, "Rapid and Sensitive Protein Similarity Searches", Science, 227:1435-1441 (Mar. 1985).
Debra Bedell-Hogan et al, "Oxidation, Cross-Linking, and Insolubilization of Recombinant Tropoelastin by Purified Lysyl Oxidase", J. Biol. Chem., 268(14):10345-10350 (May 1993).
F. William Studier et al, "Use of T7 RNA Polymerase to Direct Expression of Cloned Genes", Methods Enzymol., 185:60-89 (1990).
Jill Gough et al, "Sequence Diversity Among Related Genes for Recognition of Specific Targets in DNA Molecules", J. Mol. Biol., 166:1-19 (1983).
W. Bullock et al, "XL1-Blue: A High Efficiency Plasmid Transforming recA Escherichia coli Strain with Beta-Galactosidase Selection", BioTechniques, 5(4):376-378 (1987).
Ruth Heim et al, "Alternative Splicing of Rat Tropoelastin mRNA is Tissue-Specific and Developmentally Regulated", Matrix, 11:359-366 (1991).
Helena Yeh et al, "Sequence Variation of Bovine Elastin mRNA due to Alternative Splicing", Collagen Rel. Res., 7:235-247 (1987).
Donald Smith et al, "Single-Step Purification of Polypeptides Expressed in Escherichia coli as Fusions with Glutathione S-transferase", Gene, 67:31-40 (1988).
Michael Fazio et al, "Cloning of Full-length Elastin cDNAs from a Human Skin Fibroblast Recombinant cDNA Library: Further Elucidation of Alternative Splicing Utilizing Exon-specific Oligonucleotides", J. Invest. Dermatol., 91:458-464 (1988).
Dan Urry et al, "Temperature Dependence of Length of elastin and its Polypentapeptide", Biochemical and Biophysical Research Communications, 141(2):749-755 (Dec. 1986).
Rao Rapaka et al, "Synthesis of Polypeptide Models of Elastin, Synthesis and Properties of a Cross-linked polytetrapeptide", Int. J. Peptide Protein Res., 21:352-363 (1983).
L. Sandberg et al, "Tropoelastin Purification from Copper-Deficient Swine: a Simplified Method", Biochim. Biophys. Acta., 236:542-545 (1971).
Elizabeth Murray et al, "Codon Usage in Plant Genes", Nucl. Acids Res., 17(2):477-498 (1989).
Shiping Zhang et al, "Low-Usage Codons in Escherichia coli, yeast, fruit fly and primates", Gene, 105:61-72 (1991).
David Eyre et al, "Cross-Linking in Collagen and Elastin", Ann. Rev. Biochem., 53:717-748 (1984).
Karen Reiser et al, "Enzymatic and Nonenzymatic Cross-Linking of Collagen and Elastin", FASEB J., 6:2439-2449 (1992).
Paul Sharp et al, "Potential Applications", Nucl. Acids Res., 15:1281-1295 (1987).
Shigeyuki Yoshifuji et al, "Chemical Conversion of L-α,ω-Diamino Acids to L-ω-Carbamoyl-α-amino Acids by Ruthenium Tetroxide Oxidation", Chem. Pharm. Bull., 35:2994-3000 (1987).

Imai et al, Expression of Membrane-Type 1 Matrix Metalloproteinase and Activation of Progelatinase A in Human Osterarthritic Cartilage, American Journal of Pathology, vol. 151, No. 1, (Jul. 1997).

D'Ortho et al, Membrane-Type Matrix Metalloproteinases 1 and 2 Exhibit Broad-Spectrum Proteolytic Capacities Comparable to Many Matrix Metalloproteinases, Eur. J. Biochem. 250, pp. 751-757 (Sep. 1997).

Bini et al, Degradation of Cross-Linked Fibrin by Matrix Metalloproteinase 3 (Strolmelysin 1): Hydrolysis of the γ Gly 404-Ala 405 Peptide Bond, Biochemistry, vol. 35, No. 40, pp. 13056-13063 (1996).

Shipley et al, The Structural Basis for the Elastolytic Activity of the 92-kDa and 72-kDa Gelatinases, vol. 271, No. 8, pp. 4335-4341, (Feb. 1996).

Mecham et al, Elastin Degradation by Matrix Metalloproteinases, vol. 272, No. 29 pp. 18071-18076, (Jul. 1997).

Chandler et al, Macrophage Metalloelastase Degrades Matrix and Myelin Proteins and Processes a Tumour Necrosis Factor-α Fusion Protein, Biochemical and Biophysical Research Communications, 228, pp. 421-429 (1996).

Xia et al, Comparison of Cleavage Site Specificity of Gelatinases A and B Using Collagenous Peptides, Biochimica et Biophysica Acta 1293, pp. 259-266, (1996).

Young et al, Characterization of Gelatinases Linked to Extracellular Matrix Invasion in Ovarian Adenocarcinoma: Purification of Matrix Metalloproteinase 2, Article No. 0195, Gynecologic Oncology, 62, 89-99, (1996).

Bellón et al, Study of Biochemical Substrate and Role of Metalloproteinases in Fascia Transversalis from Hernial Process, European Journal of Clinical Investigation, vol. 27(6), pp. 510-516, (Jun. 1997).

Marigo et al, Mapping of Binding Sites for Monoclonal Antibodies to Chick Tropoelastin by Recombinant DNA Techniques, Connective Tissue Research, vol. 28, pp. 13-28 (1992).

Uitto et al, Molecular Biology and Pathology of Human Elastin, Biochemical Society Transactions, 19(4):824-9, (Nov. 1991).

Grosso et al, Fibrolblast Adhesion to Recombinant Tropoelastin Expressed as a Protein A-Fusion Protein, Biochem. J. 273, pp. 517-522, (1991).

Foster et al, Elastin Gene Expression, International Review of Connective Tissue Research, 10:65-95, (1983).

European Communication Pursuant to Article 96(2) EPC dated Nov. 18, 2005, pp. 3.

Canadian Examination Report dated Sep. 30, 2005, pp. 5.

Wu et al, Glycosaminoglycans Mediate the Coacervaton of Human Tropoelastin Through Dominant Charge Interactions Involving Lysine Side Chains, vol. 274, No. 81, pp. 21719-21724, (Jul. 30, 1999).

Kenyon et al, A Novel Human cDNA with a Predicted Protein Similar to Lysyl Oxidase Maps to Chromosome 15q24-q25, The Journal of Biological Chemistry, vol. 268, No. 26, pp. 18435-18437, (Sep. 5, 1993).

Kim et al, A New Gene with Sequence and Structural Similarity to the Gene Encoding Human Lysyl Oxidase, The Journal of Biological Chemistry, vol. 270, No. 13, pp. 7176-7182, (Mar. 31, 1995).

Hernan et al, Human Hemoglobin Expression on *Escherichia coli*: Imporatnce of Optimal Codon Usage, Biochemistry, 31, pp. 8619-8628, (Sep. 15, 1992).

Sharp et al, The Codon Adaptation Index-A Measure of Directional Synonymous Codon Usage Bias, and its Potential Applications, vol. 15, No. 3 (Nov. 2, 1987).

Hamalainen et al, Structure of teh Human Lysyl Oxidase Gene, Genomics 17, pp. 544-548 (Sep. 1993).

11 page -Communication pursuant to Article 96(2) EPC Search Report from European Patent Office for Appl. No. 99 930 951.1-2404.

Stryer, Biochemistry, 2d ed., W. H. Freeman and Co, San Francisco, 1981, pp. 14-15.

\* cited by examiner

```
  1  GATCCATGGGTGGCGTTCCGGGTGCTATCCCGGGTGGCGTTCCGGGTGGTGTATTCTACC   60
     GTACCCACCGCAAGGCCCACGATAGGGCCCACCGCAAGGCCCACCACATAAGATGG

S   M   G   G   V   P   G   A   I   P   G   G   V   P   G   G   V   F   Y   P
                ↑
                Start pf mature processed protein 61  CAGGCGCGGGTCTGGGTGCACTGGGCGGTGGTGCGCTGGGCCCGGGTGGTAAACCGCTGA  120
     GTCCGCGCCCAGACCCACGTGACCCGCCACCACGCGACCCGGGCCCACCATTTGGCGACT

G   A   G   L   G   A   L   G   G   A   L   G   P   G   G   K   P   L   K

121  AACCGGTTCCAGGCGGTCTGGCAGGTGCTGGTCTGGGTGCAGGTCTGGGCGCGTTCCGG   180
     TTGGCCAAGGTCCGCCAGACCGTCCACGACCAGACCCACGTCCAGACCCGCGCAAGGGCC

P   V   P   G   G   L   A   G   A   G   L   G   A   G   L   G   A   F   P   A

181  CGGTTACCTTCCCGGGTGCTCTGGTTCCGGGTGGCGTTGCAGACGCAGCTGCTGCGTACA  240
     GCCAATGGAAGGGCCCACGAGACCAAGGCCCACCGCAACGTCTGCGTCGACGACGCATGT

V   T   F   P   G   A   L   V   P   G   G   V   A   D   A   A   A   A   Y   K

241  AAGCGGCAAAGGCAGGTGCGGGTCTGGGCGGGGTACCAGGTGTTGGCGGTCTGGGTGTAT  300
     TTCGCCGTTTCCGTCCACGCCCAGACCCGCCCCATGGTCCACAACCGCCAGACCCACATA

A   A   K   A   G   A   G   L   G   G   V   P   G   V   G   G   L   G   V   S

301  CTGCTGGCGCAGTTGTTCCGCAGCCGGGTGCAGGTGTAAAACCGGGCAAAGTTCCAGGTG  360
     GACGACCGCGTCAACAAGGCGTCGGCCCACGTCCACATTTTGGCCCGTTTCAAGGTCCAC

A   G   A   V   V   P   Q   P   G   A   G   V   K   P   G   K   V   P   G   V

361  TTGGTCTGCCGGGCGTATACCCGGGTGGTGTTCTGCCGGGCGCGCGTTTCCCAGGTGTTG  420
     AACCAGACGGCCCGCATATGGGCCCACCACAAGACGGCCCGCGCGCAAAGGGTCCACAAC

```
421  GTGTACTGCCGGGCGTTCCGACCGGTGCAGGTGTTAAACCGAAGGCACCAGGTGTAGGCG  480
     CACATGACGGCCCGCAAGGCTGGCCACGTCCACAATTTGGCTTCCGTGGTCCACATCCGC
      V  L  P  G  V  P  T  G  A  G  V  K  P  K  A  P  G  V  G  G
                                                  ─  ─  ─  ─  ─  ─

481  GCGCGTTCGCGGGTATCCCGGGTGTTGGCCCGTTCGGTGGTCCGCAGCCAGGCGTTCCGC  540
     CGCGCAAGCGCCCATAGGGCCCACAACCGGGCAAGCCACCAGGCGTCGGTCCGCAAGGCG
      A  F  A  G  I  P  G  V  G  P  F  G  G  P  Q  P  G  V  P  L
      ─  ─

541  TGGGTTACCCGATCAAAGCGCCGAAGCTTCCAGGTGGCTACGGTCTGCCGTACACCACCG  600
     ACCCAATGGGCTAGTTTCGCGGCTTCGAAGGTCCACCGATGCCAGACGGCATGTGGTGGC
      G  Y  P  I  K  A  P  K  L  P  G  G  Y  G  L  P  Y  T  T  G

601  GTAAACTGCCGTACGGCTACGGTCCGGGTGGCGTAGCAGGTGCTGCGGGTAAAGCAGGCT  660
     CATTTGACGGCATGCCGATGCCAGGCCCACCGCATCGTCCACGACGCCCATTTCGTCCGA
      K  L  P  Y  G  Y  G  P  G  G  V  A  G  A  A  G  K  A  G  Y

661  ACCCAACCGGTACTGGTGTTGGTCCGCAGGCTGCTGCGGCAGCTGCGGCGAAGGCAGCAG  720
     TGGGTTGGCCATGACCACAACCAGGCGTCCGACGACGCCGTCGACGCCGCTTCCGTCGTC
      P  T  G  T  G  V  G  P  Q  A  A  A  A  A  A  K  A  A  A

721  CAAAATTCGGCGCGGGTGCAGCGGGTGTTCTGCCGGGCGTAGGTGGTGCTGGCGTTCCGG  780
     GTTTTAAGCCGCGCCCACGTCGCCCACAAGACGGCCCGCATCCACCACGACCGCAAGGCC
      K  F  G  A  G  A  A  G  V  L  P  G  V  G  G  A  G  V  P  G

781  GTGTTCCAGGTGCGATCCCGGGCATCGGTGGTATCGCAGGCGTAGGTACTCCGGCGGCCG  840
     CACAAGGTCCACGCTAGGGCCCGTAGCCACCATAGCGTCCGCATCCATGAGGCCGCCGGC
      V  P  G  A  I  P  G  I  G  G  I  A  G  V  G  T  P  A  A  A

841  CTGCGGCTGCGGCAGCTGCGGCGAAAGCAGCTAAATACGGTGCGGCAGCAGGCCTGGTTC  900
     GACGCCGACGCCGTCGACGCCGCTTTCGTCGATTTATGCCACGCCGTCGTCCGGACCAAG
      A  A  A  A  A  A  A  K  A  A  K  Y  G  A  A  A  G  L  V  P
```

Figure 2(b)

```
 901  CGGGTGGTCCAGGCTTCGGTCCGGGTGTTGTAGGCGTTCCGGGTGCTGGTGTTCCGGGCG   960
      GCCCACCAGGTCCGAAGCCAGGCCCACAACATCCGCAAGGCCCACGACCACAAGGCCCGC

G  G  P  G  F  G  P  G  V  V  G  V  P  G  A  V  P  G  V

961  TAGGTGTTCCAGGTGCGGGCATCCCGGTTGTACCGGGTGCAGGTATCCCGGGCGCTGCGG  1020
      ATCCACAAGGTCCACGCCCGTAGGGCCAACATGGCCCACGTCCATAGGGCCCGCGACGCC

G  V  P  G  A  G  I  P  V  V  P  G  A  G  I  P  G  A  A  V

1021  TTCCAGGTGTTGTATCCCCGGAAGCGGCAGCTAAGGCTGCTGCGAAAGCTGCGAAATACG  1080
      AAGGTCCACAACATAGGGGCCTTCGCCGTCGATTCCGACGACGCTTTCGACGCTTTATGC

P  G  V  V  S  P  E  A  A  A  K  A  A  A  K  A  A  K  Y  G

1081  GAGCTCGTCCGGGCGTTGGTGTTGGTGGCATCCCGACCTACGGTGTAGGTGCAGGCGGTT  1140
      CTCGAGCAGGCCCGCAACCACAACCACCGTAGGGCTGGATGCCACATCCACGTCCGCCAA

A  R  P  G  V  G  V  G  G  I  P  T  Y  G  V  A  G  G  F

1141  TCCCAGGTTTCGGCGTTGGTGTTGGTGGCATCCCGGGTGTAGCTGGTGTTCCGTCTGTTG  1200
      AGGGTCCAAAGCCGCAACCACAACCACCGTAGGGCCCACATCGACCACAAGGCAGACAAC

P  G  F  G  V  G  V  G  G  I  P  G  V  A  G  V  P  S  V  G

1201  GTGGCGTACCGGGTGTTGGTGGCGTTCCAGGTGTAGGTATCTCCCCGGAAGCGCAGGCAG  1260
      CACCGCATGGCCCACAACCACCGCAAGGTCCACATCCATAGAGGGGCCTTCGCGTCCGTC

G  V  P  G  V  G  G  V  P  G  V  G  I  S  P  E  A  Q  A  A

1261  CTGCGGCAGCTAAAGCAGCGAAGTACGGCGTTGGTACTCCGGCGGCAGCAGCTGCTAAAG  1320
      GACGCCGTCGATTTCGTCGCTTCATGCCGCAACCATGAGGCCGCCGTCGTCGACGATTTC

A  A  A  K  A  A  K  Y  G  V  G  T  P  A  A  A  A  K  A

1321  CAGCGGCTAAAGCAGCGCAGTTCGGACTAGTTCCGGGCGTAGGTGTTGCGCCAGGTGTTG  1380
      GTCGCCGATTTCGTCGCGTCAAGCCTGATCAAGGCCCGCATCCACAACGCGGTCCACAAC

```
1381  GCGTAGCACCGGGTGTTGGTGTTGCTCCGGGCGTAGGTCTGGCACCGGGTGTTGGCGTTG  1440
      CGCATCGTGGCCCACAACCACAACGAGGCCCGCATCCAGACCGTGGCCCACAACCGCAAC

V  A  P  G  V  G  V  A  P  G  V  G  L  A  P  G  V  G  V  A

1441  CACCAGGTGTAGGTGTTGCGCCGGGCGTTGGTGTAGCACCGGGTATCGGTCCGGGTGGCG  1500
      GTGGTCCACATCCACAACGCGGCCCGCAACCACATCGTGGCCCATAGCCAGGCCCACCGC

P  G  V  G  V  A  P  G  V  G  V  A  P  G  I  G  P  G  G  V

1501  TTGCGGCTGCTGCGAAATCTGCTGCGAAGGTTGCTGCGAAAGCGCAGCTGCGTGCAGCAG  1560
      AACGCCGACGACGCTTTAGACGACGCTTCCAACGACGCTTTCGCGTCGACGCACGTCGTC

A  A  A  A  K  S  A  A  K  V  A  A  K  A  Q  L  R  A  A  A

1561  CTGGTCTGGGTGCGGGCATCCCAGGTCTGGGTGTAGGTGTTGGTGTTCCGGGCCTGGGTG  1620
      GACCAGACCCACGCCCGTAGGGTCCAGACCCACATCCACAACCACAAGGCCCGGACCCAC

G  L  G  A  G  I  P  G  L  G  V  G  V  G  V  P  G  L  G  V

1621  TAGGTGCAGGGGTACCGGGCCTGGGTGTTGGTGCAGGCGTTCCGGGTTTCGGTGCTGGCG  1680
      ATCCACGTCCCCATGGCCCGGACCCACAACCACGTCCGCAAGGCCCAAAGCCACGACCGC

G  A  G  V  P  G  L  G  V  G  A  G  V  P  G  F  G  A  G  A

1681  CGGACGAAGGTGTACGTCGTTCCCTGTCTCCAGAACTGCGTGAAGGTGACCCGTCCTCTT  1740
      GCCTGCTTCCACATGCAGCAAGGGACAGAGGTCTTGACGCACTTCCACTGGGCAGGAGAA

D  E  G  V  R  R  S  L  S  P  E  L  R  E  G  D  P  S  S  S

1741  CCCAGCACCTGCCGTCTACCCCGTCCTCTCCACGTGTTCCGGGCGCGCTGGCTGCTGCGA  1800
      GGGTCGTGGACGGCAGATGGGGCAGGAGAGGTGCACAAGGCCCGCGCGACCGACGACGCT

Q  H  L  P  S  T  P  S  S  P  R  V  P  G  A  L  A  A  A  K

1801  AAGCGGCGAAATACGGTGCAGCGGTTCCGGGTGTACTGGGCGGTCTGGGTGCTCTGGGCG  1860
      TTCGCCGCTTTATGCCACGTCGCCAAGGCCCACATGACCCGCCAGACCCACGAGACCCGC

```
1861  GTGTTGGTATCCCGGGCGGTGTTGTAGGTGCAGGCCCAGCTGCAGCTGCTGCTGCGGCAA  1920
      CACAACCATAGGGCCCGCCACAACATCCACGTCCGGGTCGACGTCGACGACGACGCCGTT
       V  G  I  P  G  G  V  V  G  A  G  P  A  A  A  A  A  A  A  K

1921  AGGCAGCGGCGAAAGCAGCTCAGTTCGGTCTGGTTGGTGCAGCAGGTCTGGGCGGTCTGG  1980
      TCCGTCGCCGCTTTCGTCGAGTCAAGCCAGACCAACCACGTCGTCCAGACCCGCCAGACC
       A  A  A  K  A  A  Q  F  G  L  V  G  A  A  G  L  G  G  L  G

1981  GTGTTGGCGGTCTGGGTGTACCGGGCGTTGGTGGTCTGGGTGGCATCCCGCCGGCGGCGG  2040
      CACAACCGCCAGACCCACATGGCCCGCAACCACCAGACCCACCGTAGGGCGGCCGCCGCC
       V  G  G  L  G  V  P  G  V  G  G  L  G  G  I  P  P  A  A  A

2041  CAGCTAAAGCGGCTAAATACGGTGCAGCAGGTCTGGGTGGCGTTCTGGGTGGTGCTGGTC  2100
      GTCGATTTCGCCGATTTATGCCACGTCGTCCAGACCCACCGCAAGACCCACCACGACCAG
       A  K  A  A  K  Y  G  A  A  G  L  G  G  V  L  G  G  A  G  Q

2101  AGTTCCCACTGGGCGGTGTAGCGGCACGTCCGGGTTTCGGTCTGTCCCCGATCTTCCCAG  2160
      TCAAGGGTGACCCGCCACATCGCCGTGCAGGCCCAAAGCCAGACAGGGGCTAGAAGGGTC
       F  P  L  G  G  V  A  A  R  P  G  F  G  L  S  P  I  F  P  G

2161  GCGGTGCATGCCTGGGTAAAGCTTGCGGCCGTAAACGTAAATAATGATAG            2210
      CGCCACGTACGGACCCATTTCGAACGCCGGCATTTGCATTTATTACTATCCTAG
       G  A  C  L  G  K  A  C  G  R  K  R  K  *  *  *
```

Figure 2(e)

```
  1 GGVPGAIPGGVPGGVFYPGAGIGALGGGALGPGGKPLKPVPGGLAGAGLG 50
    |||||||||||||||||||||||||||||||||||||||||||||||||
  1 GGVPGAIPGGVPGGVFYPGAGIGALGGGALGPGGKPLKPVPGGLAGAGLG 50

51 AGLGAFPAVTFPGALVPGGVADAAAAYKAAKAGAGLGGVPGVGGLGVSAG 100
    |||||||||||||||||||||||||||||||||||||||||||||||||
 51 AGLGAFPAVTFPGALVPGGVADAAAAYKAAKAGAGLGGVPGVGGLGVSAG 100

101 AVVPQPGAGVKPGKVPGVGLPGVYPGGVLPGARFPGVGVLPGVPTGAGVK 150
    |||||||||||||||||||||||||||||||||||||||||||||||||
101 AVVPQPGAGVKPGKVPGVGLPGVYPGGVLPGARFPGVGVLPGVPTGAGVK 150

151 PKAPGVGGAFAGIPGVGPFGGPQPGVPLGYPIKAPKLPGGYGLPYTTGKL 200
    |||||||||||||||||||||||||||||||||||||||||||||||||
151 PKAPGVGGAFAGIPGVGPFGGPQPGVPLGYPIKAPKLPGGYGLPYTTGKL 200

201 PYGYGPGGVAGAAGKAGYPTGTGVGPQAAAAAAKAAAKFGAGAAGVLPG 250
    |||||||||||||||||||||||||||||||||||||||||||||||||
201 PYGYGPGGVAGAAGKAGYPTGTGVGPQAAAAAAKAAAKFGAGAAGVLPG 250

251 VGGAGVPGVPGAIPGIGGIAGVGTPAAAAAAAAAKAAKYGAAAGLVPGG 300
    |||||||||||||||||||||||||||||||||||||||||||||||||
251 VGGAGVPGVPGAIPGIGGIAGVGTPAAAAAAAAAKAAKYGAAAGLVPGG 300

301 PGFGPGVVGVPGAGVPGVGVPGAGIPVVPGAGIPGAAVPGVVSPEAAAKA 350
    |||||||||||||||||||||||||||||||||||||||||||||||||
301 PGFGPGVVGVPGAGVPGVGVPGAGIPVVPGAGIPGAAVPGVVSPEAAAKA 350

351 AAKAAKYGARPGVGVGGIPTYGVGAGGFPGFGVGVGGIPGVAGVPSVGGV 400
    |||||||||||||||||||||||||||||||||||||||||||||||||
351 AAKAAKYGARPGVGVGGIPTYGVGAGGFPGFGVGVGGIPGVAGVPSVGGV 400

401 PGVGGVPGVGISPEAQAAAAAKAAKYGVGTPAAAAAKAAAKAAQFGLVPG 450
    |||||||||||||||||||||||||||||||||||||||||||||||||
401 PGVGGVPGVGISPEAQAAAAAKAAKYGVGTPAAAAAKAAAKAAQFGLVPG 450

451 VGVAPGVGVAPGVGVAPGVGLAPGVGVAPGVGVAPGVGVAPGIGPGGVAA 500
    |||||||||||||||||||||||||||||||||||||||||||||||||
451 VGVAPGVGVAPGVGVAPGVGLAPGVGVAPGVGVAPGVGVAPGIGPGGVAA 500

501 AAKSAAKVAAKAQLRAAAGLGAGIPGLGVGVGVPGLGVGAGVPGLGVGAG 550
    |||||||||||||||||||||||||||||||||||||||||||||||||
501 AAKSAAKVAAKAQLRAAAGLGAGIPGLGVGVGVPGLGVGAGVPGLGVGAG 550

551 VPGFGAGADEGVRRSLSPELREGDPSSSQHLPSTPSSPRVPGALAAAKAA 600
    ||||||                                   |||||||||
551 VPGFGA.................................VPGALAAAKAA 567

601 KYGAAVPGVLGGLGALGGVGIPGGVVGAGPAAAAAAKAAAKAAQFGLVG 650
    |||||||||||||||||||||||||||||||||||||||||||||||||
568 KYGAAVPGVLGGLGALGGVGIPGGVVGAGPAAAAAAKAAAKAAQFGLVG 617

651 AAGLGGLGVGGLGVPGVGGLGGIPPAAAAKAAKYGAAGLGGVLGGAGQFP 700
    |||||||||||||||||||||||||||||||||||||||||||||||||
618 AAGLGGLGVGGLGVPGVGGLGGIPPAAAAKAAKYGAAGLGGVLGGAGQFP 667

701 LGGVAARPGFGLSPIFPGGACLGKACGRKRK 731
    ||||||||||||||||||||||||||||||
668 LGGVAARPGFGLSPIFPGGACLGKACGRKRK 698
```

Figure 3

```
  1 ATGGGTGGCGTTCCGGGTGCTGTTCCGGGTGGCGTTCCGGGTGGTGTATT 50
    ||||||||||||||||||||||||||||||||||||||||||||||||
  1 MetGlyGlyValProGlyAlaValProGlyGlyValProGlyGlyValPh 17

51 CTACCCAGGCGCGGGTTTCGGTGCTGTTCCGGGTGGCGTTGCAGACGCAG 100
    ||||||||||||||||||||||||||||||||||||||||||||||||
 18 eTyrProGlyAlaGlyPheGlyAlaValProGlyGlyValAlaAspAlaA 34

101 CTGCTGCGTACAAAGCGGCAAAGGCAGGTGCGGGTCTGGGCGGGGTACCA 150
    ||||||||||||||||||||||||||||||||||||||||||||||||
 35 laAlaAlaTyrLysAlaAlaLysAlaGlyAlaGlyLeuGlyGlyValPro 50

151 GGTGTTGGCGGTCTGGGTGTATCTGCTGGCGCAGTTGTTCCGCAGCCGGG 200
    ||||||||||||||||||||||||||||||||||||||||||||||||
 51 GlyValGlyGlyLeuGlyValSerAlaGlyAlaValValProGlnProGl 67

201 TGCAGGTGTAAAACCGGGCAAAGTTCCAGGTGTTGGTCTGCCGGGCGTAT 250
    ||||||||||||||||||||||||||||||||||||||||||||||||
 68 yAlaGlyValLysProGlyLysValProGlyValGlyLeuProGlyValT 84

251 ACCCGGGTTTCGGTGCTGTTCCGGGCGCGCGTTTCCCAGGTGTTGGTGTA 300
    ||||||||||||||||||||||||||||||||||||||||||||||||
 85 yrProGlyPheGlyAlaValProGlyAlaArgPheProGlyValGlyVal 100

301 CTGCCGGGCGTTCCGACCGGTGCAGGTGTTAAACCGAAGGCACCAGGTGT 350
    ||||||||||||||||||||||||||||||||||||||||||||||||
101 LeuProGlyValProThrGlyAlaGlyValLysProLysAlaProGlyVa 117

351 AGGCGGCGCGTTCGCGGGTATCCCGGGTGTTGGCCCGTTCGGTGGTCCGC 400
    ||||||||||||||||||||||||||||||||||||||||||||||||
118 lGlyGlyAlaPheAlaGlyIleProGlyValGlyProPheGlyGlyProG 134

401 AGCCAGGCGTTCCGCTGGGTTACCCGATCAAAGCGCCGAAGCTTCCAGGT 450
    ||||||||||||||||||||||||||||||||||||||||||||||||
135 lnProGlyValProLeuGlyTyrProIleLysAlaProLysLeuProGly 150

451 GGCTACGGTCTGCCGTACACCACCGGTAAACTGCCGTACGGCTACGGTCC 500
    ||||||||||||||||||||||||||||||||||||||||||||||||
151 GlyTyrGlyLeuProTyrThrThrGlyLysLeuProTyrGlyTyrGlyPr 167

501 GGGTGGCGTAGCAGGTGCTGCGGGTAAAGCAGGCTACCCAACCGGTACTG 550
    ||||||||||||||||||||||||||||||||||||||||||||||||
168 oGlyGlyValAlaGlyAlaAlaGlyLysAlaGlyTyrProThrGlyThrG 184

551 GTGTTGGTCCGCAGGCTGCTGCGGCAGCTGCGGCGAAGGCAGCAGCAAAA 600
    ||||||||||||||||||||||||||||||||||||||||||||||||
185 lyValGlyProGlnAlaAlaAlaAlaAlaAlaAlaLysAlaAlaAlaLys 200

601 TTCGGCGCGGGTGCAGCGGGTTTCGGTGCTGTTCCGGGCGTAGGTGGTGC 650
    ||||||||||||||||||||||||||||||||||||||||||||||||
201 PheGlyAlaGlyAlaAlaGlyPheGlyAlaValProGlyValGlyGlyAl 217

651 TGGCGTTCCGGGTGTTCCAGGTGCGATCCCGGGCATCGGTGGTATCGCAG 700
    ||||||||||||||||||||||||||||||||||||||||||||||||
218 aGlyValProGlyValProGlyAlaIleProGlyIleGlyGlyIleAlaG 234

701 GCGTAGGTACTCCGGCGGCCGCTGCGGCTGCGGCAGCTGCGGCGAAAGCA 750
    ||||||||||||||||||||||||||||||||||||||||||||||||
235 lyValGlyThrProAlaAlaAlaAlaAlaAlaAlaAlaAlaAlaLysAla 250

751 GCTAAATACGGTGCGGCAGCAGGCCTGGTTCCGGGTGGTCCAGGCTTCGG 800
    ||||||||||||||||||||||||||||||||||||||||||||||||
251 AlaLysTyrGlyAlaAlaAlaGlyLeuValProGlyGlyProGlyPheGl 267

801 TCCGGGTGTTGTAGGCGTTCCGGGTTTCGGTGCTGTTCCGGGCGTAGGTG 850
    ||||||||||||||||||||||||||||||||||||||||||||||||
```

Figure 4(a)

```
268 yProGlyValValGlyValProGlyPheGlyAlaValProGlyValGlyV 284
851 TTCCAGGTGCGGGCATCCCGGTTGTACCGGGTGCAGGTATCCCGGGCGCT 900
    |||||||||||||||||||||||||||||||||||||||||||||||||
285 alProGlyAlaGlyIleProValValProGlyAlaGlyIleProGlyAla 300

901 GCGGGTTTCCGGTGCTGTATCCCCGGAAGCGGCAGCTAAGGCTGCTGCGAA 950
    |||||||||||||||||||||||||||||||||||||||||||||||||
301 AlaGlyPheGlyAlaValSerProGluAlaAlaAlaLysAlaAlaAlaLy 317

951 AGCTGCGAAATACGGAGCTCGTCCGGGCGTTGGTGTTGGTGGCATCCCGA 1000
    |||||||||||||||||||||||||||||||||||||||||||||||||
318 sAlaAlaLysTyrGlyAlaArgProGlyValGlyValGlyGlyIleProT 334

1001 CCTACGGTGTAGGTGCAGGCGGTTTCCCAGGTTTCGGCGTTGGTGTTGGT 1050
     |||||||||||||||||||||||||||||||||||||||||||||||||
335  hrTyrGlyValGlyAlaGlyGlyPheProGlyPheGlyValGlyValGly 350

1051 GGCATCCCGGGTGTAGCTGGTGTTCCGTCTGTTGGTGGCGTACCGGGTGT 1100
     |||||||||||||||||||||||||||||||||||||||||||||||||
351  GlyIleProGlyValAlaGlyValProSerValGlyGlyValProGlyVa 367

1101 TGGTGGCGTTCCAGGTGTAGGTATCTCCCGGAAGCGCAGGCAGCTGCGG 1150
     |||||||||||||||||||||||||||||||||||||||||||||||||
368  lGlyGlyValProGlyValGlyIleSerProGluAlaGlnAlaAlaAlaA 384

1151 CAGCTAAAGCAGCGAAGTACGGCGTTGGTACTCCGGCGGCAGCAGCTGCT 1200
     |||||||||||||||||||||||||||||||||||||||||||||||||
385  laAlaLysAlaAlaLysTyrGlyValGlyThrProAlaAlaAlaAlaAla 400

1201 AAAGCAGCGGCTAAAGCAGCGCAGTTCGGACTAGTTCCGGGCGTAGGTGT 1250
     |||||||||||||||||||||||||||||||||||||||||||||||||
401  LysAlaAlaAlaLysAlaAlaGlnPheGlyLeuValProGlyValGlyVa 417

1251 TGCGCCAGGTGTTGGCGTAGCACCGGGTGTTGGTGTTGCTCCGGGCGTAG 1300
     |||||||||||||||||||||||||||||||||||||||||||||||||
418  lAlaProGlyValGlyValAlaProGlyValGlyValAlaProGlyValG 434

1301 GTCTGGCACCGGGTGTTGGCGTTGCACCAGGTGTAGGTGTTGCGCCGGGC 1350
     |||||||||||||||||||||||||||||||||||||||||||||||||
435  lyLeuAlaProGlyValGlyValAlaProGlyValGlyValAlaProGly 450

1351 GTTGGTGTAGCACCGGGTATCGGTCCGGGTGGCGTTGCGGCTGCTGCGAA 1400
     |||||||||||||||||||||||||||||||||||||||||||||||||
451  ValGlyValAlaProGlyIleGlyProGlyGlyValAlaAlaAlaAlaLy 467

1401 ATCTGCTGCGAAGGTTGCTGCGAAAGCGCAGCTGCGTGCAGCAGCTGGTC 1450
     |||||||||||||||||||||||||||||||||||||||||||||||||
468  sSerAlaAlaLysValAlaAlaLysAlaGlnLeuArgAlaAlaAlaGlyL 484

1451 TGGGTGCGGGCATCCCAGGTCTGGGTGTAGGTGTTGGTGTTCCGGGCCTG 1500
     |||||||||||||||||||||||||||||||||||||||||||||||||
485  euGlyAlaGlyIleProGlyLeuGlyValGlyValGlyValProGlyLeu 500

1501 GGTGTAGGTGCAGGGGTACCGGGCCTGGGTGTTGGTGCAGGCGTTCCGGG 1550
     |||||||||||||||||||||||||||||||||||||||||||||||||
501  GlyValGlyAlaGlyValProGlyLeuGlyValGlyAlaGlyValProGl 517

1551 TTTCGGTGCTGTTCCGGGCGCGCTGGCTGCTGCGAAAGCGGCGAAATACG 1600
     |||||||||||||||||||||||||||||||||||||||||||||||||
518  yPheGlyAlaValProGlyAlaLeuAlaAlaAlaLysAlaAlaLysTyrG 534

1601 GTGCTGTTCCGGGTGTACTGGGCGGTCTGGGTGCTCTGGGCGGTGTTGGT 1650
     |||||||||||||||||||||||||||||||||||||||||||||||||
535  lyAlaValProGlyValLeuGlyGlyLeuGlyAlaLeuGlyGlyValGly 550

1651 ATCCCGGGCGGTGTTGTAGGTGCAGGCCCAGCTGCAGCTGCTGCGGGC 1700
     |||||||||||||||||||||||||||||||||||||||||||||||||
551  IleProGlyGlyValValGlyAlaGlyProAlaAlaAlaAlaAlaAlaAl 567
```

Figure 4(b)

```
1701 AAAGGCAGCGGCGAAAGCAGCTCAGTTCGGTCTGGTTGGTGCAGCAGGTC 1750
     |||||||||||||||||||||||||||||||||||||||||||||||||
 568 aLysAlaAlaAlaLysAlaAlaGlnPheGlyLeuValGlyAlaAlaGlyL 584

1751 TGGGCGGTCTGGGTGTTGGCGGTCTGGGTGTACCGGGCGTTGGTGGTCTG 1800
     |||||||||||||||||||||||||||||||||||||||||||||||||
 585 euGlyGlyLeuGlyValGlyGlyLeuGlyValProGlyValGlyGlyLeu 600

1801 GGTGGCATCCCGCCGGCGGCGGCAGCTAAAGCGGCTAAATACGGTGCAGC 1850
     |||||||||||||||||||||||||||||||||||||||||||||||||
 601 GlyGlyIleProProAlaAlaAlaAlaLysAlaAlaLysTyrGlyAlaAl 617

1851 AGGTCTGGGTGGCGTTCTGGGTGGTGCTGGTCAGTTGCCACTGGGCGGTG 1900
     |||||||||||||||||||||||||||||||||||||||||||||||||
 618 aGlyLeuGlyGlyValLeuGlyGlyAlaGlyGlnPheProLeuGlyGlyV 634

1901 TAGCGGCACGTCCGGGTTTCGGTCTGTCCCGGATCTTCCCAGGCGGTGCA 1950
     |||||||||||||||||||||||||||||||||||||||||||||||||
 635 alAlaAlaArgProGlyPheGlyLeuSerProIlePheProGlyGlyAla 650

1951 TGCCTGGGTAAAGCTTGCGGCCGTAAACGTAAA 1983
     |||||||||||||||||||||||||||||||||
 651 CysLeuGlyLysAlaCysGlyArgLysArgLys 661
```

Figure 4(c)

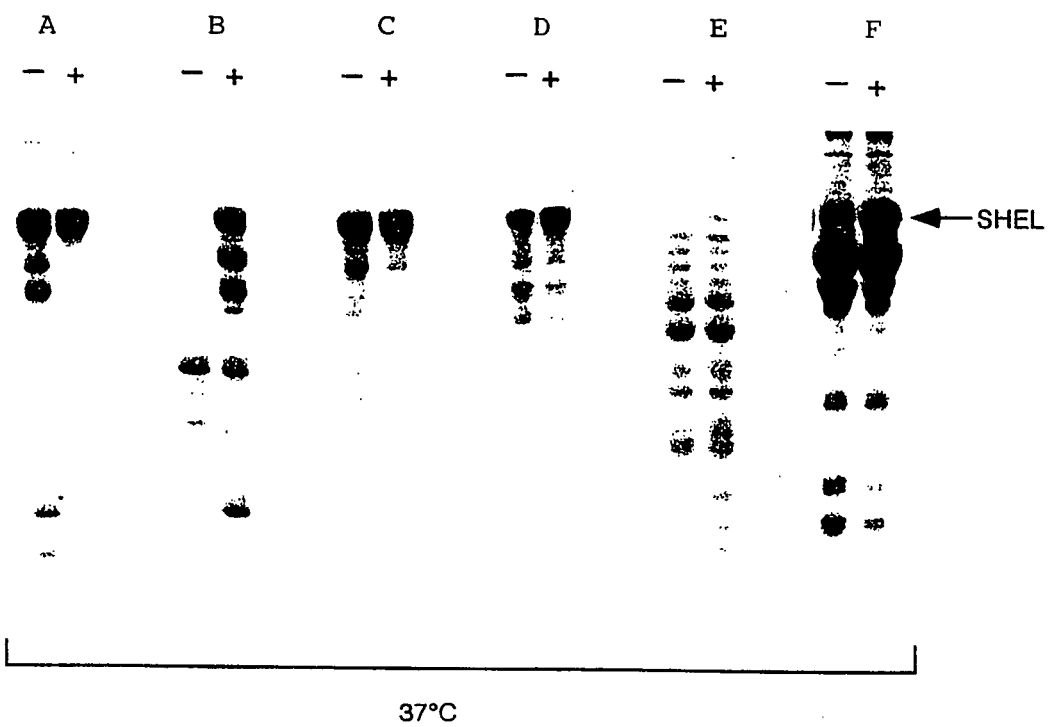
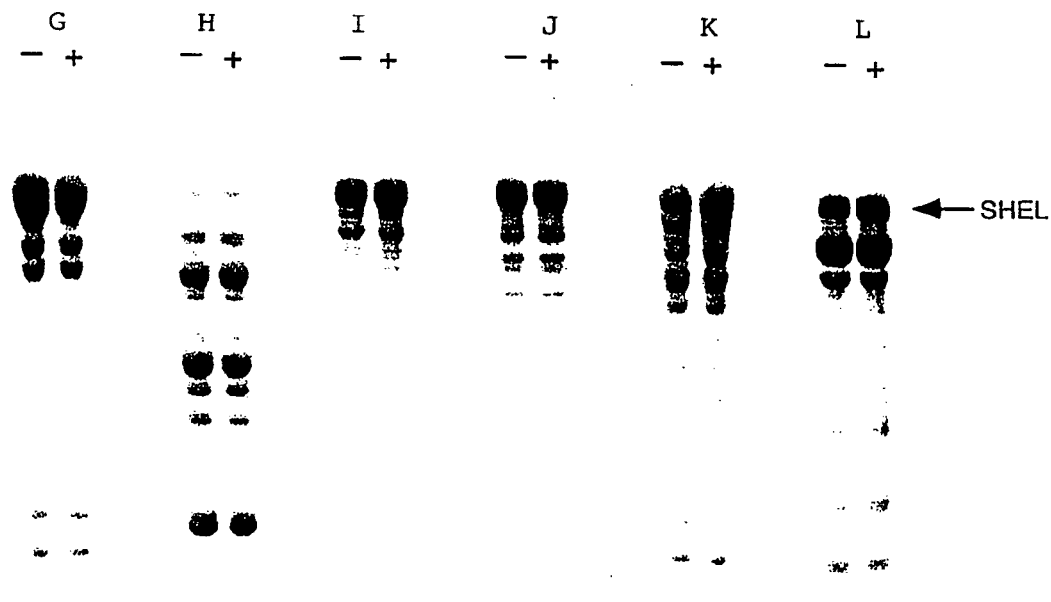
Figure 13

… # PROTEASE SUSCEPTIBILITY II

BACKGROUND OF THE INVENTION

The present invention relates to: manipulation of the amino acid sequence of tropoelastin, particularly human tropoelastin, to modify its protease susceptibility; to tropoelastin derivatives having modified protease susceptibility; to peptidomimetic molecules which contain amino acid sequences which correspond to or incorporate the protease susceptible sequences of tropoelastin; and to uses of the tropoelastin derivatives and peptidomimetic molecules.

The invention also relates to nucleic acid molecules and genetic constructs encoding the amino acid sequences of the derivatives and peptidomimetic molecules of the invention.

The insoluble cross-linked elastin molecule is highly resistant to proteolytic degradation by many proteases. However, tropoelastin, the soluble precursor of elastin, is far more vulnerable to proteolysis. Attempts at purifying tropoelastin from tissues usually result in a collection of degraded products. This degradation can be decreased by using traditional inhibitors of serine proteases (Franzblau et al., 1989; Rucker, 1982, Rich and Foster, 1984; Sandberg and Wolt, 1982). Specific degradation has also been noted in cell culture of smooth muscle cells which was attributed to metalloproteinases (Hayashi et al., 1995). Even highly purified tropoelastin can degrade into discrete bands on prolonged storage. This observation has led to a hypothesis that mammalian tropoelastin is occasionally co-purified with an intrinsic protease which will promote its gradual breakdown (Mecham et al., 1976; Mecham et al., 1977; Mecham and Foster, 1977). Experiments have shown that mammalian serum contains proteases which are capable of degrading tropoelastin (Romero et al., 1986). Thus, any newly-synthesized unprotected tropoelastin exposed to blood, such as in a blood vessel wall, would be rapidly degraded. Serum has also been shown to induce elastase activity in smooth muscle cells leading to degradation of elastin (Kobayashi et al., 1994). Elastin peptides are known to be chemotactic and this could be a role of tropoelastin proteolysis in vivo (Grosso and Scott, 1993; Bisaccia et al., 1994). However, proteolysis could also result in inadequate or faulty elastin fiber repair at the site of injury. Serine protease inhibitors have been shown to reduce the degradation of tropoelastin caused by serum (Romero, et al., 1986). These experiments suggested that kallikrein was a candidate serum protease. Other experiments (McGowan et al., 1996) proposed that plasmin was a major protease involved. Thrombin has been used to digest heterogeneous porcine tropoelastin in vitro (Torres et al., 1976). However, none of these studies has provided indication of where the tropoelastin molecule is cut by proteases.

BRIEF DESCRIPTION OF THE DRAWINGS

FIG. 2 shows the nucleotide sequence and amino acid sequence of SHEL. The positions of the protease recognition sites are underlined. The nucleic acid sequence is show in SEQ ID NO:3 and the amino acid of SHEL is shown in SEQ ID NO:4.

FIG. 3 shows the amino acid sequence of SHELδ26A (bottom line) compared to the amino acid sequence of SHEL [aa 3–733 of SEQ ID NO: 4]. The amino acid sequence of SHELδ26A is shown in SEQ ID NO:5.

FIG. 4 shows the nucleotide sequence and amino acid sequence of SHELδmod. The nucleic acid sequences are nucleotides (nt) 1–1983 of SEQ ID NO:2. The amino acid sequence of SHELδmod is shown in SEQ ID NO:6.

FIG. 13 shows SDS-PAGE analysis of the effect of coacervation on the degradation of SHEL by proteases. SHEL was incubated in the presence (+) or absence (−) of a concentration of NaCl conducive to coacervation of SHEL at 37° C. with A: kallikrein; B: thrombin; C: HLE; D: trypsin; E: plasmin and F: serum; or in the presence (+) or absence (−) of a concentration of NaCl conducive to coacervation of SHEL at 16° C. with G: kallikrein; H: thrombin; I: HLE; J: trypsin; K: plasmin and L: serum.

DETAILED DESCRIPTION OF THE INVENTION

Figure 1:
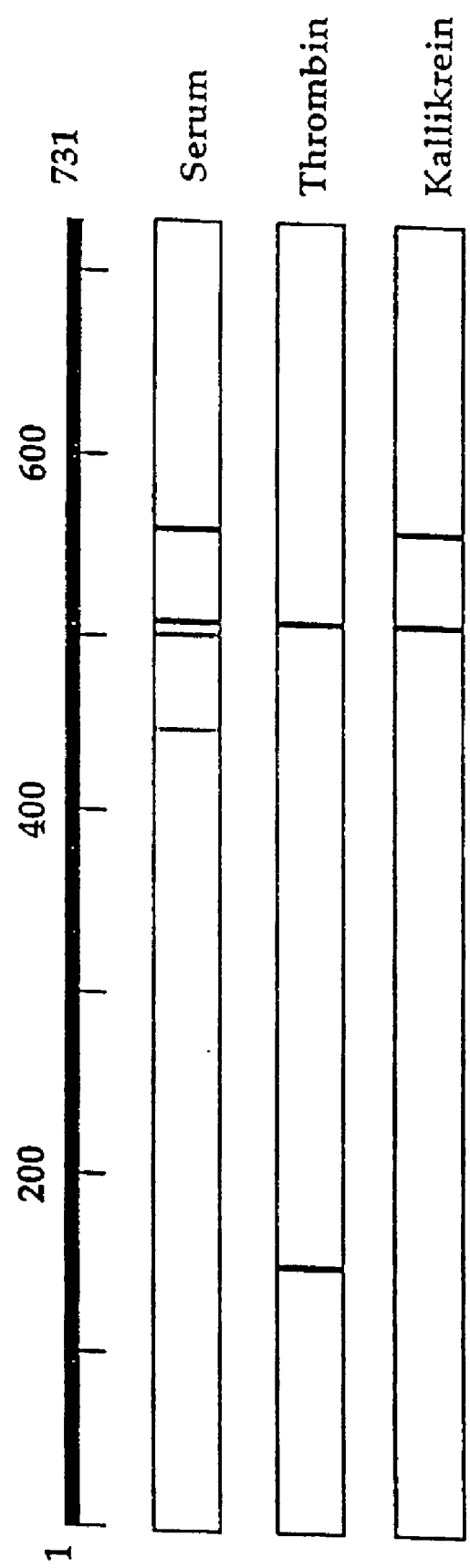
FIG. 1 shows a schematic diagram illustrating the relative positions of protease sites identified by N-terminal sequencing for serum, kallikrein and thrombin. Major sites are indicated with a solid bar while minor sites are indicated with a stippled bar. Since most plasmin fragments contained the same N-terminal sequence the site of cleavage could not be identified unambiguously. The trypsin fragments identified similarly all contained the same N-terminal sequence. Therefore, the likely regions of cleavage for plasmin and trypsin are not shown.

In purifying a defined species of recombinant human tropoelastin (Martin et al., 1995) from its fusion partner the present inventor observed limited and reproducible cleavage of the tropoelastin, by thrombin. The pattern of degradation as seen on SDS-polyacrylamide gels was similar to that seen by others during purification and storage (Mecham et al., 1977). The present inventor recognised the possibility that this may be because certain portions of tropoelastin are more susceptible to protease action or are more readily available to proteases because of tropoelastin's conformation in solution. A comparison of the sizes of the protease cleavage products with the amino acid sequence of tropoelastin and the consensus cleavage sites for the proteases being examined revealed that of the many sites in the tropoelastin amino acid sequence which are homologous to consensus sequences for particular proteases, few were readily digested by proteases. By mapping the sites at which digestion was taking place, susceptible regions were identified thus providing the first precise mapping of protease cleavage sites within any tropoelastin.

From the determination of these susceptible regions, tropoelastin amino acid sequences in these susceptible regions can be modified thus providing reduced tropoelastin derivatives which have a reduced or eliminated protease susceptibility under particular conditions, as compared with the protease susceptibility of tropoelastin under the same conditions.

In the specification and claims, "reduced tropoelastin derivative" means a molecule having a modification of an amino acid sequence in a susceptible region of tropoelastin, which molecule is folded in a functional conformation. "Functional conformation" is defined below. The modification of the amino acid sequence in the susceptible region causes reduced or eliminated protease susceptibility. Reduced tropoelastin derivatives may correspond to full length tropoelastin molecules, single domains of tropoelastin which are encoded by specific exons of the tropoelastin gene or peptides which are encoded by all or part of two neighbouring exons of the tropoelastin gene.

Reduced tropoelastin derivatives may be produced by mutation events including for example, single point mutation in a nucleotide sequence which cause a residue substitution in an amino acid sequence in a susceptible region, or mutation events in a nucleotide sequence which cause an amino acid insertion or deletion in an amino acid sequence in a susceptible region. Reduced tropoelastin derivatives can also be produced by mutation of tropoelastin sequences, in regions of the tropoelastin molecule which are susceptible to protease digestion, and further mutation in other regions of tropoelastin. The further mutations may or may not alter the susceptibility of the reduced tropoelastin derivative to proteases. Reduced tropoelastin derivatives which contain these mutations may be produced synthetically.

Reduced tropoelastin derivatives may alternatively be produced by chemical modification of amino acid side chains in the derivative which chemically modifies a susceptible region.

Reduced tropoelastin derivatives may in another alternative be produced by protease digestion. Thus according to the invention, a protease digestion product of tropoelastin, which, as a result of digestion, has lost an amino acid sequence which is in a susceptible region, is a reduced tropoelastin derivative.

Reduced tropoelastin derivatives can also be produced by modification of tropoelastin variant amino acid sequences, in regions of the tropoelastin molecule which are susceptible to protease digestion.

In the specification and claims, "variants of tropoelastin" or "tropoelastin variants" means molecules which retain one or more properties of the corresponding tropoelastin molecule, for example, elastin-like properties or macro-molecular binding properties. Elastin-like properties include the phenomenon of recoil after molecular distention and the ability to undergo cross-linking and coacervation. Macro-molecular binding properties include the ability to interact with other macro-molecules, for example glycosylaminoglycans. Tropoelastin variants have an amino acid sequence which is homologous to all or part of the amino acid sequence of a tropoelastin splice form. For the purposes of this description, "homology" between the amino acid sequence of a particular variant and all or part of a tropoelastin splice form connotes a likeness short of identity, indicative of a derivation of one sequence from the other. In particular, an amino acid sequence is homologous to all or part of a tropoelastin sequence if the alignment of that amino acid sequence with the relevant tropoelastin sequence reveals an identity of about 65% over any 20 amino acid stretch or over any repetitive element of the molecules shorter than 20 amino acids in length. Such a sequence comparison can be performed via known algorithms such as that of Lipman and Pearson (1985). Tropoelastin variants may contain amino acid sequence differences as compared with tropoelastin, at a region susceptible to proteolysis, which differences do not alter the protease susceptibility of the tropoelastin variant as compared with tropoelastin. An example of such an amino acid sequence difference at a susceptible region in a tropoelastin variant may be a conservative amino acid substitution.

Thus reduced tropoelastin derivatives may be produced by mutation of a tropoelastin variant amino acid sequence, including for example, single point mutations in a nucleotide sequence which causes a residue substitution in an amino acid sequence in a susceptible region of tropoelastin. The reduced tropoelastin derivatives may also be produced by mutation of a tropoelastin variant amino acid sequence, including for example mutation events in a nucleotide sequence which cause an amino acid insertion or deletion in an amino acid sequence in a susceptible region of tropoelastin. Reduced tropoelastin derivatives can be produced by mutation of tropoelastin variant sequences, in regions of the tropoelastin molecule which are susceptible to protease digestion, and further mutation in other regions of the reduced tropoelastin variant. The further mutations may or may not alter the susceptibility of the reduced tropoelastin derivative to proteases. Reduced tropoelastin derivatives which are produced by the mutation of a tropoelastin variant may be produced synthetically.

Alternatively, reduced tropoelastin derivatives may be produced by chemical modification of amino acid side chains in the derivative which chemically modifies a susceptible region.

Alternatively, reduced tropoelastin derivatives may also be produced by protease digestion of a tropoelastin variant. Thus according to the invention, a protease digestion product of a tropoelastin variant, which, as a result of digestion, has lost an amino acid sequence in a susceptible region, is a reduced tropoelastin derivative.

It is known that tropoelastin genes in nature are expressed as multiple transcripts which are distinguished by alternative splicing of the mRNA as described in, for instance, Indik et al (1990); Oliver et al (1987); Heim et al (1991); Raju et al (1987) and Yeh et al (1987). The methods of the present invention can also be applied to the different splice forms of tropoelastin. The skilled addressee will readily recognise that in applying the methods of the invention to various splice forms of tropoelastin, account must be taken of the presence or absence of the identified cleavage sites in the amino acid sequence of the particular splice form in question.

Human tropoelastins are described by Indik et al (1990) and Tassabehji et al (1997). Bressan et al (1987) describe the amino acid sequence of chick tropoelastin, while Raju et al (1987) describe the amino acid sequence of bovine tropoelastin and Pierce et al (1992) describe the amino acid sequence of rat tropoelastin. Again taking account of variations in amino acid sequence and the existence of different splice forms, the skilled addressee will recognise that the methods of the invention can be applied to tropoelastins from other species.

In a first aspect the present invention provides a method for reducing or eliminating the susceptibility of a tropoelastin or tropoelastin variant amino acid sequence to proteolysis which method comprises mutating at least one sub-sequence in the tropoelastin or tropoelastin variant amino acid sequence, to reduce or eliminate the susceptibility of the tropoelastin or tropoelastin variant to proteolysis.

In the specification and claims, a "sub-sequence" means a sequence which is capable of being cleaved (or in other words, digested) by a protease when tropoelastin or a tropoelastin variant is folded in a functional conformation. A "functional conformation" is the conformation which imparts the elastin-like properties and macro-molecular binding properties to tropoelastin. The sub-sequences correspond to the amino acid sequences in the regions of tropoelastin which are susceptible to proteolysis.

Typically, the mutation involves altering at least one or two residues in the sub-sequence so as to reduce or eliminate susceptibility. More preferably, at least one sub-sequence is mutated. More preferably the tropoelastin is human tropoelastin.

It will be recognised that mutation to remove one or more sub-sequences which are capable of being digested by a serine protease is of particular benefit when the tropoelastin or tropoelastin variant is to be exposed to serum since the major proteolytic activity of serum for tropoelastin is serine protease activity.

In one embodiment of the first aspect of the invention, the sub-sequence is capable of being digested by a serine protease and has an amino acid sequence including the sequence RAAAG [aa 1–5 of SEQ ID No: 9], or an amino acid sequence selected from the group of sequences shown in SEQ ID NOS: 17 to 44. When the sub-sequence is an amino acid sequence selected from the group of sequences shown in SEQ ID NOS: 17 to 44, or has an amino acid sequence including RAAAG [aa 1–5 of SEQ ID No: 9], the sub-sequence is preferably mutated by replacing arginine in the sub-sequence with alanine. Preferably, the sub-sequence is capable of being digested by thrombin and has an amino acid sequence shown in SEQ ID NOS: 8 or 9. Preferably the sub-sequence is capable of being digested by plasmin and has an amino acid sequence shown in SEQ ID NOS: 11 or 12. More preferably, the sub-sequence is capable of being digested by kallikrein. Yet more preferably, the sub-sequence is capable of being digested by kallikrein and has an amino acid sequence shown in any one of SEQ ID NOS: 9 or 10.

The present inventor has noted that cleavage of SHEL and SHELδ26A with metalloproteinases leads to reproducible patterns with apparently preferred cleavage sites, evidenced using methods similar to those described here. Examples of metalloproteinases include gelatinases A and B, the 72 kD and 92 kD proteases, and matrix metallo elastase. Significantly SDS-PAGE indicates that cleavage is, at least in some obvious instances, different to the recognition sequences seen with serine proteases as described in Table 1. Using the 92 kDa metalloproteinase, a characteristic banding pattern was obtained with clear evidence of preferred, more intense bands. For example, using methods described herein for the serine proteases, N-terminal sequencing of an approximately 10 kDa band derived from SHEL revealed the sequence: LAAAKAAKYGAA [aa 594–604 of SEQ ID NO:4]. Its location in SHEL is illustrated in FIG. 2. Thus a preferred recognition site resides between A and L, which is N-terminally upstream of the identified sequence of this fragment. It will be recognised that mutation to the tropoelastin or a tropoelastin variant sequence to remove one or more sub-sequences which are digested by metalloproteinases is of particular benefit when the tropoelastin or tropoelastin variant is to be exposed to, for example, wound sites, locations of tissue damage and remodelling which can expose the tropoelastin or tropoelastin variant to metalloproteinases.

In another embodiment of the first aspect of the invention, the sub-sequence is capable of being digested by a metalloproteinase and has an amino acid sequence including the sequence ALAAA [aa 1–5 of SEQ ID NO:13], or an amino acid sequence selected from the group of sequences shown in SEQ ID NOS: 45 to 70. Preferably, the sub-sequence is capable of being digested by gelatinase A or B. Preferably the sub-sequence has the amino acid sequence shown in SEQ ID NO: 13. When the sub-sequence is an amino acid sequence selected from the group of sequences shown in SEQ ID NOS: 45 to 70, or has an amino acid sequence including ALAAA [aa 1–5 of SEQ ID NO:13], the sub-sequence is preferably mutated by replacing alanine at any position in the sub-sequence with another amino acid residue. More preferably, the alanine N-terminal to the leucine is mutated by replacing that alanine with another amino acid residue.

In a second aspect the present invention provides a reduced tropoelastin derivative exhibiting reduced or eliminated susceptibility to proteolysis in comparison with a corresponding tropoelastin or a corresponding tropoelastin variant, the reduced tropoelastin derivative characterised in that a sub-sequence of the corresponding tropoelastin or corresponding tropoelastin variant amino acid sequence is mutated in the reduced tropoelastin derivative to eliminate or reduce the susceptibility of the reduced tropoelastin derivative to proteolysis.

Typically at least one or two residues are mutated in the sub-sequence. More preferably, at least one sub-sequence is mutated. More preferably the tropoelastin is human tropoelastin.

In one embodiment of the second aspect of the invention, the mutated sub-sequence has reduced or eliminated susceptibility to digestion by a serine protease. Preferably the mutated sub-sequence includes the sequence RAAAG [aa 1–5 of SEQ ID NO:9], or is a sequence selected from the group of sequences shown in SEQ ID NOS: 17 to 44, provided that arginine in the sequence is replaced with alanine. Preferably the mutated sub-sequence has reduced or eliminated susceptibility to digestion by thrombin, and the mutated sub-sequence has the sequence shown in SEQ ID NOS: 8 or 9, provided that at least one amino acid residue in the sequence is mutated. Preferably the mutated sub-sequence has reduced or eliminated susceptibility to digestion by plasmin, and the mutated sub-sequence has the sequence shown in SEQ ID NOS: 11 or 12, provided that at least one amino acid residue in the sequence is mutated. More preferably, the mutated sub-sequence has reduced or eliminated susceptibility to digestion by kallikrein. Yet more preferably, the mutated sub-sequence has reduced or eliminated susceptibility to digestion by kallikrein and the mutated sub-sequence has the sequence shown in SEQ ID NOS: 9 or 10, provided that at least one amino acid residue in the sequence is mutated.

In another embodiment of the second aspect of the invention, the mutated sub-sequence has reduced or eliminated susceptibility to digestion by a metalloproteinase. Preferably the mutated sequence includes the sequence ALAAA [aa 1–5 of SEQ ID NO:13], or is a sequence selected from the group of sequences shown in SEQ ID NOS: 45 to 70, provided that alanine at any position in the sequence is replaced with any amino acid residue except alanine. More preferably, the mutated sub-sequence has reduced or eliminated susceptibility to digestion by gelatinase A or B. More preferably, the mutated sub-sequence has reduced or eliminated susceptibility to digestion by gelatinase B and the mutated sub-sequence has the sequence shown in SEQ ID NO: 13, provided that at least one amino acid residue in the sequence is mutated. More preferably, the alanine N-terminal to the leucine is mutated by replacing that alanine with another amino acid residue.

Reduced tropoelastin derivatives of the second aspect with mutations appropriate to their use environment can beneficially be used in vivo at sites where there is a risk of protease attack on tropoelastin or a variant of tropoelastin, such as in the presence of serum or wound exudate. For instance, the therapeutic use of cross-linked tropoelastin or a cross-linked tropoelastin variant in blood vessel walls would benefit since serum-induced degradation could be reduced. Further, certain modifications should reduce the need to use protease inhibitors during purification of the reduced tropoelastin derivative and result in greater amounts of full-length material if one or more susceptible regions are modified to minimise attack by endogenous host proteases.

In a third aspect the present invention provides a method of protecting a tropoelastin or a tropoelastin variant from degradation by serum or a protease selected from the group consisting of kallikrein, thrombin, trypsin and related serine proteases, including elastase, which method comprises mutating at least one sub-sequence in the tropoelastin or tropoelastin variant amino acid sequence to reduce or eliminate the susceptibility of the tropoelastin or tropoelastin variant to proteolysis. Preferably the tropoelastin is human tropoelastin. Preferably the protease is kallikrein.

In a fourth aspect the present invention provides a method of protecting a tropoelastin or a tropoelastin variant from degradation by proteolytic attack, which method comprises mutating at least one sub-sequence in the tropoelastin or tropoelastin variant amino acid sequence to reduce or eliminate the susceptibility of the tropoelastin or tropoelastin variant to proteolysis. In one embodiment the sub-sequence is digested by a metalloproteinase.

As described above, amino acid sequences of non-human tropoelastins have been determined, including the amino acid sequences of chick tropoelastin, bovine tropoelastin and rat tropoelastin (Bressan et al. 1987, Raju et al. 1987, Pierce et al. 1992). A comparison of these non-human tropoelastin amino acid sequences with tropoelastin reveals that particular regions of tropoelastin which are susceptible to proteolysis as identified in the present invention are conserved in these non-human tropoelastins. Therefore it is likely that these particular regions in the non-human tropoelastins will be susceptible to proteolysis.

The analysis of the sub-sequences described in Table 1 with non human tropoelastin or elastin sequences with the 'nr' database using 'tblastn' at the NCBI Blast facility (http://www.ncbi.nlm.nih.gov/BLAST) shows the following:

(i) human tropoelastin:

554 VPTGAGVKPKAPGVGGAF 607 [aa 145–162 of SEQ ID NO:4]

bovine tropoelastin, exon 14

373 VPTGAGVKPKAPGGGGAF 426 [SEQ ID NO: 75]

mouse tropoelastin mRNA complete cds

694 VPTGTGVKAKAPGGGGAF 747 [SEQ ID NO: 76]

bovine elastin a mRNA complete cds

545 VPTGAGVKPKAQVGAGAF 598 [SEQ ID NO: 77]

bovine elastin b mRNA complete cds

545 VPTGAGVKPKAQVGAGAF 598 bovine elastin c mRNA complete cds

545 VPTGAGVKPKAQVGAGAF 598 [SEQ ID NO: 77]

rat tropoelastin mRNA 3' end

646 VPTGTGVKAKVPGGGG 693 [SEQ ID NO: 78]

chicken tropoelastin mRNA complete cds

572 VPTGTGIKAKGPGAG 616 [SEQ ID NO: 79]

(ii) human tropoelastin:

1664 KVAAKAQLRAAAGLGAG 1714 [aa 509–525 of SEQ ID NO:4]

rat tropoelastin mRNA 3' end

1837 KAAAKAQYRAAAGLGAG 1887 [SEQ ID NO: 80]

mouse tropoelastin mRNA complete cds

1795 KAAAKAQYRAAAGLGAG 1845 [SEQ ID NO: 80]

bovine elastin a mRNA complete cds

1649 KAAAKAQFRAAAGLPAG 1699 [SEQ ID NO: 81]

bovine elastin b mRNA complete cds

1607 KAAAKAQFRAAAGLPAG 1657 [SEQ ID NO: 81]

bovine elastin c mRNA complete cds

1547 KAAAKAQFRAAAGLPAG 1597 [SEQ ID NO: 81]

which demonstrates that the sub-sequences identified in Table 1 are highly homologous with non human tropoelastin or elastin sequences, supporting the proposition that taking account of sequence differences the methods of the invention can be applied to different tropoelastin species.

This analysis also demonstrates a consensus sequence: AKAAAKAQN$_0$R/AAAGLN$_1$AGN$_2$P [SEQ ID NO: 82] wherein N$_0$ is an aromatic or hydrophobic residue;
N$_1$ is P or G; and
N$_2$ is a hydrophobic residue for the site in tropoelastin which is cleaved by kallikrein and thrombin. An amino acid sequence which is within the definition of this consensus sequence may be mutated in accordance with the methods of the invention to provide the derivatives of the invention which have, for example, reduced or eliminated susceptibility to proteolysis.

In the human tropoelastin splice form described in more detail herein and shown in SEQ ID NO:4, the cleavage in serum occurs between residues 515 and 516; 564 and 565; 441 and 442; 503 and 504. Thus for this splice form the alteration to the sequence to influence serine protease susceptibility preferably involves modification of at least one of residues 515, 516, 564, 565, 441, 442, 503, 504, 564 and 565.

Alterations to reduce susceptibility to protease attack can be considered to involve removal or modification of the recognition site. An example of this modification is the replacement of lysine or arginine by an amino acid residue that is not positively charged. An example of this approach is the use of leucine to replace arginine in the sequence R/AAAGLG [SEQ ID NO:9] of Table 1 using common methods of mutagenesis such as those available commercially in kit form.

Reduced tropoelastin derivatives of the invention include:
SHELδ26a (shown in FIG. 3; SEQ ID NO: 5);
SHELδmod (shown in FIG. 4; SEQ ID NO:6);
sequences shown in SEQ ID NOS: 71 to 74.

As the inventor has determined the regions of tropoelastin which are susceptible to proteolysis, tropoelastin can be modified by inserting a sequence which corresponds to an amino acid sequence in a susceptible region of tropoelastin, into the tropoelastin amino acid sequence, thus providing an enhanced tropoelastin derivative which has enhanced protease susceptibility under particular conditions as compared with the protease susceptibility of tropoelastin under the same conditions.

Thus, in the specification and claims, "enhanced tropoelastin derivative" means a molecule produced by inserting a sequence which corresponds to an amino acid sequence in a susceptible region of tropoelastin, into the tropoelastin amino acid sequence, which molecule is folded in a functional conformation. The insertion of the amino acid sequence which corresponds to the amino acid sequence of a susceptible region causes enhanced protease susceptibility. Enhanced tropoelastin derivatives may correspond to full length tropoelastin molecules, single domains of tropoelastin which are encoded by specific exons of the tropoelastin gene or peptides which are encoded by all or part of two neighbouring exons of the tropoelastin gene.

Insertion of the amino acid sequence into tropoelastin, may occur by, for example, splicing a peptide which has an amino acid sequence which corresponds to a susceptible region in tropoelastin, into tropoelastin. Thus, enhanced tropoelastin derivatives may be produced by mutation events including a mutation in a nucleotide sequence which causes an insertion of a peptide in the tropoelastin amino acid sequence wherein the inserted peptide corresponds to an amino acid sequence in a susceptible region of tropoelastin.

Alternatively, insertion of the amino acid sequence into tropoelastin may occur by modifying an amino acid sequence in a region of tropoelastin, by residue insertion, substitution or deletion, so as to generate an amino acid sequence in that region of tropoelastin which is the same as an amino acid sequence in a susceptible region of tropoelastin. Thus, enhanced tropoelastin derivatives may be produced by mutation events including a mutation in a nucleotide sequence which causes residue insertion, substitution or deletion in a region of tropoelastin, wherein the mutation events produce at the region, an amino acid sequence which corresponds to a susceptible region of tropoelastin.

Enhanced tropoelastin derivatives which have an inserted amino acid sequence in accordance with either of the above, may be mutated further by residue insertion, substitution or deletion, or further amino acid sequence insertion. The further mutations may or may not alter the susceptibility of the enhanced tropoelastin derivative to proteases. Enhanced tropoelastin derivatives which contain these mutations may be produced synthetically.

Enhanced tropoelastin derivatives can be produced by modification of tropoelastin variant amino acid sequences, in regions of tropoelastin which are susceptible to protease digestion.

Thus, enhanced tropoelastin derivatives may be produced by mutation of a tropoelastin variant amino acid sequence including a mutation in a nucleotide sequence which causes an insertion of a peptide in the tropoelastin variant amino acid sequence wherein the inserted peptide corresponds to an amino acid sequence in a susceptible region of tropoelastin.

Alternatively, enhanced tropoelastin derivatives may be produced by mutation of a tropoelastin variant amino acid sequence including a mutation in a nucleotide sequence which causes residue insertion, substitution or deletion in a region of a tropoelastin variant amino acid sequence, wherein the mutation events produce at the region, an amino acid sequence which corresponds to a susceptible region of tropoelastin.

Enhanced tropoelastin derivatives which have an inserted amino acid sequence in accordance with either of the above, may be mutated further by residue insertion, substitution or deletion, or further amino acid sequence insertion in the tropoelastin variant amino acid sequence. The further mutations may or may not alter the susceptibility of the enhanced tropoelastin derivative to proteases. Enhanced tropoelastin derivatives which contain these mutations may be produced synthetically or by recombinant methods.

As described above, the tropoelastin amino acid sequence is known to be translated in various mRNA splice forms in humans and non-human animals. Further the comparison of human and non-human tropoelastin amino acid sequences reveals amino acid homology between tropoelastin amino acid sequences. Thus, these various isoforms of human and non-human tropoelastin and the mRNA splice forms encoding them can be modified to provide the enhanced tropoelastin derivatives of the invention.

In a fifth aspect the invention provides a method for enhancing the susceptibility of a tropoelastin or tropoelastin variant amino acid sequence to proteolysis, which method comprises inserting a sub-sequence into a tropoelastin or tropoelastin variant amino acid sequence to enhance the susceptibility of the tropoelastin or tropoelastin variant to proteolysis. As described above, in the specification and claims, a "sub-sequence" means a sequence which is capable of being cleaved by a protease when tropoelastin or a tropoelastin variant is folded in a functional conformation. The sub-sequences correspond to the amino acid sequences in the regions of tropoelastin which are susceptible to proteolysis. Typically, at least one sub-sequence is inserted into the tropoelastin or tropoelastin variant amino acid sequence. Preferably the tropoelastin is human tropoelastin.

In one embodiment of the fifth aspect of the invention, the inserted sub-sequence is capable of being digested by a serine protease and has an amino acid sequence including the sequence RAAAG [aa 1–5 of SEQ ID NO: 9], or an amino acid sequence selected from the group of sequences shown in SEQ ID NOS: 17 to 44. Preferably, the subsequence is capable of being digested by thrombin and has an amino acid sequence shown in SEQ ID NOS: 8 or 9. Preferably the sub-sequence is capable of being digested by plasmin and has an amino acid sequence shown in SEQ ID NOS: 11 or 12. More preferably, the sub-sequence is capable of being digested by kallikrein. Yet more preferably, the sub-sequence is capable of being digested by kallikrein and has an amino acid sequence shown in SEQ ID NOS: 9 or 10.

In another embodiment of the fifth aspect of the invention, the sub-sequence is capable of being digested by a metalloproteinase and has an amino acid sequence including the sequence: ALAAA [aa 1–5 of SEQ ID NO:13], or an amino acid sequence selected from the group of sequences shown in SEQ ID NOS: 45 to 70. Preferably, the sub-sequence is capable of being digested by gelatinase A or B. Preferably the sub-sequence has the amino acid sequence shown in SEQ ID NO: 13.

In a sixth aspect the invention provides an enhanced tropoelastin derivative exhibiting enhanced susceptibility to proteolysis in comparison with a corresponding tropoelastin or tropoelastin variant, the enhanced tropoelastin derivative characterised in that a sub-sequence is inserted in the amino acid sequence of the enhanced tropoelastin derivative to enhance the susceptibility of the enhanced tropoelastin derivative to proteolysis. Typically, at least one sub-sequence is inserted into the tropoelastin or tropoelastin variant amino acid sequence. Preferably the tropoelastin is human tropoelastin.

In one embodiment of the sixth aspect of the invention, the inserted sub-sequence is capable of being digested by a serine protease. Preferably the inserted sub-sequence includes the sequence RAAAG [aa 1–5 of SEQ ID NO:9], or is a sequence selected from the group of sequences shown in SEQ ID NOS: 17 to 44. Preferably the inserted subsequence is capable of being digested by thrombin, and the inserted sub-sequence has the sequence shown in SEQ ID NOS: 8 or 9. Preferably the inserted sub-sequence is capable of being digested by plasmin, and the inserted sub-sequence has the sequence shown in SEQ ID NOS: 11 or 12. More preferably, the inserted sub-sequence is capable of being digested by kallikrein. Yet more preferably, the inserted sub-sequence is capable of being digested by kallikrein and the inserted sub-sequence has the sequence shown in SEQ ID NOS: 9 or 10.

In another embodiment of the sixth aspect of the invention, the inserted sub-sequence is capable of being digested by a metalloproteinase. Preferably the inserted sequence includes the sequence: ALAAA [aa 1–5 of SEQ ID NO:13], or is a sequence selected from the group of sequences shown in SEQ ID NOS: 45 to 70. More preferably, the inserted sub-sequence is capable of being digested by gelatinase A or B. More preferably, the inserted sub-sequence is capable of being digested by gelatinase B and the inserted sub-sequence has the sequence shown in SEQ ID NO: 13.

The enhanced tropoelastin derivative of the sixth aspect can beneficially be used in vivo at sites where it is desirable to augment protease attack on the derivative. Suitable molecules for manipulation include human tropoelastin molecules. In this case, the modified tropoelastin will be of use in situations in which it is desirable to have the tropoelastin or tropoelastin variant degrade rapidly. Such situations include revealing and/or release of peptides with desirable properties, to accelerate tissue repair.

As the inventor has determined the regions of tropoelastin which are susceptible to proteolysis, the susceptibility of a polypeptide to proteolysis can be modified by inserting a sequence which corresponds to an amino acid sequence in a susceptible region of tropoelastin, into the polypeptide amino acid sequence, thus providing a polypeptide derivative which has enhanced protease susceptibility under particular conditions compared with the same polypeptide which does not contain the said inserted sequence, (the corresponding polypeptide) under the same conditions.

In the specification and claims "polypeptide derivative" means a polypeptide produced by inserting a sequence which corresponds to an amino acid sequence in a susceptible region of tropoelastin, into the polypeptide sequence. The insertion of the amino acid sequence which corresponds to the amino acid sequence of a susceptible region of tropoelastin into the polypeptide sequence, causes the enhanced protease susceptibility of the polypeptide derivative.

Insertion of the amino acid sequence into the polypeptide sequence may occur by, for example, splicing a peptide which has an amino acid sequence which corresponds to a susceptible region in tropoelastin, into the polypeptide. Thus polypeptide derivatives may be produced by mutation events including a mutation in a nucleotide sequence which causes an insertion of a peptide in the polypeptide amino acid sequence wherein the inserted peptide corresponds to an amino acid sequence in a susceptible region of tropoelastin.

Alternatively, insertion of the amino acid sequence into the polypeptide sequence may occur by modifying an amino acid sequence in the region of the polypeptide, by residue insertion, substitution or deletion, so as to generate an amino acid sequence in that region of the polypeptide which is the same as an amino acid sequence in a susceptible region of tropoelastin. Thus, polypeptide derivatives may be produced by mutation events including a mutation in a nucleotide sequence which causes residue insertion, substitution or deletion in a region of the polypeptide, wherein the mutation events produce at the region, an amino acid sequence which corresponds to a susceptible region of tropoelastin.

Polypeptide derivatives which contain these mutations may be produced synthetically or by recombinant DNA methods.

Thus in a seventh aspect the invention provides a method for enhancing the susceptibility of a polypeptide amino acid sequence to proteolysis, which method comprises inserting an amino acid sequence which corresponds to an amino acid sequence in a susceptible region of tropoelastin into the polypeptide amino acid sequence to enhance the susceptibility of the polypeptide to proteolysis. Typically at least one amino acid sequence corresponding to an amino acid sequence in a susceptible region of tropoelastin is inserted into the polypeptide amino acid sequence.

In one embodiment the inserted sequence is capable of being digested by a protease selected from the group consisting of thrombin, kallikrein, trypsin and related serine proteases including elastase. In another embodiment, the inserted sequence is digested by metalloproteinase.

In an eighth aspect, the invention provides a polypeptide derivative exhibiting enhanced susceptibility to proteolysis in comparison with a corresponding polypeptide, the polypeptide derivative characterised in that an amino acid sequence which corresponds to an amino acid sequence in a susceptible region of tropoelastin is inserted into the polypeptide amino acid sequence to enhance the susceptibility of the polypeptide to proteolysis. Typically at least one sequence corresponding to an amino acid sequence in a susceptible region of tropoelastin is inserted into the polypeptide amino acid sequence.

In one embodiment, the inserted sequence is capable of being digested by a serine protease. Preferably the serine protease is kallikrein. In another embodiment the inserted sequence may be digested by a metalloproteinase.

As the inventor has determined the regions of tropoelastin which are susceptible to proteolysis, these regions can be used to direct the specific release of peptide domains from reduced or enhanced tropoelastin derivatives of the second and sixth aspects of the invention or the specific release of peptides from the polypeptide derivatives of the eighth aspect of the invention. Typically, amino acid sequences which correspond to the susceptible regions of tropoelastin are inserted between the derivative and the peptide domain thus providing a chimeric derivative which can be digested at the susceptible region by a specific protease to release the peptide domain from the derivative.

In the specification and claims, "chimeric derivative" means a molecule produced by linking a derivative selected from the group consisting of a reduced tropoelastin derivative, enhanced tropoelastin derivative and a polypeptide derivative, with a peptide domain via an amino acid sequence which corresponds to an amino acid sequence in a susceptible region of tropoelastin. The amino acid sequence which corresponds to the amino acid sequence of a susceptible region of tropoelastin causes the release of the peptide domain from the derivative when the chimeric derivative is digested by a specific protease.

Chimeric derivatives may be produced by recombinant DNA techniques, including for example the construction of a nucleotide sequence which encodes the derivative, the susceptible region and the peptide domain in a single open reading frame. The chimeric derivatives may alternatively be produced synthetically or by recombinant DNA methods.

Thus in a ninth aspect, the invention provides a method for producing a chimeric derivative which method comprises linking a derivative selected from the group consisting of a reduced tropoelastin derivative, enhanced tropoelastin derivative and a polypeptide derivative, with a peptide domain via an amino acid sequence which corresponds to an amino acid sequence in a susceptible region of tropoelastin.

In one embodiment, the amino acid sequence which corresponds to an amino acid sequence in a susceptible region of tropoelastin sequence may be digested by a serine protease. Preferably the serine protease is kallikrein. In another embodiment the sequence may be digested by a metalloproteinase.

In a tenth aspect, the invention provides a chimeric derivative which comprises a derivative selected from the group consisting of a reduced tropoelastin derivative, enhanced tropoelastin derivative and a polypeptide derivative, which is linked with a peptide domain via an amino acid sequence which corresponds to an amino acid sequence in a susceptible region of tropoelastin.

In one embodiment the amino acid sequence which corresponds to an amino acid sequence in a susceptible region of tropoelastin sequence may be digested by a serine protease. Preferably the serine protease is kallikrein. In another embodiment the sequence may be digested with metalloproteinase.

The chimeric derivatives of the invention are useful where the peptide domain has a particular biological function, including for example chemotaxis, cell proliferation or cell activation. These biological functions are effected by digestion of the chimeric derivative at the sub-sequence by a particular protease so as to release the peptide domain from the derivative domain.

The mutations in accordance with this invention may be generated by conventional site-directed or random mutagenesis. Oligonucleotide-directed mutagenesis is a further option. This method comprises:
1. synthesis of an oligonucleotide with a sequence that contains the desired nucleotide substitution (mutation);
2. hybridising the oligonucleotide to a template comprising a structural sequence encoding tropoelastin; and
3. using a DNA polymerase to extend the oligonucleotide as a primer.

Another approach which is particularly suited to situations where a synthetic polynucleotide encoding the tropoelastin is prepared from oligonucleotide blocks bounded by restriction sites, is cassette mutagenesis where entire restriction fragments are replaced.

As the inventor has identified regions of tropoelastin which are susceptible to proteolysis, it is possible to use the amino acid sequences in the susceptible regions to prepare protease inhibitor molecules which are also known as peptidomimetic molecules. In the specification and claims, "peptidomimetic molecules" means molecules which imitate a region of tropoelastin which is susceptible to proteolysis, and which therefore compete with the susceptible region for the catalytic domain in a protease. Typically the peptidomimetic molecules are peptides or peptide-like.

The peptidomimetic molecules of the invention may be structurally similar to peptides. They may include an amino acid sequence of a tropoelastin or of a variant of tropoelastin which is or includes a proteolytic site. The peptidomimetic molecules of the invention may include amino acid residues which are modified at one or more chemical groups and may be linked by non-peptide bonds. These molecules can be used in situations in which it is desirable to prevent the action of the relevant proteases.

In an eleventh aspect the present invention provides a peptide or a peptidomimetic molecule including all or part of a peptide selected from the group consisting of KAPGVGGAF [SEQ ID NO:8], RAAAGLG [SEQ ID NO: 9], RSLSPELREGD [SEQ ID NO: 10], KAAQFGLVPGV [SEQ ID NO: 11], KSAAKVAAKAQLRAA [aa 505–519 of SEQ ID NO:4], RSLSPELRE [aa 1–9 of SEQ ID NO: 4] and LAAAKAAKYGAA [aa 2–13 of SEQ ID NO:13].

The peptides of this aspect of the invention may be short peptides consisting of all or part of a sequence selected from the group consisting of KAPGVGGAF [SEQ ID NO:8], RAAAGLG [SEQ ID NO: 9], RSLSPELREGD [SEQ ID NO: 10], KAAQFGLVPGV [SEQ ID NO: 11], KSAAKVAAKAQLRAA [aa 505–519 of SEQ ID NO:4], RSLSPELRE [aa 1–9 of SEQ ID NO: 4] and LAAAKAAKYGAA [aa 2–13 of SEQ ID NO:13] each in combination with upstream sequence to generate a peptide typically of the order of 15 residues although it will be understood that in some cases smaller peptides could be used and frequently larger sequences could be used. The peptides can be larger molecules containing one or more of these sequences. In addition structural analogues of these peptides are included within the scope of peptidomimetic molecules of the invention, and include for instance molecules containing modified amino acid residues.

A preferred molecule is one in which the natural cleavage site would typically be located about the centre of the peptide or peptidomimetic molecule. An example peptide is H-Ala-Ala-Lys-Ala-Gln-Leu-Arg-Ala-Ala-Ala-Gly-Leu-Gly-Ala-OH [aa 511–524 of SEQ ID NO; 4] which is based on the sequence RAAAGLGA [SEQ ID NO:9], in its context within the sequence of tropoelastin(s). A peptidomimetic form of this molecule is H-Ala-Ala-Lys-Ala-Gln-Leu-Arg-R-Ala-Ala-Ala-Gly-Leu-Gly-Ala-OH (where R=a reduced peptide bond) [SEQ ID NO:83]. Also preferred are the following retro-inverso pseudo peptides: H-D-Ala-Gly-D-Leu-Gly-D-Ala-D-Ala-D-Ala-(reduced)-D-Arg-D-Leu-D-Gln-D-Ala-D-Lys-D-Ala-D-Ala-OH [SEQ ID NO:84] and H-D-Ala-Gly-D-Leu-Gly-D-Ala-D-Ala-D-Ala-D-Arg-D-Leu-D-Gln-D-Ala-D-Lys-D-Ala-D-Ala-OH [SEQ ID NO: 85]. Preferably these peptides are coupled to a substrate through the N- or C-terminus.

Also preferred are the following peptides: H-Val-Pro-Gly-Ala-Leu-Ala-Ala-Ala-OH [aa 557–564 of SEQ ID NO:5]; H-Val-Pro-Gly-Ala-(reduced)-Leu-Ala-Ala-Ala-OH [SEQ ID NO: 86] and the retro-inverso pseudopeptides: H-D-Ala-D-Ala-D-Ala-D-Leu-(reduced)-D-Ala-Gly-D-Pro-D-Val-OH [SEQ ID NO: 87] and H-D-Ala-D-Ala-D-Ala-D-Leu-D-Ala-Gly-D-Pro-D-Val-OH [SEQ ID NO: 88]. Preferably these peptides are coupled to a substrate through the N- or C-terminus.

A further category of molecules contain one or more attached reactive groups for the covalent modification of an interacting protease leading to further inhibition of activity of the protease. The invention contemplates the use of endogenous or exogenous lysyl oxidase for attaching reactive groups. It is also recognised that there is a plethora of chemically reactive groups available as biochemical reagents, which are often utilised in the construction of chemical crosslinkers. The invention contemplates the use of endogenous or exogenous lysyl oxidase for attaching reactive groups. A subset of these may be found in the Pierce Product Catalog (1997) Chapter 7 pp 133 to 154. The reactive group is placed at the ends or internal to the molecule to provide a proximity to the reacting entity.

The peptides and peptidomimetic molecules of the invention are useful in a number of different environments including in the purification of tropoelastin, as a pharmaceutical agent which can be provided in an inhalant form for protecting lung tissue from damage related to elastolytic protease attack on elastin (a major cause of lung damage in smokers) and in any other environment in which competitive inhibition of protease active sites recognising these peptides is desirable.

The peptides and peptidomimetic molecules of the invention are also useful in inhibiting or controlling the local growth and metastases of cancer. In particular, the inventors recognise that the peptides and peptidomimetic molecules of the invention will be useful in competing with endogengous tropoelastin for proteases which are secreted by neoplastic cells. The secretion of these proteases is typically associated with the local growth or metastases of cancer. Thus the capacity of the peptide or peptidomimetic molecules of the invention to compete with endogenous tropoelation for the proteases may inhibit or reduce the local growth or metastasis of the cancer. In this application, the peptides or peptidomimetic molecules of the invention may be coupled to a substrate.

In a twelfth aspect the present invention provides a method for enhancing the purification of a tropoelastin or a tropoelastin variant which method comprises including at least one peptide or peptidomimetic molecule of the eleventh aspect of the invention in the crude tropoelastin or tropoelastin variant preparation which is being subjected to purification.

In a thirteenth aspect the present invention provides a pharmaceutical composition comprising a derivative selected from the group consisting of a reduced tropoelastin derivative, an enhanced tropoelastin derivative, a polypeptide derivative and a chimeric derivative, or a peptide or peptidomimetic molecule of the invention together with a pharmaceutically acceptable carrier or diluent. Formulations of the derivatives or peptides or peptidomimetic molecules of the present invention are prepared in accordance with standard pharmaceutical techniques. Preferred formulations in accordance with the invention include inhalant formulations, incorporation into emulsions designed for localised use, attachment to surfaces such as a stent and injectable formulations. In addition the present inventor recognises that the compositions of the invention can be adapted for use in situations in which it is desirable to limit protease activity such as that leading to clot formation.

In an fourteenth aspect the present invention provides a nucleotide sequence encoding a derivative selected from the group consisting of a reduced tropoelastin derivative, an enhanced tropoelastin derivative, a polypeptide derivative and a chimeric derivative or a peptide or peptidomimetic molecule of the invention.

The nucleotide may be provided as a recombinant DNA molecule including vector DNA. Polynucleotides can be prepared using a combination of synthetic and cDNA techniques to form hybrid modified polynucleotide molecules. These molecules also fall within the scope of this invention.

Vectors useful in this invention include plasmids, phages and phagemids. The synthetic polynucleotides of the present invention can also be used in integrative expression systems or lytic or comparable expression systems.

Suitable vectors will generally contain origins of replication and control sequences which are derived from species compatible with the intended expression host. Typically these vectors include a promoter located upstream from the polynucleotide, together with a ribosome binding site if intended for prokaryotic expression, and a phenotypic selection gene such as one conferring antibiotic resistance or supplying an auxotrophic requirement. For production vectors, vectors which provide for enhanced stability through partitioning may be chosen. Where integrative vectors are used it is not necessary for the vector to have an origin of replication. Lytic and other comparable expression systems do not need to have those functions required for maintenance of vectors in hosts.

For *E. coli* typical vectors include pBR322, pBluescript II SK+, pGEX-2T, pTrc99A, pET series vectors, particularly pET3a and pET3d, (Studier et al., 1990) and derivatives of these vectors.

In a fifteenth aspect the present invention provides a cell containing a nucleotide sequence of the fourteenth aspect of the invention.

A preferred expression system is an *E. coli* expression system. However, the invention includes within its scope the use of other hosts capable of expressing protein from the polynucleotides designed for use in *E. coli* as well as to the use of synthetic polynucleotides suitable for use in other expression systems such as other microbial expression systems. These other expression systems include yeast, and bacterial expression systems, insect cell expression systems, and expression systems involving other eukaryotic cell lines or whole organisms.

Examples of *E. coli* hosts include *E. coli* B strain derivatives (Studier et al, 1990), NM522 (Gough and Murray, 1983) and XL1-Blue (Bullock et al, 1987).

In a sixteenth aspect the present invention provides an expression product of a cell of the fifteenth aspect of the invention encoded by a nucleotide sequence of the fourteenth aspect of the invention.

The expression products of the invention may be fused expression products which include all or part of a protein encoded by the vector in peptide linkage with the expression product. They may also include, for example, an N-terminal methionine or other additional residues which do not permanently impair the elastic properties of the product.

Typically the fusion is to the N-terminus of the desired expression product. An example of a suitable protein is glutathione S-transferase (Smith and Johnson 1988). The fused protein sequence may be chosen in order to cause the expression product to be secreted or expressed as a cell surface protein to simplify purification or expressed as a cytoplasmic protein.

The expressed fusion products may subsequently be treated to remove the fused protein sequences to provide free modified tropoelastin. Treatment is typically through protease treatment, or in the case of secretion removal is effected by endogenous host secretion machinery. An example of this is secretion by yeasts, including but not limited to *S. cerevisae* and *S. pombe*.

Non-fused systems include the introduction of or use of a pre-existing methionine codon. An example of this is the use of pET3a and pET3d in *E. coli*.

According to a seventeenth aspect of the present invention there is provided a process for the production of an expression product of the sixteenth aspect comprising:

providing a cell of the fifteenth aspect; culturing it under conditions suitable for the expression of the product of the sixteenth aspect; and collecting the expression product.

In a eighteenth aspect the present invention provides an implant formed from one or more derivatives selected from the group consisting of a reduced tropoelastin derivative, an enhanced tropoelastin derivative, a polypeptide derivative and a chimeric derivative. Where the derivative has reduced proteolytic susceptibility the implant will be intended to be maintained in situ over a considerable period of time whereas when the derivative has enhanced proteolytic susceptibility the implant will be intended to be maintained in situ over a short period of time and indeed the rapid dissolution of the implant will be desired such as where it is desired that the implant is replaced by endogenous connective tissue.

Tropoelastin derivatives (ie reduced tropoelastin derivatives and enhanced tropoelastin derivatives) of the invention can be cross-linked to form elastin or elastin-like material or can be cross-linked in conjunction with other biological or synthetic molecules to form a composite material. The cross-linking of the tropoelastin derivative can be achieved by chemical oxidation of lysine side chains using processes such as ruthenium tetroxide mediated oxidation and quinone mediated oxidation, or by using bifunctional chemical cross-linking agents such as dithiobis (succinimidylpropionate), dimethyl adipimidate or dimethyl pimelimidate and those within heterologous sites such as agents that contain UV activated cross-linking domain(s). Another alternative is the cross-linking of lysine and glutamic acid side chains.

The tropoelastin derivatives (ie reduced tropoelastin derivatives and enhanced tropoelastin derivatives) may also be enzymatically cross-linked by methods including lysyl oxidase mediated oxidation or be cross-linked using gamma irradiation. The implants are formed into the required shape by cross-linking the tropoelastin derivative in a mould which conforms to the desired shape of the implant. Where the implant is required to be used in sheet form the derivative can be cross-linked on a flat surface. Relevant methodologies are described in, for example, U.S. Pat. No. 4,474,851 and U.S. Pat. No. 5,250,516. The elastomeric materials may be exclusively prepared from one or more derivatives or may be composites prepared from one or more derivatives together with other materials.

BEST METHOD OF PERFORMING THE INVENTION

The recombinant and synthetic procedures used are described in standard texts such as Sambrook et al (1989).

Purification of the tropoelastin derivatives and expression products of the invention is also performed using standard techniques with the actual sequence of steps in each instance being governed by the environment from which the molecule is to be purified. By way of example, reference is made to the purification scheme disclosed in PCT/AU93/00655.

Formulations in accordance with the invention are formulated in accordance with standard techniques.

The amount of tropoelastin derivative or peptidomimetic molecule that may be combined with a carrier or diluent to produce a single dosage form will vary depending on the situation in which the formulation is to be used and the particular mode of administration.

It will be understood also that specific doses for any particular host may be influenced by factors such as the age, sex, weight and general health of the host as well as the particular characteristics of the modified tropoelastin being used, and how it is administered.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent. Among the acceptable vehicles or solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid and organic solvents find use in the preparation of injectables.

Routes of administration, dosages to be administered as well as frequency of administration are all factors which can be optimised using ordinary skill in the art.

In addition, the derivatives and expression products may be prepared as topical preparations for instance as anti-wrinkle and hand lotions using standard techniques for the preparation of such formulations.

They also may be prepared in aerosol form for, for instance, administration to a patient's lungs, or in the form of surgical implants, foods or industrial products by standard techniques.

EXAMPLES

Materials and Methods

Reagents

Hirudin, PMSF, human thrombin, human plasma kallikrein, human plasmin and human leukocyte elastase (HLE) were obtained from Sigma. Bovine trypsin and Pefabloc SC were from Boehringer-Mannheim and Pefabloc PK was from Pentapharm, Switzerland. Gelatinase A (72 kDa gelatinase) and gelatinase B (92 kDa gelatinase) were obtained from Boehringer Mannheim Roche Diagnostics.

SHEL was obtained by the method described in WO94/14958.

SHELδ26A can be derived from SHEL by removing the synthetic coding sequence corresponding to exon 26A. A comparison of the sequence of SHEL with that of SHELδ26A is provided at FIG. 3. Its protein product is apparently identical to a naturally made human splice form of tropoelastin.

The Transformer Mutagenesis Kit (Clontech USA) was used with pSHELF (described in WO94/14958) in accordance with the supplied protocol to remove DNA corresponding to exon 26A. The sequence of the mutagenic primer used (manufactured by Beckman Australia) was:

5'CGG GTT TCG GTG CTG TTC CGG GCG CGC TGG 3' [SEQ ID NO: 89] which flanked either side of exon 26A by 15 bp resulting in its precise deletion. A second selection primer, which mutates a unique restriction site to another restriction site is normally used in the protocol but was not used in this case since deletion of exon 26A also resulted in the deletion of a unique restriction site, PmlI. This enzyme was therefore used to digest the mutation reaction to linearise any unmutated parental plasmid and consequently to enrich for mutant plasmid in accordance with the manufacturer's instructions. The reaction mixture was used to transfom competent BMH17–18 mutS $E.$ $coli$ defective in mismatch repair, by electroporation which was performed using a Gene Pulser apparatus (BioRad USA) according to a protocol supplied by the manufacturer. Electrocompetent cells were made according to standard protocol supplied by Clontech. Competent cells were stored in aliquots at −80° C. After electroporation cells were grown for one hour at 37° C. at 280 rpm in 1 ml LB. The entire entire transformed culture was grown overnight in 5 ml LB+ampicillin. Mixed plasmid DNA containing both mutated and parental plasmids was isolated from the culture using the Qiagen Spin Plasmid® isolation kit and the plasmid DNA was digested with PmlI to linearise the parental plasmid. The plasmid DNA now enriched for mutated plasmid was used to transform $E.$ $coli$ HMS174 by electroporation as described above and transformants selected on LB plates containing 75 µg/ml ampicillin.

Colonies were grown overnight and plasmid mini-preparations performed in which a single colony was inoculated into 3 ml LB+ampicillin media in 10 ml screw-topped tubes and grown overnight with shaking at 37° C. Plasmids were extracted following the alkaline lysis protocol from Sambrook et al (1989). For HMS174 two extractions with phenol/chloroform/isoamyl alcohol were performed. Constructs were screened using PmlI and those which were insensitive to digestion were further screened by KpnI/PstI double digestion. Candidate clones were sequenced (as described herein) manually using 6F (5' GGG TGT TGG CGT TGC ACC AG 3', SEQ ID NO: 90) and 7R (5' TGC ACC TAC AAC ACC GCC CG 3', SEQ ID NO: 91)

primers to confirm sequence integrity either side of the deleted region.

Automated sequencing was conducted (using either the Sequi-Net™ program (Department of Biochemistry Colorado State University USA) or by the SUPAMAC™ program (Sydney University and Prince Alfred Hospital Macromolecular Analysis Centre). DNA was applied after purification by either cesium chloride gradient or Qiagen Tip 20 (Qiagen GmbH Germany) and sequenced using the same primers as for manual sequencing.) using primers 1R (5' TGC CTT TGC CGG TTT GTA CG 3', SEQ ID NO:92)

3F (5' TCC AGG TGG CTA CGG TCT GC 3', SEQ ID NO: 93)

3R (5' GAG TAC CTA CGC CTG CGA TAC 3', SEQ ID NO: 94)

5R (5' GGA GTA CCA ACG CCG TAC TT 3', SEQ ID NO: 95)

6F (5' GGG TGT TGG CGT TGC ACC AG 3', SEQ ID NO: 96)

7R (5' TGC ACC TAC AAC ACC GCC CG 3', SEQ ID NO: 97)

pETforward (5' GCA CTC ACT ATA GGG AGA CC 3', SEQ ID NO: 98)

pETreverse (5' GCC AAC TCA GCT TCC TTT CG 3', SEQ ID NO: 99) was performed to verify the rest of the sequence. A number of undesired mutations were discovered necessitating further manipulation to the DNA. The mutated DNA is named pSHELFδmod.

Figure 15:
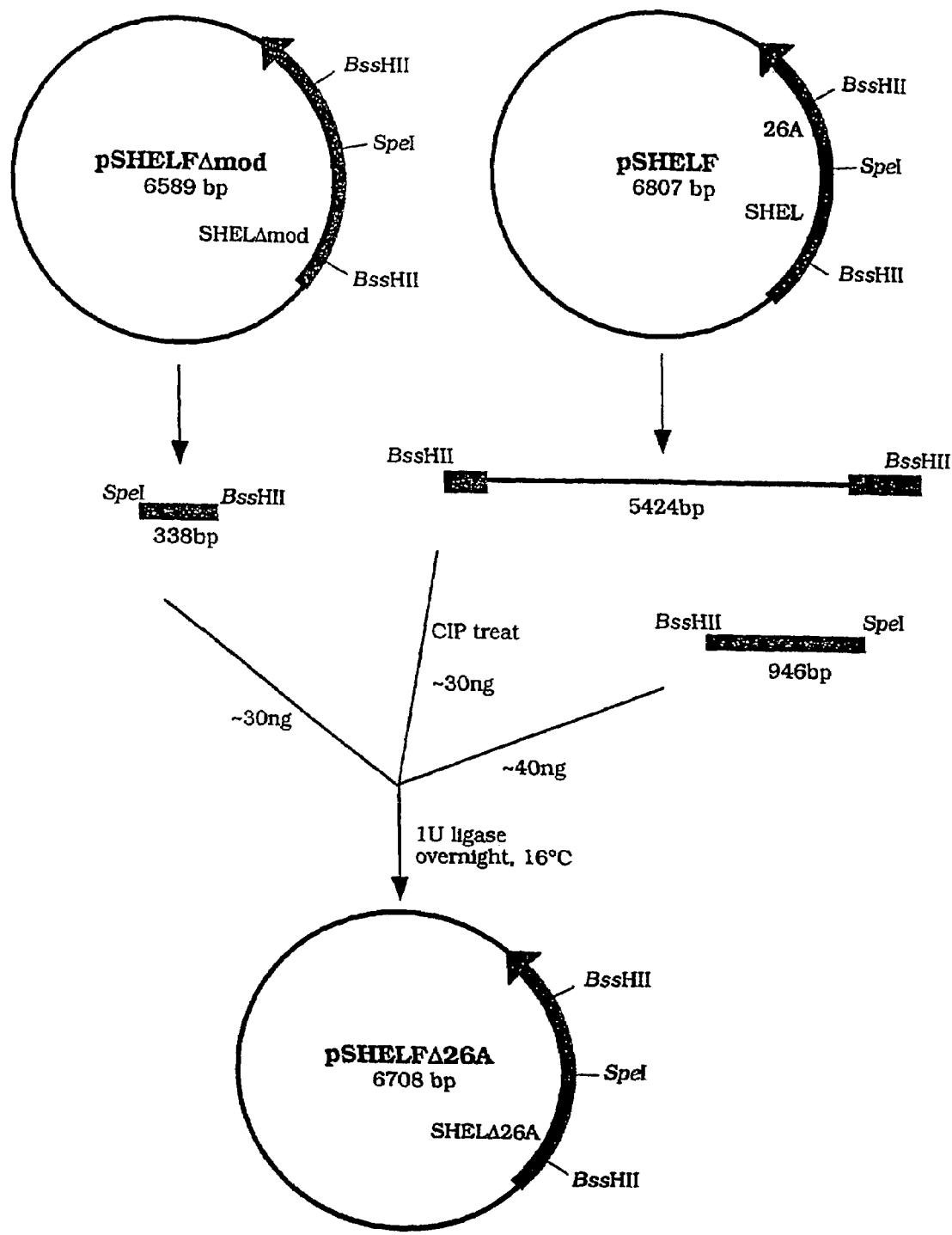
FIG. 15 shows the construction scheme for pSHELFδ26A. pSHELF and the aberrant pSHELFδmod were both digested with SpeI and BssHII. BssHII cuts both plasmids twice and SpeI once resulting in three fragments. The 5424 and 946 bp fragments from pSHELF and the small 338 bp fragment from pSHELFδmod were purified from agarose gels. The 5424 bp fragment was CIP treated to reduce recircularisation and the three fragments ligated overnight at 16° C. using DNA ligase. The final product pSHELFδ26A contained the desired deletion of exon 26A from the SHEL gene with no other mutations.

Sequencing confirmed the region immediately surrounding the deletion was correct. PstI and BssHII restriction sites surrounding the correct region of pSHELFδmod was used to remove the desired segment and reinsert it into the corresponding site of pSHELF. 6.5 μg pSHELF and 7.5 μg pSHELFδmod were digested with BssHII precipitated and digested with PstI. The appropriate three fragments (FIG. 15) were gel purified and ligated using 1U DNA ligase (Boehringer Mannheim Germany) overnight at 16° C. DNA was transformed into E. coli XL1-Blue and transformants selected on plates containing 75 μg/ml ampicillin.

Plasmids were isolated by mini-preparations and screened using BglI digestion. A candidate clone was further analysed by restriction enzyme digestion and automated sequencing was then performed using primers 1R, 3F, 5R, 6F, 7R and T7 forward (5' TAA TAC GAC TCA CTA TAG GG 3', SEQ ID NO: 100) to confirm the entire sequence. The correct sequence was designated pSHELFδ26A.

SHELδ26A displays higher protease resistance than SHEL.

Serum Proteolysis of SHEL

Human serum was obtained from fresh intravenous blood, centrifuged at 2000 g to remove red blood cells and then allowed to clot before serum was removed. Aliquots (20 μl) were stored at −20° C. and thawed when needed. 15 μg tropoelastin in 50 mM sodium phosphate buffer, pH 7.8 was incubated with 0.5 μl serum in a 20 μl reaction for between 1 and 18 hr at 37° C. Similar experiments were conducted with or without the prior addition of inhibitors. Inhibitors were added at the following concentrations; 0.5 or 1Uhirudin, 0.5 or 5 mM Pefabloc SC, 1 or 5 mM PMSF, 25 mM EDTA, 50 or 250 μM Pefabloc PK. All inhibitors were dissolved in water except PMSF which was dissolved in isopropanol. Reactions were analysed by 8% SDS-PAGE. Serum-digested peptides to be used for sequencing were purified by the addition of 1.5 volumes n-propanol, followed by 2.5 volumes n-butanol and stirred overnight. The organic solvents were removed by rotary evaporation and peptides resuspended in 50 mM sodium phosphate buffer, pH 7.8.

Proteolytic Assays

A range of enzyme concentrations was originally used to determine the optimal amount for subsequent experiments. Thrombin (0.01–1U), human plasma kallikrein ($3 \times 10^{-4}$ to $3 \times 10^{-3}$U), human plasmin ($7 \times 10^{-5}$ to $4 \times 10^{-7}$U), bovine trypsin ($5 \times 10^{-4}$ to $4 \times 10^{-3}$U), and human leukocyte elastase ($1.6 \times 10^{-4}$ to $3.2 \times 10^{-3}$U) were added to 10 μg SHEL or SHELδ26A in 50 mM sodium phosphate buffer pH 7.8 in a total volume of 20 μl. All reactions were performed at 37° C. for one hour. Gelatinase A and B were activated using 0.8 mM APMA at 37° C. for 30 minutes (gelatinase A) or 37° C. for 45 minutes (gelatinase B). Gelatinase A ($4 \times 10^{-3-4 \times} 10^{-2}$) and gelatinase B ($2 \times 10^{-5-1 \times 10^{-4}}$) was added to 15 mg SHEL or SHELd26A in a total volume of 50 mL. Gelatinase B reactions were performed in the presence of 0.75 mM APMA. The degradation profile was analysed by 8, 10 or 12% SDS-PAGE.

Zymogram Analysis 8 or 10% zymogram gels were run using (1 mg/ml) porcine gelatin or SHEL as the substrate. After electrophoresis, gels were washed in 2×100 mL 2.5% Triton-X 100 for 20 minutes, followed by 2×100 mL 50 mM Tris-HCl pH7.8, 30 mM NaCl for 5 minutes and incubated overnight at 37° C. in 50 mM Tris-HCl pH 7.8, 30 mM Nacl, 5 mM $CaCl_2$. Gels were fixed with 25% isopropanol, 10% acetic acid, washed with 3×200 mL water and stained using Gelcode (Pierce).

N-Terminal Sequencing

Gels were poured using fresh acrylamide stocks and half the usual amounts of APS and TEMED. Gels were allowed to set for 16–24 hrs. For simple protein profiles, gels were pre-run at room temperature for four hours at 20 mA using 150 mM Tris HCl pH8.8 buffer with 10 μl/L thioglycollic acid in the upper buffer chamber. Samples were loaded and run at 4° C. with fresh buffer for approximately three hours. For more complex profiles gels were pre-run at room temperature in Tris-glycine buffer (25 mM Tris HCl, 192 mM glycine, 0.1% (w/v) SDS, pH approximately 8.3), fresh buffer added and the gel allowed to equilibrate to room temperature before samples were added and run at 20 mA with 10 μl/L thioglycollic acid added to the upper chamber. Pre-stained standards (Kaleidoscope; Biorad, USA) were used to monitor extent of migration.

Gels were blotted onto polyvinylidene difluoride (PVDF) membrane (ProBlott, Applied Biosystems USA) treated according to manufacturer's instructions, overnight at 70 mA using 10 mM CAPS pH 11.0, 10% methanol, 10 μl/L thioglycollic acid buffer at 4° C. with stirring. Blotting was performed using a Hoefer Transblot apparatus and was used according to manufacturer's instructions. The membrane was stained with 0.1% Coomassie blue-R in 50% methanol and destained in 50% methanol, 10% acetic acid. The membrane was washed with water overnight before being air-dried. Bands were excised with a clean scalpel. Samples were blotted onto PVDF as described above. Bands were excised with a clean scalpel and sequenced by Sydney University and Prince Alfred Hospital Macromolecular Analysis Centre (SUPAMAC) using Applied Biosystems hardware and protocols. Alternatively samples were sent to the Biomolecular Resource Facility Australian National University, Canberra, for sequencing.

Peptide Preparation and Use

S-GAL, N-VVGSPSAQDEASPLS-C [SEQ ID NO: 101], is a peptide representing the elastin binding domain of EBP (Hinek and Rabinovitch 1994). It was synthesised by Chiron Mimotopes (Australia) and purified by RP-HPLC as follows. Concentrated peptide in 50 mM ammonium acetate was treated by RP-HPLC initially by perfusion chromatography (POROS, PerSeptive Biosystems USA) using an R2 reverse phase column (4.6×100 mm) run at 9 ml/min along a 0–100% acetonitrile, 0.1% trifluoroacetic acid (TFA) gradient over 7 min was used. Alternatively, a Techogel10 C18 column (2.2×25 cm) was used with a flow rate of 8 ml/min. A 0–100% acetonitrile, 0.1% TFA gradient over 55 min was used after a 10 min initial wash with 30% acetonitrile/0.1% TFA. The column was equilibrated for 10 min between runs due to its large volume. A maximum of 30–50 mg peptide was loaded at any one time. For both methods sample detection was at 214 and 280 nm simultaneously. Both methods were performed using Pharmacia (Sweden) pumps and detectors. The solution was removed from the collected samples by lyophilisation and purified peptide weighed to determine yield.

A large molar excess of S-GAL in Milli-Q water (10 to 200 fold) was added to 15 μg SHEL in 50 mM sodium phosphate pH7.8 made up to a total volume of 40 μl and preincubated at 37° C. for one hour as suggested by Hinek and Rabinovitch (1994) before the selected protease (kallikrein, $6-15 \times 10^{-4}$U; thrombin 0.1–0.2U; trypsin $2 \times 10^{-3}$U; plasmin, $1.5-3.7 \times 10^{-5}$U; human leukocyte elastase, $1.6 \times 10^{-3}$U; serum 1yl) was added according to the optimal amounts determined above for 10 to 80 minutes. Various dilutions of serum from ½–1/50 in 50 mM sodium phosphate pH7.8 were used and both SHEL and SHELδ26A were used for each experiment.

A peptide representing a region of SHEL cleaved by a selection of serine proteases: N-AAKAQLRAAAGLGA-C (serine protease site peptide, SPS-peptide, aa 511–524 of SEQ ID NO:4) was synthesised by Chiron Mimotopes (Australia) to test whether its presence could protect SHEL from degradation by acting as a competitor. Experiments were conducted in parallel with S-GAL using identical procedures (see above). Both SHEL and SHELδ26A were used. Each reaction was analysed by 10% SDS-PAGE. Gels were scanned by densitometry and the volume of full-length SHEL calculated as follows. Scanning densitometry of stained gels was performed using the Molecular Dynamics Personal Densitometer. Images were analysed and quantitated using ImageQuant software (Version 3.2, Molecular Dynamics USA).

Proteolysis During Coacervation 10 mg/ml SHEL in 50 mM sodium phosphate pH7.8 and 150 mM NaCl was allowed to coacervate at 37° C. until cloudy before adding human plasma kallikrein ($6 \times 10^{-4}$U), thrombin (1U), plasmin ($1.5 \times 10^{-5}$U), trypsin ($2 \times 10^{-3}$U), HLE ($1.6 \times 10^{-3}$U) and serum (0.75 µl) for one hour. Control reactions were performed at 16° C. for three hours. Extent of proteolysis was monitored by SDS-PAGE.

Results

A. Degradation of SHEL by Serum

Figure 5:
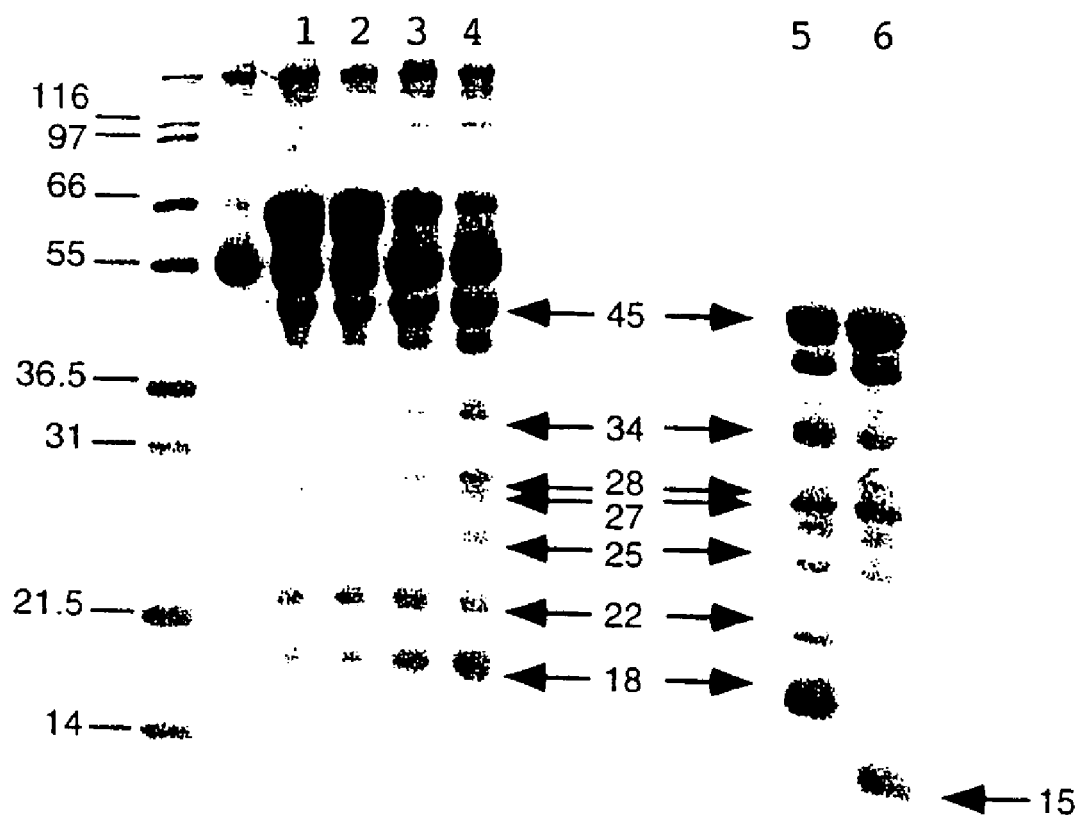
FIG. 5 shows 10% SDS PAGE analysis of SHEL with serum after incubation for 1, 2, 3 or 18 hours (Lanes 1 to 4). Lanes 5 and 6: peptide fragments produced by serum digestion of SHEL and SHELδ26A respectively, purified by butanol solubilisation. Approximate sizes of fragments produced are shown in kDa. Size markers are shown in kDa.

Human tropoelastin was degraded by human serum into discrete bands, resistant to further degradation. The same degradation profile was seen by SDS-PAGE with overnight incubation as with incubations left for one hour (FIG. 5). FIG. 5 clearly shows the peptide fragments after purification from serum using butanol. The sizes of the major bands are approximately 50, 45, 35, 28, 27, 25, 22 and 18 kDa, visually similar to that obtained by Romero et al (1986) using porcine tropoelastin. The pattern of peptides produced was reproducible over many separate experiments. Similar results were obtained with SHELδ26A (FIG. 5) but the 22 and 18 kDa bands were absent and replaced by a 15 kDa band.

B. Effect of Protease Inhibitors on Serum Degradation

Figure 6:
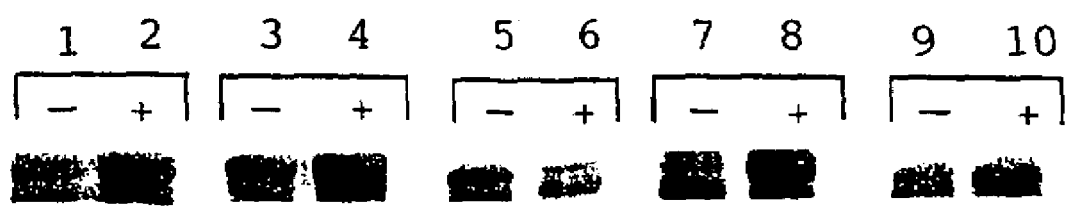
FIG. 6 shows 8% SDS-PAGE analysis of the effect of protease inhibitors on serum degradation of SHEL. Lanes 1, 3, 5, 7 and 9: SHEL incubated with serum; lane 2: SHEL incubated with serum and 0.5 mM Pefabloc SC; lane 4: SHEL incubated with serum and 5 mM PMSF: lane 6: SHEL incubated with serum and EDTA; lane 8: SHEL incubated with serum and 50 mMPefabloc PK; and lane 10: SHEL incubated with serum and 1 unit Hirudin.
Figure 19:
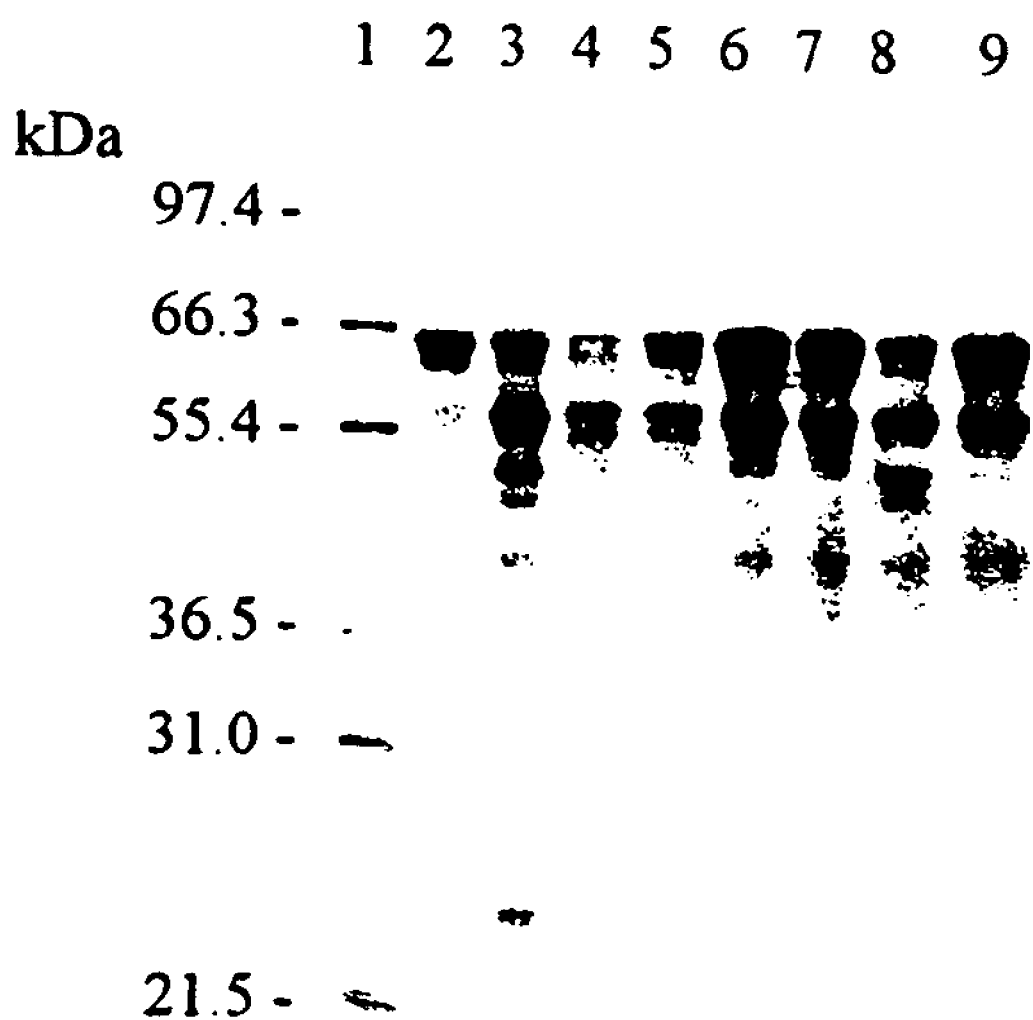
FIG. 19 shows protease digestion of SHEL in solution. Lane 1, standards. Lane 2, SHEL. Lane 3, SHEL plus serum. Lane 4, SHEL plus 72 kDa gelatinase. Lane 5, SHEL plus 92 kDa gelatinase. Lanes 6 and 7, serum plus APMA (1 hr incubation), Lanes 8 and 9, serum plus APMA (overnight incubation).
Figure 20:
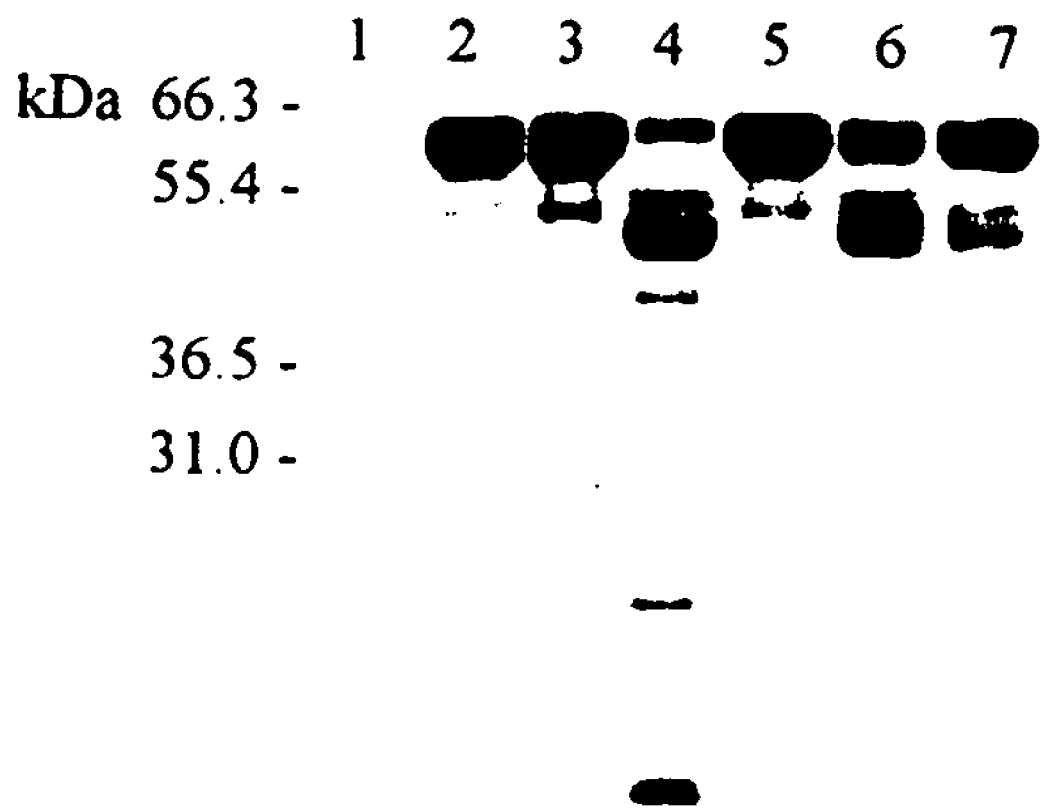
FIG. 20 shows human serum kallikrein digestion of SHEL in sodium phosphate buffer, pH7.8 in the presence and absence of urea. Lane 1, standards, Lane 2, SHEL (not incubated), Lane 3, SHEL incubated with buffer (no kallikrein), Lane 4, SHEL plus kallikrein, Lane 5, SHEL plus urea in buffer (no kallikrein), Lane 6, SHEL plus kallikrein in 0.3M urea, Lane 7, SHEL plus kallikrein in 1M urea.

FIG. 6 shows the amount of full-length SHEL after incubation with serum in the presence or absence of various protease inhibitors. Wide-spectrum serine protease inhibitors were found to inhibit degradation since both Pefabloc SC and PMSF protected tropoelastin from cleavage (FIG. 6). In contrast, EDTA which is an inhibitor of metalloproteinases, appeared to promote digestion. This is an unexpected result because the metalloproteinases gelatinase A and gelatinase B digest tropoelastin (FIG. 19). Protease inhibitors specific for the serine proteases thrombin and kallikrein were also tested. Hirudin, a highly specific inhibitor of thrombin, did not appear to significantly inhibit degradation whereas Pefabloc PK, specific for kallikrein, inhibited proteolysis (FIG. 6).

C. Degradation of SHEL with Specific Proteases

Human Thrombin

Figure 14:
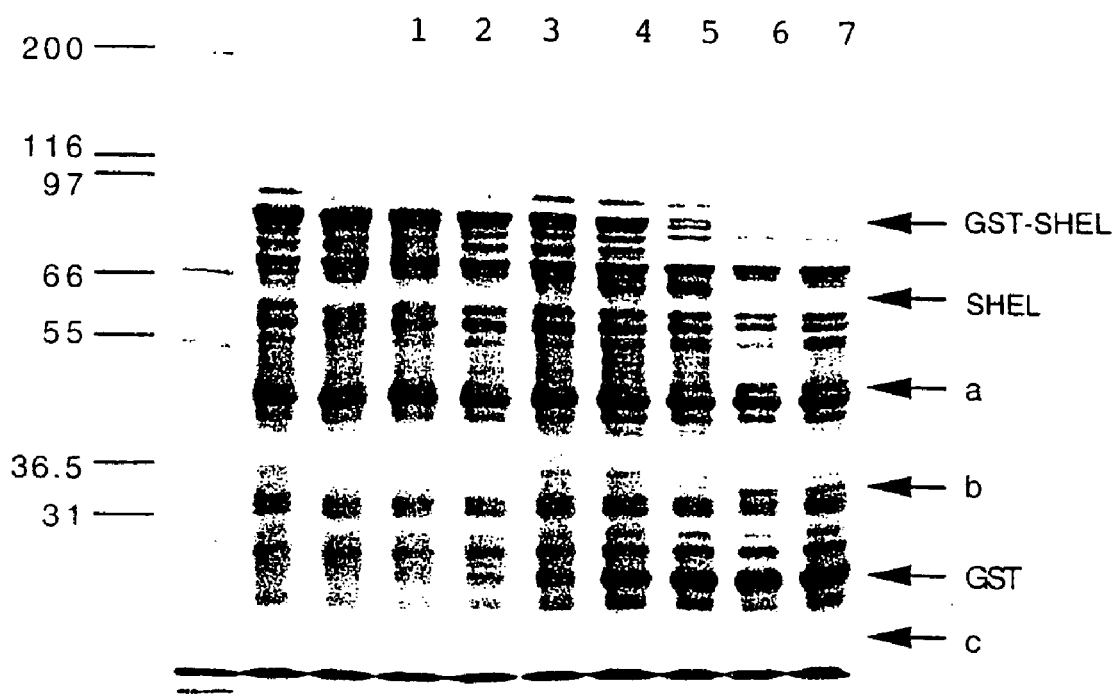
FIG. 14 shows 8% SDS-PAGE gel of the effect of thrombin cleavage of soluble cell lysate containing GST-SHEL. Increasing amounts of thrombin: lane 1: 0.001 unit; lane 2: 0.005 unit; lane 3: 0.010 unit; lane 4: 0.050 unit; lane 5: 0.100 unit; lane 6: 0.500 unit and lane 7: 1.000 unit were added to soluble cell lysate.

Thrombin is able to cleave GST-SHEL extensively and in a reproducible manner. Cleavage of GST-SHEL bound to glutathione agarose was performed by washing and resuspending beads in 1× thrombin cleavage buffer (50 mM Tris-HCl pH8.0, 150 mM NaCl, 2.5 mM $CaCl_2$) and adding human thrombin (Sigma) from 0.1 to 1% (w/v) thrombin: fusion protein at 25° C. for one hour (Smith and Johnston 1988). Soluble bacterial lysates used as substrate were incubated similarly with 1× thrombin cleavage buffer, added from a 10× stock. GST (26 kDa) was evident on beads by SDS-PAGE but SHEL could not be identified in the supernatant in numerous experiments. To determine whether thrombin was degrading SHEL, the entire cell lysate was subject to cleavage with increasing concentrations of thrombin. 0.01U thrombin was the lower limit for cleavage but 0.05U and greater are more effective (FIG. 14). GST was clearly present. However, with 0.01U thrombin a band at approximately 64 kDa could be discerned which may represent SHEL although this was not nearly as intense as the GST band. With higher thrombin concentrations this band disappeared and smaller fragments at 45, 34 and 22 kDa were noted indicating that SHEL was indeed being cleaved by thrombin.

Figure 7:
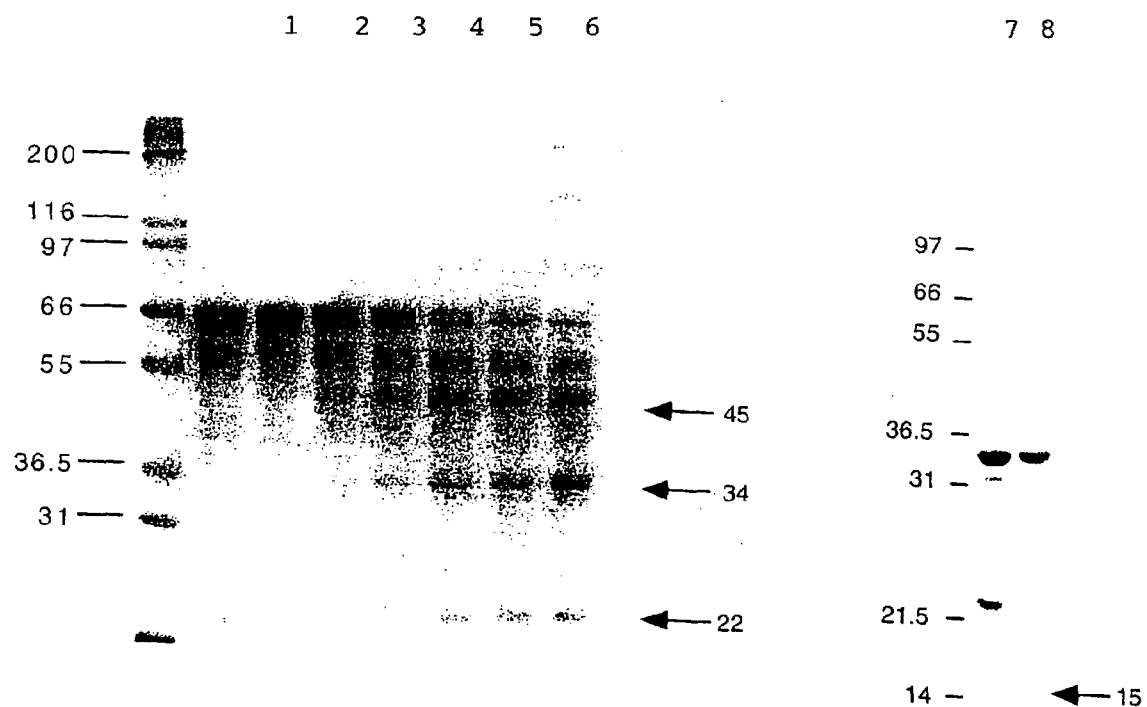
FIG. 7 shows 8% SDS-PAGE analysis of the effect of thrombin on SHEL and SHELδ26A. Increasing amounts of thrombin: lane 1 (0.01 units); lane 2 (0.05 units); lane 3 (0.10 units); lane 4 (0.15 units); lane 5 (0.20 units) and lane 6 (0.25 units) were added to SHEL. Lanes 7 and 8: effect of thrombin (1U) on degradation of SHEL and SHELδ26A respectively. Fragment sizes are estimated in kDa. Size markers are shown in kDa.

When increasing amounts of thrombin were added to pure SHEL, four major fragments were identified by SDS-PAGE estimated at 45, 34, 22 and 13 kDa (FIG. 7) in addition to faint minor bands. The sizes of the major products were very similar to those seen with thrombin digests of GST-SHEL lysates. Even with an excess of thrombin added (1U/10 µg SHEL) the smaller bands were resistant to further degradation whilst the 45 kDa fragment disappeared. The pattern of degradation did not appear to be the same as the serum produced peptides. When the hirudin was added to reaction, degradation was inhibited (not shown) unlike the results seen with serum. The patterns of degradation seen with SHELδ26A was slightly different with the 22 kDa fragment reduced in size to about 15 kDa consistent with the fragment not containing 26A (FIG. 7).

Human Plasma Kallikrein

Figure 8:
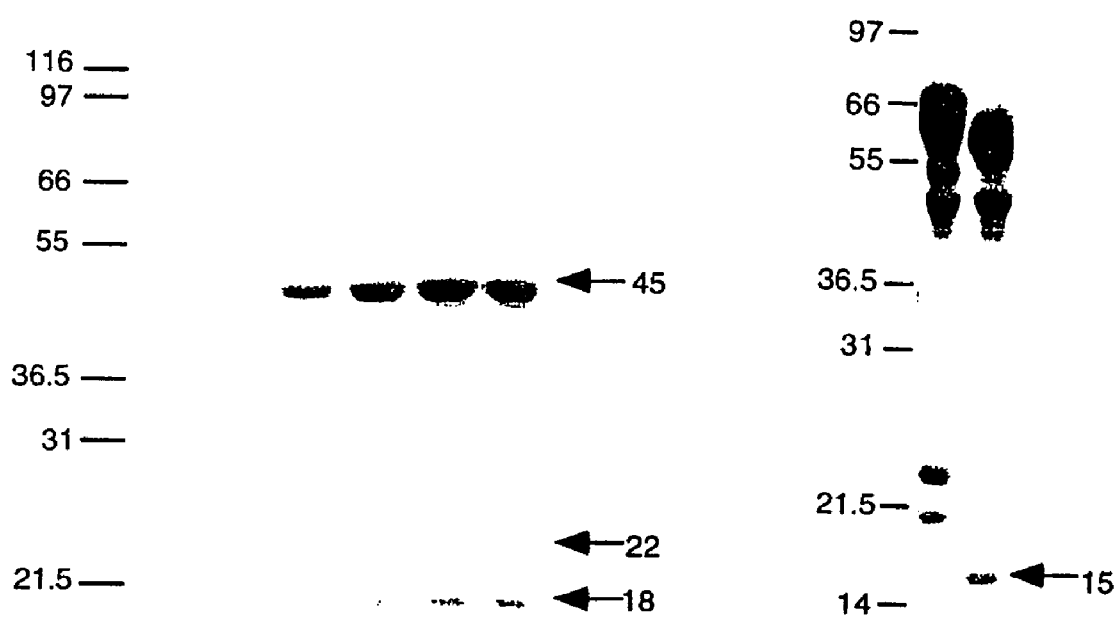
FIG. 8 shows 8% SDS-PAGE analysis of the effect of kallikrein on SHEL and SHELδ26A. Increasing concentrations of kallikrein: lane 1: $3.0\times10^{-4}$; lane 2: $6.0\times10^{-4}$; lane 3: $1.5\times10^{-3}$ and lane 4: $3.0\times10^{-3}$ were added to SHEL. Lanes 5 and 6: effect of kallikrein ($6\times10^{-4}$U) on degradation of SHEL and SHELδ26A respectively. Fragment sizes and size markers are shown in kDa.

Like thrombin, increasing amounts of human plasma kallikrein added to SHEL resulted in specific and reproducible degradation. Three major fragments were identified by SDS-PAGE (FIG. 8) estimated to be 45, 22 and 18 kDa, in addition to faint minor bands. The major bands at 45 kDa and 18 kDa were resistant to further degradation whilst the 22 kDa fragment eventually disappeared. Again, the pattern of degradation was not identical to that seen by serum. Pefabloc PK could inhibit degradation by plasma kallikrein (not shown). The pattern of degradation of SHELδ26A was somewhat different, with the 22 and 18 kDa fragments missing and replaced by a 15 kDa fragment (FIG. 8), as was seen for serum.

Bovine Trypsin

Figure 9:
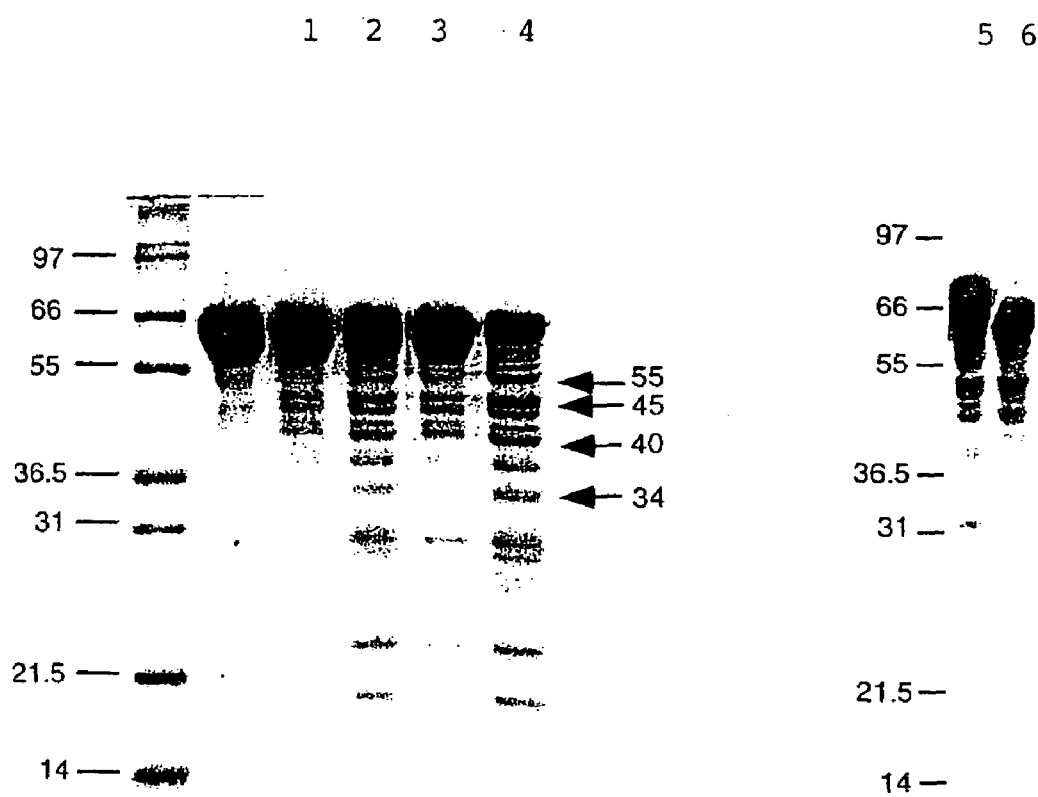
FIG. 9 shows 10% SDS-PAGE analysis of the effect of bovine trypsin on SHEL and SHELδ26A. Increasing concentrations of bovine trypsin: lane 1: $5\times10^{-4}$; lane 2: $1\times10^{-3}$; lane 3: $2\times10^{-3}$ and lane 4: $4\times10^{-3}$ were added to SHEL. Lanes 5 and 6: effect of bovine trypsin ($2\times10^{-3}$U) on SHEL and SHELδ26A respectively. Fragment sizes and size markers are shown in kDa.

Trypsin digestion of SHEL was very extensive, resulting in complete degradation with prolonged treatment. However, with dilute amounts of enzyme ($4 \times 10^{-3}$U) major bands could be identified at approximately 50, 45, 40, 38, 34, 31, 22 and 18 kDa, giving an overall pattern similar to serum products (FIG. 9). Indeed, at low enzyme concentrations the trypsin digest profile looked virtually identical to the serum digest profile. However, trypsin digestion was not easily reproducible due to the vigorous action of trypsin on SHEL. Similar results were obtained using SHELδ26A (FIG. 9)

except that the sizes of the smaller fragments below 34 kDa were all reduced in size by approximately 4 kDa and as for kallikrein and serum, the 22 and 18 kDa fragments were replaced by a single fragment at 15 kDa.

Human Plasmin

Figure 10:
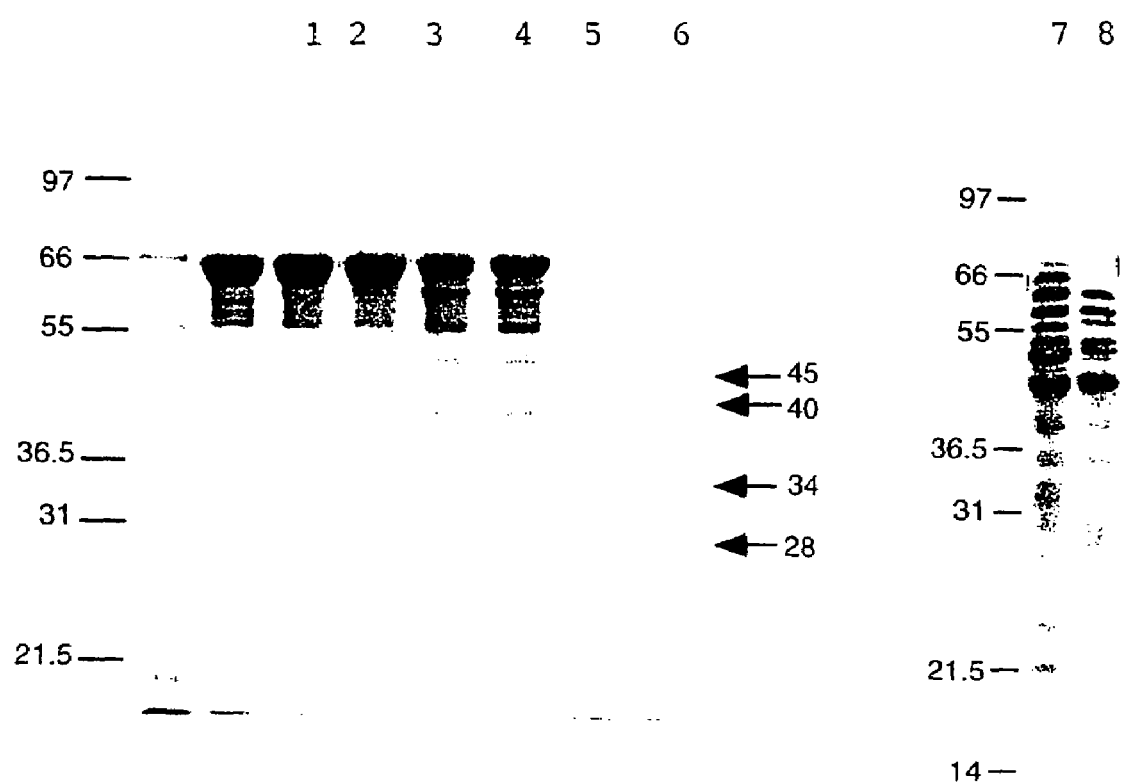
FIG. 10 shows 10% SDS-PAGE analysis of the effect of plasmin on SHEL and SHELδ26A. Increasing concentrations of plasmin: lane 1: $3.7\times10^{-7}$; lane 2: $7.4\times10^{-7}$; lane 3: $3.7\times10^{-6}$; lane 4: $7.4\times10^{-6}$; lane 5: $3.7\times10^{-5}$; lane 6: 7.4×10–5 were added to SHEL. Lanes 7 and 8: effect of plasmin ($7.4\times10^{-5}$U) on SHEL and SHELδ26A respectively. Fragment sizes and size markers are shown in kDa.

Using plasmin at low concentrations also gave a profile very similar to both serum and trypsin (FIG. 10) while at high concentration extensive degradation occurred. Major bands could be isolated using low concentration plasmin at 55, 45, 40, 34, 28, 22 and 18 kDa, similar but not identical to serum digested products. Similar results were obtained using SHELδ26A (FIG. 10) except that smaller fragments below 34 kDa were reduced by approximately 4 kDa and the 22 and 18 kDa fragments were replaced by 17 and 15 kDa fragments.

Human Leukocyte Elastase (HLE)

Figure 11:
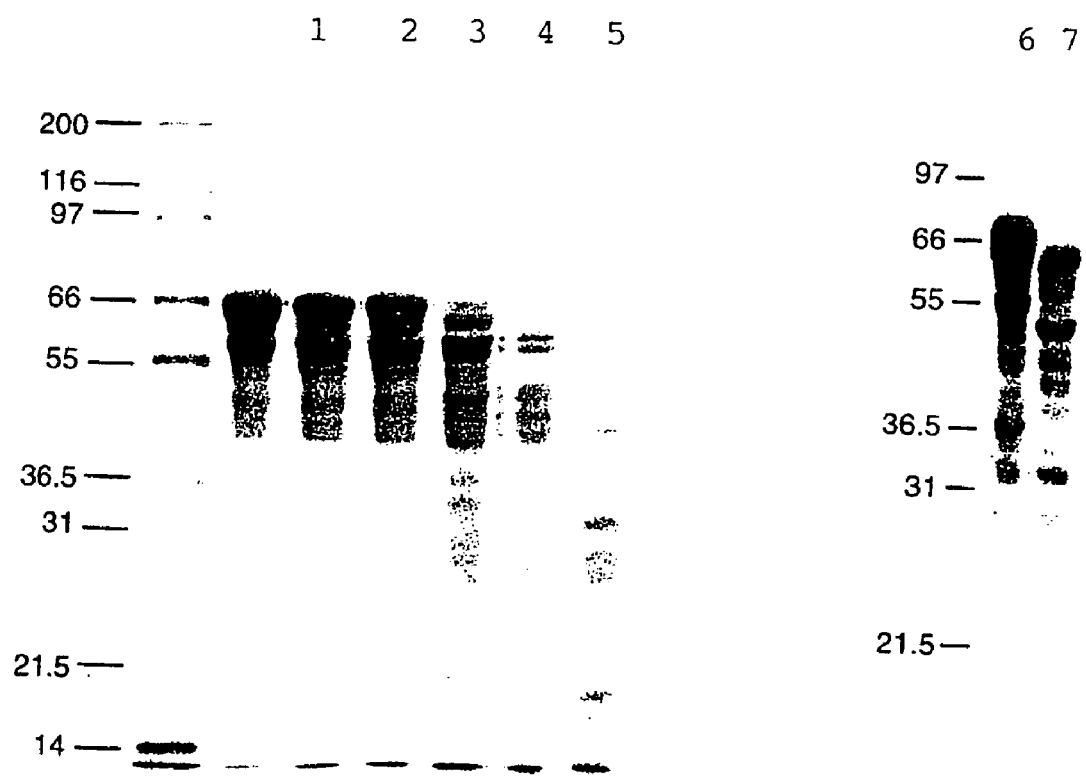
FIG. 11 shows 10% SDS-PAGE analysis of the effect of human leukocyte elastase (HLE) on SHEL and SHELδ26A. Increasing concentrations of HLE: lane 1: $1.6\times10^{-4}$; lane 2: $3.2\times10^{-4}$; lane 3: $8.0\times10^{-4}$; lane 4: $1.6\times10^{-3}$; lane 5: $3.2\times10^{-3}$ were added to SHEL. Lanes 6 and 7: effect of HLE ($1.6\times10^{-3}$U) on SHEL and SHELδ26A respectively. Fragment sizes and size markers are shown in kDa.

HLE resulted in extensive degradation if left for extended period. Using $1.6 \times 10^{-2}$ U numerous fragments were seen with two prominent fragments at 32 and 18 kDa (FIG. 11). Fragments were very difficult to isolate, however, and over digestion occurred easily. SHELδ26A produced a similar profile but with a series of fragments appearing 4 kDa smaller (FIG. 11).

D. Zymogram Analysis of Serum and Proteases

Figure 16:
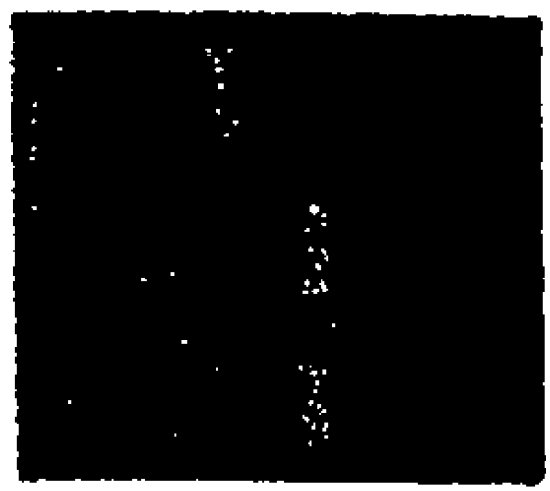
FIG. 16 shows a zymogram analysis of SHEL digested with serum (Lane 1), serum with Pefabloc SC (Lane 2) or kallikrein (Lane 3).

To confirm the identity of proteases involved in serum digestion of SHEL, a zymogram using SHEL as a substrate was used to analyse the digestion of SHEL by serum and specific proteases (FIG. 16).

The SHEL zymogram digested with serum shows a distinct cleared zone at 64 kDa and a much fainter second cleared zone (FIG. 16). No cleared zones corresponding to the other serum proteases were detected in the serum. It is likely that this result was due to the abundance of these proteases in serum, and the degree of molecular unfolding of the protease in the zymogram.

The second cleared zone was not seen when the serine protease inhibitor PMSF was used in the analysis. This indicates that the second cleared zone corresponds to the digestion of SHEL by kallikrein. To further confirm kallikrein activity against SHEL, serum was electrophoresed through a zymogram gel containing SHEL, the gel strip containing serum was cut into approximately 3 mm strips and each gel slice incubated with 30 mg of SHEL in solution. The supernatant was then analysed by SDS-PAGE. A pattern identical to kallikrein was seen from the gel slice from the zymogram corresponding to the region for kallikrein (data not shown). This confirmed kallikrein activity in serum.

Figure 17:
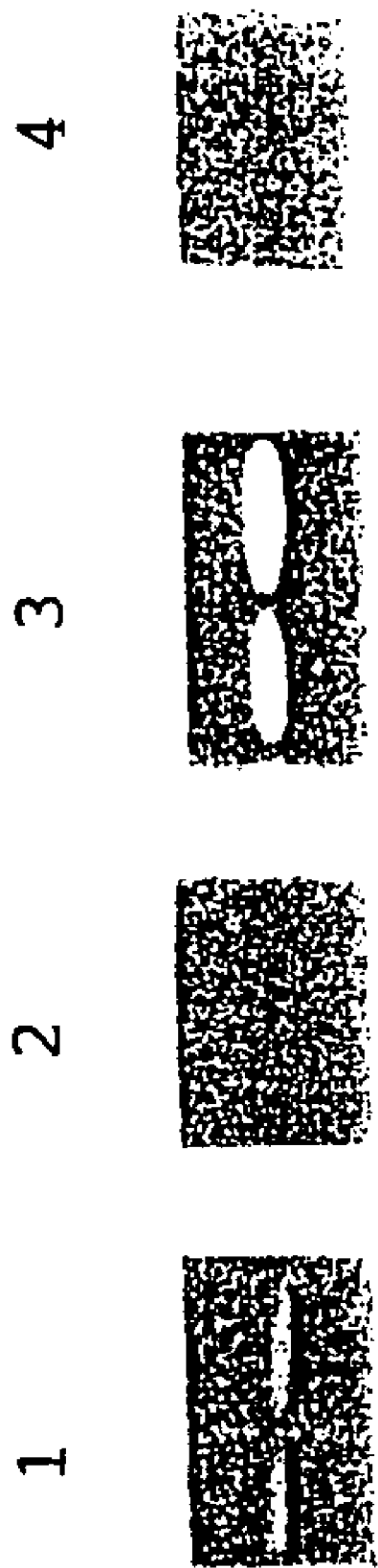
FIG. 17 shows a zymogram analysis of gelatin digested with serum in the presence of $Ca^{2+}$ (Lane 1), $Zn^{2+}$ (Lane 2), $Ca^{2+}$ and $Zn^2$ (Lane 3) and $Ca^{2+}$, $Zn^{2+}$ and EDTA (Lane 4).
Figure 18:
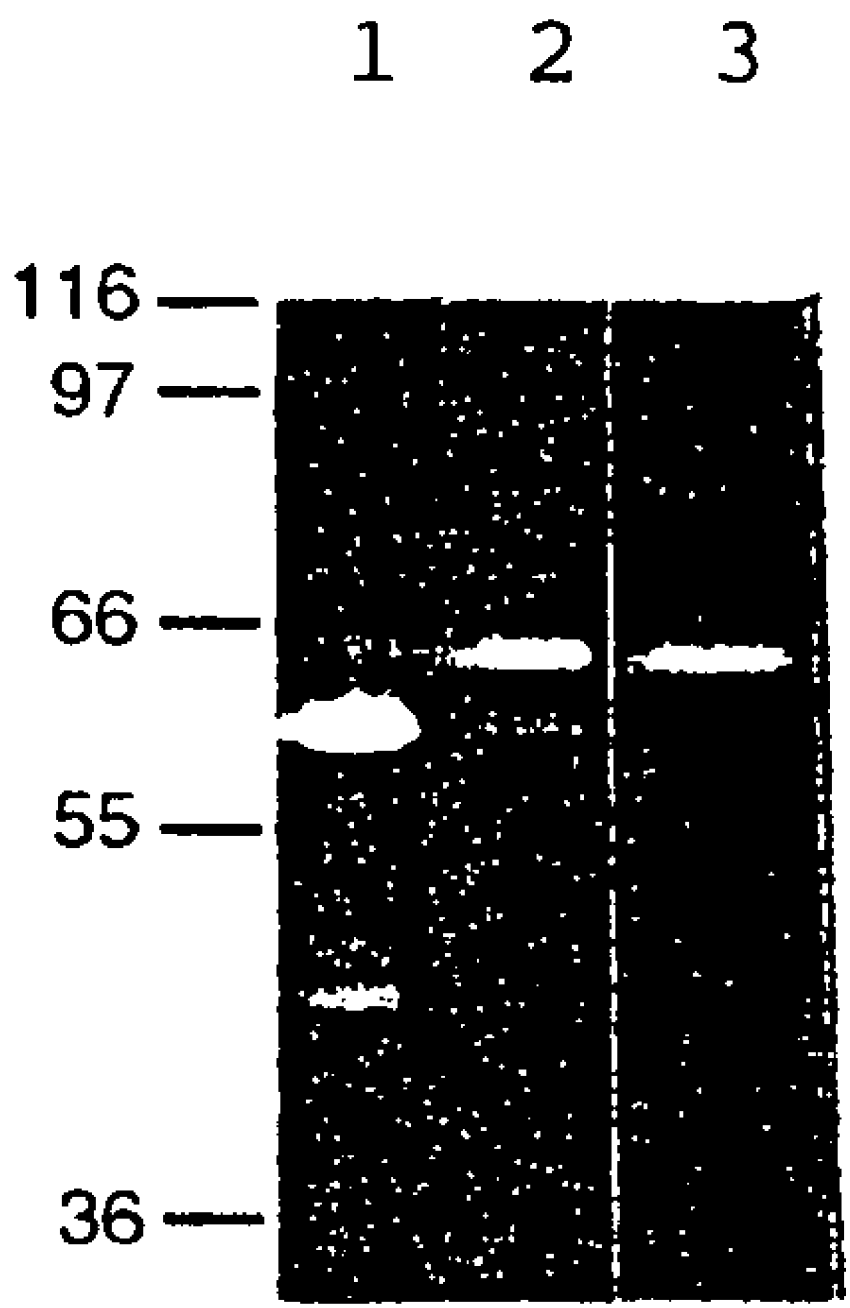
FIG. 18 shows a zymogram analysis of gelatin digested with AMPA activated gelatinase A (Lane 1), unactivated gelatinase A (Lane 2) and serum (Lane 3).

The 64 kDa zone identified in the zymogram analysis of SHEL digested with serum did not correspond to any of the serine proteases analysed. A 2 dimensional zymogram (first dimension isoelectric focusing gel) indicated that the isoelectric point of the enzyme which corresponds to the 64 kDa zone was pI 5–5.5 (data not shown). A SwissProt database search combining pI and molecular weight indicated that the enzyme which corresponds to the 64 kDa zone was likely to be either gelatinase A or B. A zymogram analysis of gelatin digested with gelatinase A or serum demonstrated a zone of digestion corresponding to 64 kDa (FIG. 18). This further confirms that the 64 kDa zone observed in the zymogram analysis of SHEL digested with serum corresponds to gelatinase A. A cleared zone corresponding to gelatinase B is observed at a different location in this zymogram analysis. In a zymogram analysis of gelatin digested with serum, the 64 kDa zone was not observed in the presence of EDTA, or in the absence of $CaCl_2$, or in the presence of $ZnCl_2$ only (FIG. 17). When $CaCl_2$ or $ZnCl_2$ was added to the digestion, the 64 kDa zone was observed (FIG. 17). These results further support the contention that the enzyme which corresponds with the 64 kDa zone in the zymogram analysis of SHEL digested with serum is gelatinase A. Unactivated and APMA-activated gelatinase A and gelatinase B were analysed by gelatin zymography. A 64 kDa zone was observed in the gelatin zymogram digested with unactivated gelatinase A (FIG. 18). This indicated that the proteolytic activity observed at 64 kDa in the serum digestion of the SHEL zymogram is mediated by the unactivated form of gelatinase A. A zone corresponding to approximately 60 kDa was observed in the gelatin zymogram digested with APMA-activated gelatinase A (FIG. 18).

E. Mapping of Protease-Susceptible Sites

The thrombin, kallikrein, plasmin, trypsin and serum-produced peptides indicated in FIGS. 5 to 11 by an arrow, were N-terminally sequenced and assigned to regions of SHEL. Peptides corresponded either to the N-terminus of SHEL or to cleavage sites C-terminally adjacent to a Lys or Arg. Sequences of peptides are shown in Table 1 and the positions of the cleavage sites are indicated diagrammatically in FIG. 1.

The actual sizes, in kDa, of the fragments shown in Table 1 were determined from the amino acid sequence and are shown in brackets. In some cases, this differed from the apparent size as determined by SDS-PAGE. Curiously, one site between residues 515 and 516 (Arg and Ala) was common to thrombin and kallikrein. In addition, this same site was also cleaved by human serum. This site was identified by sequencing to be located within 26A. The lack of a second kallikrein-produced fragment in SHEL δ26A is therefore consistent with this site being absent from this isoform. The other serum-produced bands, which were minor in comparison, were unique and appeared to consist of a mixture of peptides making the designation tentative. These peptides were the same size in both SHEL and SHELδ26A (FIG. 7) indicating that they are predominantly N-terminal and that the other peptide fragment is present at a much lower level. Any significant proteolysis at these other sites in SHELδ26A should result in a 4 kDa reduction in peptide size which was not evident. Due to the rampant degradation seen by both trypsin and plasmin, the smaller fragments were unable to be isolated in sufficient quantity for sequencing. However, the sizes of the fragments indicate that the 22 and 18 kDa fragments of trypsin and plasmin are probably the same sequence as for kallikrein and serum. Each of the plasmin-produced bands sequenced were a mixture of the same identified sequences, not seen with any other protease or serum, and N-terminal sequence also. Since not all the plasmin and trypsin-produced peptides were able to be identified unambiguously, the likely region of cleavage for these enzymes is not shown in FIG. 1.

F. Effect of S-Gal and SPS-Peptide on Degradation

Figure 12:
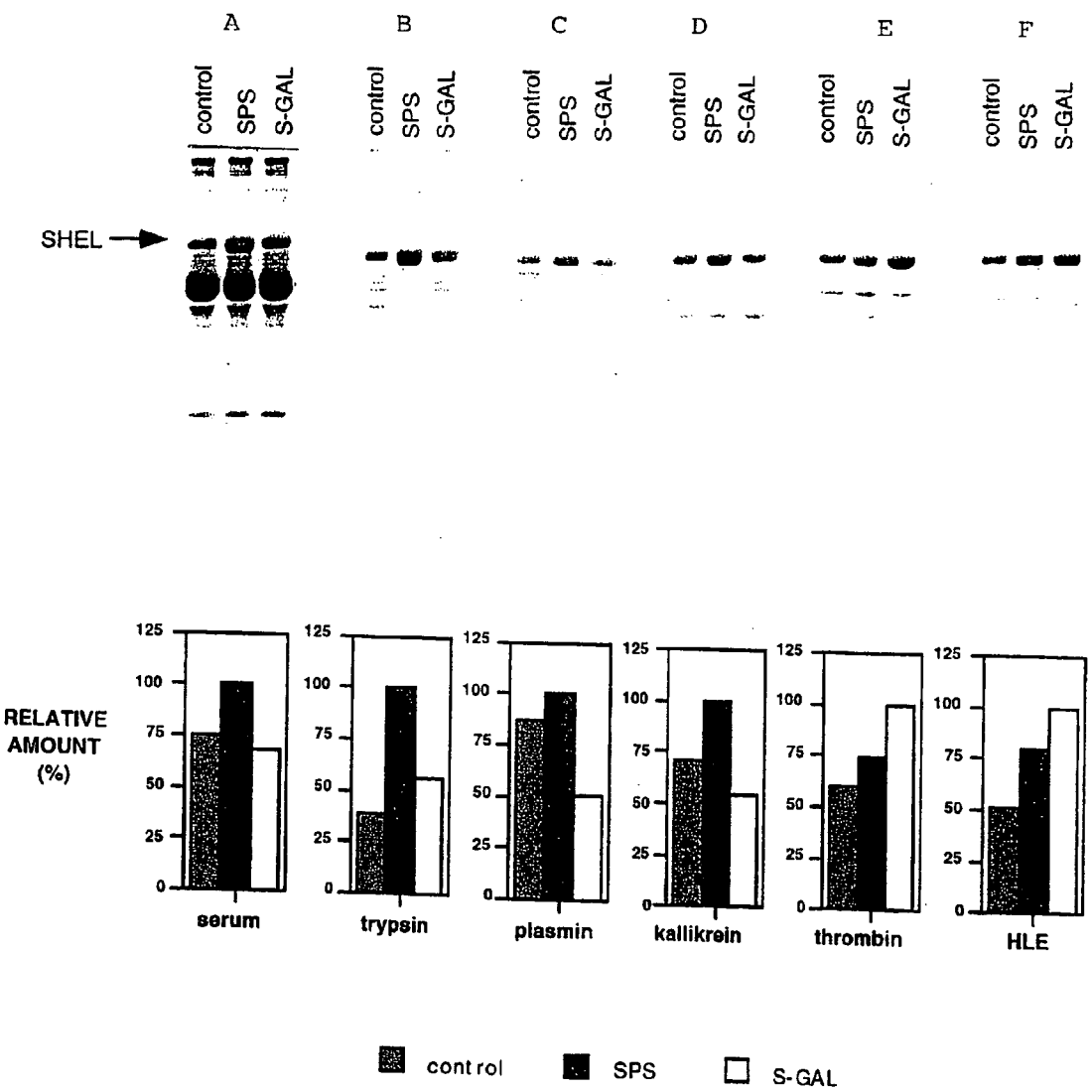
FIG. 12 shows 10% SDS-PAGE analysis of the effect of S-GAL and SPS-peptide on degradation of SHEL with A: serum, ½ dilution 20 min; B: trypsin 20 min; C: plasmin $1.5\times10^{-5}$U 20 min; D: kallikrein $15\times10^{-4}$U 40 min; E: thrombin 0.1U 20 min and F: HLE 70 min. Thrombin and kallikrein were used with a 100:1 ratio. Gels were scanned by densitometry and the relative amount of each full-length SHEL band is shown in in a histogram.

The major serine protease site (R/AAAGLG, SEQ ID NO:9) identified in SHEL as common to thrombin, kallikrein, serum and probably trypsin and plasmin, was produced with some flanking amino acid residues as a 14 amino acid peptide (SPS-peptide). This was added to proteolytic digests of SHEL and SHELδ26A to assess whether this peptide could inhibit degradation by acting as an alternative site for recognition and cleavage by proteases. In addition, S-GAL, a 15 amino acid peptide corresponding to the elastin binding domain of EBP was produced to assess whether its inhibition of porcine pancreatic elastase (Hinek and Rabinovitch 1994) could be extended to other proteases with tropoelastin-degrading ability. Using a 100:1 molar excess of SPS-peptide to SHEL, more full-length SHEL was evident compared with controls using trypsin, plasmin, kallikrein and serum, judged visually by SDS-PAGE and confirmed by scanning densitometry (FIG. 12). The effect was most obvious with short incubations (20 minutes) and was seen with both SHEL and SHELδ26A (not shown). SPS-peptide also resulted in more full-length SHEL using thrombin and HLE but to a lesser extent (FIG. 12) but longer incubations with thrombin did appear to show some inhibition (FIG. 12). Degradation by HLE, however, was consistently inhibited by S-GAL even with longer incubations when inhibition with SPS-peptide was no longer seen, but was not repressed altogether (FIG. 12).

G. Effect of coacervation on degradation of SHEL

SHEL, when in the coacervated state at 37° C. was significantly protected from degradation by both thrombin and kallikrein (FIG. 13) but not by plasmin. There was also some inhibition of HLE, trypsin and serum (FIG. 13). This inhibition of degradation was not due to the presence of high concentrations of NaCl in the reaction mixture as control reactions using both lesser concentrations of SHEL that did not coacervate at 37° C. (not shown) and reactions performed at lower temperatures not conducive to coacervation, did not show any difference in degradation in the presence or absence of NaCl (FIG. 13).

Discussion

Inhibition Study of Serum Degradation of SHEL.

Human serum was able to degrade tropoelastin in a specific and reproducible manner into at least five or six major peptide fragments. The SDS-PAGE banding pattern with serum is visually similar to that of Romero et al (1986). Various inhibitor studies confirmed the protease to be a serine protease which could be inhibited by the broad spectrum serine protease inhibitors Pefabloc SC and PMSF.

The lack of inhibition of serum digestion by EDTA suggested that metalloproteinase activity was not a major contributor to SHEL digestion. Indeed, EDTA appeared to enhance degradation by serum perhaps by modulating the action of an inhibitor of serum proteases. However, it is clear that metalloproteinases digest tropoelastin because SHEL was digested with gelatinase A and gelatinase B, as demonstrated by the SDS-PAGE and zymogram analysis of SHEL digested with these enzymes.

It is expected that metalloproteinases are a major source of proteolytic activity when tropoelastin is exposed to wound exudate. Indeed, a number of studies have demonstrated the existence of metalloproteinases in wound exudate, including MMP-2 (gelatinase A) and MMP-9 (gelatinase B) (Tarlton et al. 1997). Accordingly, the invention contemplates the modification of digestion of tropoelastin by metalloproteinases in wound exudate, by use of the methods, derivatives and peptidomimetic molecules of the invention.

Thrombin did not appear to be responsible for the majority of serum cleavage because the degradation by serum was not substantially inhibited by the thrombin-specific inhibitor hirudin, yet controls using tropoelastin and thrombin were inhibited. Pefabloc PK, specific for kallikrein inhibited degradation. Romero et al (1986) found that incubation of tropoelastin with kallikrein resulted in a somewhat similar profile to its incubation with serum. The present inhibitor studies with PefablocPK are therefore consistent with kallikrein and/or proteases with similar behaviour being involved. The inhibitor Pefabloc PK is, however, not completely specific for kallikrein. According to data supplied by the manufacturer, the inhibitor constant for plasma kallikrein is 0.7 μmol/L while the next most likely enzyme to be inhibited after kallikrein is trypsin with an inhibitor constant of 1.3 μmol/L followed by plasmin at 10 μmol/L. Thus, if present in excess Pefabloc PK may be inhibiting these enzymes also. However, the lowest concentration at which complete inhibition was seen (50 μM) was the manufacturer's recommended amount for inhibition of kallikrein in plasma samples.

Identification of Serum Proteolysis

A number of enzymes have been proposed to be responsible for the serum degradation of tropoelastin. Kallikrein (Romero et al 1986) and plasmin (McGowan et al 1996) have both been put forward as potential sources of proteolysis while a trypsin-like protease was thought to be responsible for the degradation products seen when tropoelastin was isolated from tissues (Mecham and Foster 1977). A visual comparison of SHEL degradation products from serum with the individual protease digestion products revealed only a limited similarity with thrombin and kallikrein-produced peptides while trypsin and plasmin digests appeared more similar to serum-digested peptides but only when used at low concentration. Higher concentrations and/or longer incubations completely degraded SHEL and SHELδ26A in contrast to long incubations with serum which did not change the pattern greatly.

Increasing amounts of thrombin easily degraded SHEL but only three major fragments were noted, unlike serum-produced peptides where 5–6 fragments were noted. Coupled with the observation from the inhibitor studies that the thrombin-specific inhibitor hirudin did not substantially reduce serum degradation, thrombin does not appear to be the major enzyme involved in serum proteolysis of SHEL. This was corroborated by sequencing of the peptide products which showed that although one of the two sites recognised by thrombin was likewise recognised by serum, the other site was not. This may have been a consequence of low thrombin concentration but this is unlikely since both sites are recognised to a similar extent (FIG. 7).

Similarly, the profile of SHEL seen after kallikrein digestion only showed limited similarity to the serum produced profile i.e. the presence of a 45 kDa fragment and two fragments around 20 kDa. Sequencing of the peptides showed that both the sites recognised by kallikrein were recognised by serum. The other serum-produced fragments, however, were not seen as major products of kallikrein digestion although some other fragments were present at a very low level (FIG. 8). Long incubations with kallikrein (overnight) failed to increase the intensity of other fragments nor increase to resemble serum digestion products (not shown), indicating that kallikrein was unlikely to be responsible for the additional serum-produced fragments. The sequencing data, effect of a kallikrein specific protease inhibitor and visual appearance of the digestion products by SDS-PAGE are all consistent with the involvement of kallikrein in serum digestion. However the presence of other serum peptide fragments not seen as major products of kallikrein digestion indicates that kallikrein alone is not responsible for the pattern seen in serum digests.

In contrast to thrombin and kallikrein, treatment with plasmin and trypsin resulted in extensive degradation which could completely degrade SHEL if incubated for extended periods. The degradation profile seen with plasmin was quite unlike that seen by McGowan et al (1996) where only 68 and 45 kDa bands were seen suggesting that the degradation had not proceeded very far in that case. Each of these digestion profiles were more similar to serum products than either thrombin or kallikrein. By visual inspection trypsin and plasmin appeared almost identical to serum digests and each other but only at a low concentration.

There was some difficulty in the sequencing of plasmin and trypsin peptides. The plasmin-produced peptides that were sequenced were found to consist of a mixture of at least two overlapping sequences at 78/79 and 81/82 (K/AAK [aa 80–83 of SEQ ID NO:4] and K/AGA [aa 83–86 of SEQ ID NO:4]) which were the same in all of the peptide fragments sequenced. In addition, sequence from the N-terminus of SHEL was also present, which made these peptides very difficult to identify unambiguously. The presence of the same peptides throughout each fragment may be an artifact resulting from this sequence co-migrating through the entire gel with other peptides and so contaminating each subsequent peptide (J. McGovern Biomolecular Resource Facility, John Curtin School of Medical Research, Australian National University, personal communication). This may have been compounded by the low levels of peptide obtained for each fragment due to the rampant degradation by plasmin.

Similarly, low levels and poor resolution made it difficult to obtain sequence for the smaller trypsin peptides. However, clear sequence data were obtained for the larger fragments which all corresponded to N-terminal sequences as was the case for the same peptides from serum. This coupled with the observation that Pefabloc PK could also inhibit trypsin in controlled reactions (not shown) and the visual similarity of peptide fragments is consistent with trypsin-like enzyme involvement with serum proteolysis but the lack of sequence data for the more informative smaller fragments means that the identification is not definitive. Similarly, the visual similarity is also consistent with plasmin involvement but this was not able to be confirmed by sequencing. Since serum proteolysis was more defined and limited than either plasmin or trypsin alone, this indicates that the presence of trypsin-like activity is probably much lower in serum and/or is more easily destroyed.

HLE digestion profile was also extensive but was different to serum, trypsin and plasmin. HLE is a serine elastase and cleaves predominantly at Val residues (Keil 1992). The difference between elastase digests of SHEL and SHELδ26A was more notable as most fragments, including the largest ones, were smaller in SHELδ26A, indicating that digestion was occurring preferentially from the N-terminal end which does not appear to be the case for the other enzymes or serum. HLE involvement in serum proteolysis is therefore unlikely.

Digestion with gelatinase A and gelatinase B (each previously treated with APMA) of SHEL revealed SDS-PAGE patterns of preferentially digested fragments. The banding pattern on SDS-PAGE for each of these proteases was similar, indicating that gelatinase A and gelatinase B were likely to cut at the same or identical sites. Thus the sequence specificities for these metalloproteinases were similar. These patterns differed from AMPA-treated serum, untreated serum and serine proteases. MMP-digestion revealed multiple bands. With prolonged incubation, tropoelastin displayed marked fragmentation.

In summary, by N-terminal sequencing, visual inspection of the degradation profiles by comparison with that of serum and the effect of the inhibitors the results are consistent with involvement of kallikrein and/or protease(s) capable of giving a comparable cleavage pattern, in addition to at least one other enzyme probably present at a lower level. Plasmin or another trypsin-like enzyme or combination of enzymes are the most likely to be involved in the serum digestion of SHEL. Detectable thrombin and HLE activity in serum are unlikely.

Mapping of Protease Sensitive Sites

The pattern of degradation of purified tropoelastin seen by others is similar to the sizes of peptides generated by our proteolysis experiments. The sizes seen by Mecham and Foster (1977) by their trypsin-like protease associated with tropoelastin, 57, 45, 36, 24.5 and 13–14 kDa are very similar to the number and sizes of peptides generated by serum and the individual serine proteases on both SHEL and SHELδ26A indicating that cleavage may be occurring in the same or similar places. A similar profile was seen with tropoelastin from human fibroblast cell culture (Davidson and Sephel 1987). Sequencing confirmed that one site between residues 515 and 516 was common to thrombin, kallikrein and serum and from the SDS-PAGE pattern, probably also plasmin and trypsin. All the peptides sequenced confirmed that cleavage occurred after a Lys or Arg as expected for many serine proteases (Keil 1992). However, tropoelastin contains a large number of Lys and Arg yet only a small number of these residues were actually recognised and cleaved. The fact that these same sites may be recognised by different serine proteases may be due to their accessibility and/or the surrounding amino acids.

Preferred recognition sites for kallikrein and thrombin are strongly influenced by the adjacent amino acid residues (Chang 1985; Keil 1992) but it would not have been possible a priori to predict where preferential cleavage occurs in human tropoelastin. For example, kallikrein cleaves preferentially at Arg residues preceded by a bulky residue (Keil 1992). Both sites identified by N-terminal sequencing fall into this category, with Leu-Arg at 515 and Arg—Arg at 564. However, for example, another Arg preceded by a Leu at 571 does not appear to be recognised. The highly specific and limited proteolysis of SHEL and SHELδ26A by kallikrein has allowed kallikrein treatment to be used to produce isolated C-terminal portions of tropoelastin for further study (S. Jensen and A. S. Weiss unpublished). The thrombin sites identified, however, do not fit the preferred sites for thrombin. Thrombin recognises predominantly P2-Lys/Arg-P1' where either P2 or P1' are Gly or P4-P3-Pro-Arg/Lys-P1'-P2", where P4 and P3 are hydrophobic and P1' and P2' are non-acidic residues (Chang 1985) with Arg greatly favoured over Lys (Keil 1992). Neither SHEL nor SHELδ26A contain these exact sites although the site at 152 (Lys-Pro-Lys-Ala-Pro, aa 152–156 of SEQ ID NO:4) is similar to the latter recognition site of P3-Pro-Lys-P1'-P2'. Which sites are recognised and cleaved may therefore be under the influence of tropoelastin secondary structure. Trypsin cleaves predominantly at Arg and Lys with a preference for Arg, while plasmin preferentially cleaves at Lys (Keil 1992). Since there are more Lys than Arg in tropoelastin, it would be expected that these proteases would cleave more extensively as is shown to be the case.

Protection from Degradation

Experiments have demonstrated that EBP can protect tropoelastin from degradation by binding primarily to the VGVAPG [aa 453–458 of SEQ ID NO: 4] sequence of tropoelastin (Mecham et al 1989). A peptide S-GAL which represents the elastin binding site of EBP has been used previously to model the interaction (Hinek and Rabinovitch 1994). It has been noted that S-GAL and EBP have some homology with the N-terminal sequence of proteases such as kallikrein, HLE and plasmin and are therefore proposed to bind to the same sequence in tropoelastin, thus acting as competitive inhibitors of the proteases (Hinek and Rabinovitch 1994; Hinek et al 1993). Hinek and Rabinovitch (1994) showed that S-GAL could significantly inhibit degradation of elastin by porcine pancreatic elastase and inferred that HLE and other serine proteases could be similarly inhibited from degrading tropoelastin. In this work, the use of S-GAL did not show any significant or consistent inhibition of proteolysis of SHEL or SHELδ26A by serum, trypsin, plasmin or kallikrein although some inhibition could be seen with thrombin. However, significant and reproducible inhibition was seen with HLE but complete inhibition of degradation could not be achieved, even with the large excess of S-GAL used. The S-GAL used was HPLC-purified to remove any truncated products and it may be possible that the peptide was damaged or irreversibly denatured by this process. However, samples of S-GAL which were not HPLC purified gave similar results (not shown). The mass spectroscopy data supplied by the manufacturer indicated that the correct product was synthesised. Therefore S-GAL either did not bind to SHEL or SHELδ26A very effectively or was easily displaced by the protease. Alternatively, the proteases may be binding to more than one site on tropoelastin and are therefore not effected by S-GAL.

In summary, S-GAL showed partial inhibition of tropoelastin degradation by HLE and thrombin but inhibition was not as thorough as seen by Hinek and Rabinovitch (1994) using porcine pancreatic elastase. More extensive inhibition of other proteases and serum could not be shown consistently. N-terminal sequencing data revealed one site in SHEL which was commonly recognised by thrombin, kallikrein, serum and probably trypsin and plasmin. This site and its flanking amino acids was synthesised and this SPS-peptide added to the proteolytic digests of SHEL and SHELδ26A. This peptide was not expected to bind to tropoelastin but simply act as a competitor by being recognised by the protease thus slowing degradation of SHEL and SHELδ26A. There was reproducible evidence of protection from degradation of SHEL and SHELδ26A by the presence of SPS-peptide. The amount of full-length protein was greater in the presence of SPS-peptide than in the presence of S-GAL or control digestions and was similar for both isoforms. This was most notable in the presence of low enzyme concentrations or shorter incubations and was most obvious with trypsin, plasmin, kallikrein and serum although protection from the other proteases was noted although at a reduced level. This indicates that each of the proteases and serum could recognise this peptide to some extent and therefore this is a potential inhibitor of proteolysis of tropoelastin.

There is no direct evidence that SPS-peptide is cleaved by any protease. However, the presence of a similar amount of a different peptide (S-GAL) did not exert the same effect. Thus the effect of SPS-peptide is probably not simply due to the non-specific presence of a peptide in the reaction. SPS-peptide is therefore likely to be interacting directly with the proteases (or tropoelastin) to exert its effect. SPS-peptide may allow full-length tropoelastin to persist longer in the presence of proteases, including human serum.

In summary, the inhibition of degradation of SHEL and SHELδ26A by S-GAL was only noted significantly with HLE but more extensive protection could not be shown. However a reproducible inhibition was seen in the presence of SPS-peptide with each protease and serum, and was most notable with trypsin, kallikrein and serum. This peptide provides an alternative site for interaction with proteases and results in the persistence of full-length tropoelastin for longer periods.

Proteolysis of Coacervated Tropoelastin

Coacervation of SHEL and SHELδ26A at 37° C. resulted in significant protection from proteolysis by kallikrein and thrombin and to a lesser extent by HLE, trypsin and serum. No protection was seen from attack by plasmin. The presence of 150 mM NaCl did not appear to cause the inhibition since the same reactions performed under conditions not conducive to coacervation (16° C.) were digested to a similar extent in the presence or absence of NaCl. Although it is possible that a simple change in conformation at 37° C. could result in altered proteolytic susceptibility, this is unlikely since coacervated and non-coacervated SHEL both at 37° C. were digested at different rates. The inhibition of proteolysis is therefore probably due to steric restriction in the coacervate. Of the enzymes tested, the activity of kallikrein was most significantly inhibited by coacervation. From the N-terminal sequencing results, kallikrein predominantly recognises only two sites in SHEL, both of which are in close proximity, and only one in SHELδ26A. The coacervation of tropoelastin appears to mask these sites making them less accessible to kallikrein. With thrombin, the inhibition was not as complete as with kallikrein. Thrombin recognises predominantly two sites in SHEL also but these are more distant from each other. The process of coacervation may mask these sites but if either site is slightly more accessible proteolysis would result and consequently allow easier access to the second site. Other proteases (HLE, trypsin, plasmin) and also serum recognise and cleave at many more sites within SHEL making efficient masking of all sites by coacervation unlikely and resulting in some sites remaining available for recognition and proteolysis to occur. Thus, these proteases are not as significantly inhibited by coacervation. These results indicate that in the extracellular matrix, coacervation of tropoelastin may serve an additional role to those already proposed by providing to a certain extent, protection from proteolysis including that caused by human serum. These results could be extended to the nascent elastic fibre where newly laid tropoelastin in the coacervate would be largely protected from extracellular proteases before cross-linking makes this protection essentially permanent.

Possible Consequences of Serum Degradation of Tropoelastin

It is clear from these results and those of others that serum contains factors capable of degrading tropoelastin. A number of serine proteases present in human blood have been shown here to be able to degrade tropoelastin specifically and reproducibly. Thus tropoelastin when secreted by cells into the extracellular matrix is vulnerable to extensive degradation prior to being insolubilised by lysyl oxidase and cross-linked. This is especially significant in blood vessels where damaged vessels may contain a number of these proteases during normal blood coagulation. Any tropoelastin secreted at this time and not protected, for example by EBP or by coacervation, would be fragmented. These results suggest that coacervation may indeed provide some protection from digestion as seen with the inhibition of degradation of coacervated SHEL (FIG. 13). However, protection is by no means complete. It has previously been suggested that tropoelastin may be under negative feedback autoregulation and upon accumulation in the extracellular matrix may inhibit the production of elastin mRNA (Foster and Curtiss 1990). Elastin peptides produced by proteases such as elastase have been shown to produce negative feedback inhibition when added to undamaged fibroblast cultures while stimulating tropoelastin production in protease damaged cultures (Foster et al 1990). It has been suggested that serine protease mediated proteolysis of tropoelastin may be an important modulator of tropoelastin production and that plasmin may be involved in this process (McGowan et al 1996). Our results are consistent with this proposal although the specific enzyme(s) proposed differ slightly.

It is interesting to note that most of the cleavages identified in serum occur in the C-terminal half of the tropoelastin molecule and that most of the larger fragments were from the N-terminus (FIG. 1, Table 1). Thus the action of proteases in serum on tropoelastin serves to degrade the C-terminal portion leaving a large N-terminal segment. These shortened molecules may not be incorporated into newly synthesised or growing elastic fibers due to the absence of the highly conserved C-terminus which is shown to be responsible for binding with microfibrillar proteins (Brown-Ausburger et al 1996; 1994). This is analogous to the case in supravalvular aortic stenosis, where an elastin gene truncation results in tropoelastin missing the C-terminus with the result of severe aortic disease (Ewart et al 1994). Similarly, in fetal lamb ductus arteriosis a truncated tropoelastin missing the C terminus is not incorporated into the elastic fibre (Hinek and Rabinovitch 1993). The action of serum on human tropoelastin therefore results in tropoelastin molecules which may not be rendered insolubile and may persist in the extracellular matrix. Any fibers cross-linked may be aberrant due to improper alignment, resulting in a loss of elastic properties and strength. The persistence of soluble peptides may serve to inhibit further tropoelastin production by negative feedback inhibition (Foster and Curtiss 1990). At the same time peptides are chemotactic, as demonstrated by several studies (Bisaccia et al 1994; Grosso and Scott 1993) and may serve to recruit tissue repairing cells to the site of injury, accelerating repair of the wound. Chemotactic peptides may differ in efficacy from for example SHEL and SHELδ26A.

CONCLUSION

Human serum was shown to be capable of degrading SHEL and SHELδ26A into a number of discrete fragments. This activity was confirmed to be from a serine protease and the regions of susceptibility to serum were precisely mapped by N-terminal sequencing. A number of other serine proteases were shown to be capable of degrading SHEL and SHELδ26A. From the pattern of degradation, use of selective inhibitors and N-terminal sequencing the protease responsible for serum degradation was consistent with a trypsin-like protease but kallikrein or kallikrein-like behaviour is also a likely contributor. Significant or consistent inhibition of proteolysis did not take place using S-GAL except with thrombin and HLE but reproducible inhibition was provided by SPS-peptide. However, the process of coacervation was shown to provide the most significant protection against proteolysis including by serum and was most notable for proteases which cleaved a limited number of sites.

Cleavage of SHEL and SHELδ26A with metalloproteinases to generate reproducible patterns with apparently preferred cleavage sites has also been demonstrated.

INDUSTRIAL APPLICATION

The derivatives and expression products of the invention are of use in inter alia the medical, pharmaceutical, veterinary and cosmetic fields as tissue bulking agents, and agents for cellular chemotaxis, proliferation and growth inhibition, in particular of smooth muscle cells, epithelial cells, endothelial cells, fibroblasts, osteocytes, chondrocytes and platelets.

TABLE 1

N-terminal Sequences of Protease-Produced Tropoelastin Peptides

|  | Size (kDa)* | Sequence† | [SEQ ID NO:] | Position |
|---|---|---|---|---|
| thrombin | 45 | GGVPGAIPG | aa 3–11 of SEQ ID NO:4 | |
|  | 34 | K/APGVGGAF | aa 154–162 of SEQ ID NO:4 | 152/153 |
|  | 22(19) | R/AAAGLG | aa 517–523 of SEQ ID NO:4 | 515/516 |
| kallikrein | 45 | GGVPGAIPG | aa 3–11 of SEQ ID NO:4 | |
|  | 22(19) | R/AAAGLG | aa 517–523 of SEQ ID NO:4 | 515/516 |
|  | 18(15) | R/SLSPELREGD | aa 566–523 of SEQ ID NO:4 | 564/565 |
| Trypsin | 55 | GGVPGAIPG | aa 3–11 of SEQ ID NO:4 | |
|  | 45 | GGVPGAIPG | aa 3–11 of SEQ ID NO:4 | |
|  | 40 | GGVPGAIPG | aa 3–11 of SEQ ID NO:4 | |
|  | 34 | GGVPGAIPG | aa 3–11 of SEQ ID NO:4 | |
| Plasmin | 55 | GGVPGAIP | aa 3–11 of SEQ ID NO:4 | |
|  | 45 | K/AAKAGAGL + | aa 80–88 of SEQ ID NO:4 | 78/79 |
|  | 40 | GGVPGAIP | aa 3–11 of SEQ ID NO:4 | 78/79+ |
|  | 34 | K/AAKAGAGL + | aa 80–88 of SEQ ID NO:4 | 81/82 |
|  | 28 | K/AGAGLGGV | aa 83–91 of SEQ ID NO:4 | 78/79+ |
|  |  | K/AAKAGAGL + | aa 80–88 of SEQ ID NO:4 | 81/82 |
|  |  | K/AGAGLGGV | aa 83–91 of SEQ ID NO:4 | 78/79+ |
|  |  | K/AAKAGAGL + | SEQ ID NO:102 | 81/82 |
|  |  | K/AGAGLGGV | aa 83–91 of SEQ ID NO:4 | |
| gelatinase B | 10(12) | A/LAAKAAKYGAA | SEQ ID NO:103 | 593/594 |
| Serum | 50 | GGVPGAIPGGVP | aa 3–14 of SEQ ID NO:4 | |
|  | 45 | GGVPGAIPGG | aa 3–12 of SEQ ID NO:4 | |
|  | 34 | GGVPGAIPGGVP | aa 3–14 of SEQ ID NO:4 | |
|  | 28(25) | GGVPGAIPG + | aa 3–11 of SEQ ID NO:4 | 441/442 |
|  | 27 | K/AAQFGLVPGV(?)‡ | SEQ ID NO:104 | |
|  | 25(20) | GGVPGAIPGGVPGGFYPG | SEQ ID NO:105 | 503/504 |
|  | 22(19) | GGVPGAIPG + | aa 3–11 of SEQ ID NO:4 | 515/516 |
|  | 18(15) | K/SAAKVAAKAQ(?) | 505–515 of SEQ ID NO:4 | 564/565 |

TABLE 1-continued

N-terminal Sequences of Protease-Produced Tropoelastin Peptides

| Size (kDa)* | Sequence† | [SEQ ID NO:] | Position |
|---|---|---|---|
| 13 | R/AAAGLG | | aa 517–523 of SEQ ID NO:4 |
| | R/SLSPELRE | | aa 566–574 of SEQ ID NO:4 |
| | GGVPGAIP | | aa 3–10 of SEQ ID NO:4 |

*Size of fragments are calculated from SDS-PAGE and are approximate. Sizes in brackets are the sizes determined from the position of the cleavage determined by N-terminal sequencing.
† A slash (/) indicates an internal cleavage site adjacent to an R or K residue (bold). N-terminal sequence of residues to the right of these sites was obtained allowing the precise loation of the cleavage site to be allocated and the exact size of the fragment to be calculated.
‡ A question mark (?) indicates that this designation is tentative. The peptide is likely to be present at a very low level and as a mixture with other peptides.

REFERENCES

1. Indik Z, Yeh H, Ornstein-Goldstein N, Sheppard P, Anderson N, Rosenbloom J C, Peltonen L and Rosenbloom J (1987) *PNAS* (USA) 84 5680–5684
2. Indik Z, Abrams W. R., Kucich U, Gibson C. W., Mecham R. P. and Rosenbloom J (1990) *Arch. Biochem Biophys* 280 80–86
3. Oliver L, Luvalle P A, Davidson J. M., Rosenbloom J, Mathew C. G., Betser A. J. and Boyd C. D. (1987) *Collagen Rel Res* 7 77–89
4. Sambrook J., Fritsch E. F., and Maniatis T. (1989) *Molecular Cloning: a laboratory Manual*, second edition Cold Spring Harbor Laboratory Press, Cold Spring Harbor, New York
5. Bressan G. M., Argos P. and Stanley K. K. (1987) *Biochemistry* 26 1497–11503
6. Raju K. and Anwar R. A. (1987) *J. Biol Chem* 262 5755–5762
7. Pierce R. A., Alatawi A, Deak S. B. & Boyd C. D. (1992) *Genomics* 12 651–658
8. Lipman and Pearson (1985) *Science* 227, 1435.
9. Bedell-Hogan, D., Trackman, P., Abrams, W., Rosenbloom, J. and Kagan H. (1993) *J. Biol. Chem.* 268, 10345–10350
10. Studier, F. W., Rosenberg, A. H., Dunn, J. J. and Dubendorff, J. W. (1990) *Methods Enzymol.* 185, 60–89
11. Gough, J., and Murray, N. (1983) *J. Mol. Biol.* 166, 1–19
12. Bullock, W. O., Fernandez, J. M. and Short, J. M. (1987) *BioTechniques* 5, 376–379
13. Bisaccia F, Catiglione Morelli M A, De Biasi M, Traniello S, and Tarnburro A M. (1994) *Int. J. Peptide Protein Res*, 44: 332–341
14. Chang J Y (1985) *Eur. J. Biochem.* 151: 217–224
15. Grosso L E and Scott M (1993) *Arch. Biochem. Biophys.* 305: 401–404
16. Franzblau C, Pratt C A, Faris B, Colannino N M, Offner G D, Mogayzel P J and Troxler R F (1989) *J. Biol. Chem.* 264: 15115–15119
17. Hayashi A, Wachi M and Tajima S (1995) *Biochim. Biophys. Acta* 1244: 325–330
18. Keil B (1992) Specificity of Proteolysis
19. Kobayashi J, Wigle D, Childs T, Zhu, L, Keeley F W and Rabinovitch M (1994) *J. Cell. Physiol.* 160: 121–131
20. Martin S L, Vrhovski B and Weiss A S (1995) *Gene* 154, 159–166
21. Mecham R P, Foster J A and Franzblau C (1976) *Biochim. Biophys. Acta.* 446: 245–2, 54
22. Mecham R P and Foster J A (1977) *Biochem.* 16: 3825–3831.
23. Mecham R P, Foster J A and Franzblau C (1977) *Adv. Expt. Med. Biol.* 79: 209–216
24. Rich C B and Foster J A (1984) *Biochem. J.* 217: 581–584
25. Romero N, Tinker D, Hyde D and Rucker R B (1986) *Arch. Biochem. Biophys.* 244: 161–168
26. Rucker R B (1982) *Meth. Enzym.* 82: 650–657
27. Sandberg L B and Wolt T B (1982) *Meth. Enzym.* 82: 657–665
28. Torres A R, Alvarez V L, Sandberg L B and Gray W R (1977) *Adv. Expt. Med. Biol.* 79: 267–276
29. McGowan S E, Lui R, Harvey C S and Jaeckel E C (1996) *Am. J. Physiol.* 270: L376–1385.
30. Heim R A, Pierce R A, Deak S B, Riley D J, Boyd C D and Stolle C A, (1991) *Matrix* 11: 359–366.
31. Yeh H, Ornstein-Goldstein N, Indik Z, Sheppard P, Anderson N, Rosenbloom J C, Cicila G, Yoon K and Rosenbloom J (1987) *Collagen Rel. Res.* 7: 235–237
32. Hinek A and Rabinovitch M (1994) *J. Cell Biol.* 126: 563–574.
33. Davidson J M and Sephel G C (1987) *Meth. Enzym.* 144: 214–232.
34. Mecham R P, Hinek A, Entwistle R, Wrenn D S, Griffin G L and Senior R M (1989) *Biochem.* 28: 3716–3722.
35. Foster, J. A. and Curtiss S. W. (1990) Am. J. Physio. 259: L13–L23.
36. Ewart A K, Morris C A, Atkinson D, Jin W, Sternes K, Spallone P, Stock A D, Leppert M and Keating M T (1993) *Nature Gen.* 5: 11–16.
37. Smith D B and Johnson K S (1988) *Gene* 67: 31–40.
38. Tarlton J F, Vickery C J, Leaper D J and Bailey A J (1997) *B. J. Derm.* 137: 506–516.

SEQUENCE LISTING

<160> NUMBER OF SEQ ID NOS: 106

<210> SEQ ID NO 1
<211> LENGTH: 2106
<212> TYPE: DNA
<213> ORGANISM: Homo sapiens

<400> SEQUENCE: 1

```
atgggtggcg ttccgggtgc tatcccgggt ggcgttccgg gtggtgtatt ctacccaggc      60
gcgggtctgg gtgcactggg cggtggtgcg ctgggcccgg gtggtaaacc gctgaaaccg     120
gttccaggcg gtctggcagg tgctggtctg ggtgcaggtc tgggcgcgtt cccggcggtt     180
accttcccgg gtgctctggt tccgggtggc gttgcagacg cagctgctgc gtacaaagcg     240
gcaaaggcag gtgcgggtct gggcggggta ccaggtgttg gcggtctggg tgtatctgct     300
ggcgcagttg ttccgcagcc gggtgcaggt gtaaaaccgg caaagttcc aggtgttggt      360
ctgccgggcg tatacccggg tggtgttctg ccgggcgcgc gtttcccagg tgttggtgta     420
ctgccgggcg ttccgaccgg tgcaggtgtt aaaccgaagg caccaggtgt aggcggcgcg     480
ttcgcgggta tcccgggtgt tggcccgttc ggtggtccgc agccaggcgt tccgctgggt     540
tacccgatca aagcgccgaa gcttccaggt ggctacggtc tgccgtacac caccggtaaa     600
ctgccgtacg gctacggtcc gggtggcgta gcaggtgctg cgggtaaagc aggctaccca     660
accggtactg tgttggtcc gcaggctgct gcggcagctg cggcgaaagc agcagcaaaa      720
ttcggcgcgg gtgcagcggg tgttctgccg ggcgtaggtg tgctggcgt tccgggtgtt      780
ccaggtgcga tcccgggcat cggtggtatc gcaggcgtag gtactccggc ggccgctgcg     840
gctgcggcag ctgcggcgaa agcagctaaa tacggtgcgg cagcaggcct ggttccgggt     900
ggtccaggct cggtccgggg tgttgtaggc gttccgggtg ctggtgttcc gggcgtaggt     960
gttccaggtg cgggcatccc ggttgtaccg ggtgcaggta tccgggcgc tgcggttcca    1020
ggtgttgtat cccggaagc ggcagctaag gctgctgcga agctgcgaa atacggagct      1080
cgtccgggcg ttggtgttgg tggcatcccg acctacggtg taggtgcagg cggtttccca     1140
ggtttcggcg ttggtgttgg tggcatcccg gtgtagctg tgttccgtc tgttggtggc      1200
gtaccgggtg ttggtggcgt tccaggtgta ggtatctccc cggaagcgca ggcagctgcg    1260
gcagctaaag cagcgaagta cggcgttggt actccggcgg cagcagctgc taaagcagcg    1320
gctaaagcag cgcagttcgg actagttccg gcgtaggtg ttgcgccagg tgttggcgta     1380
gcaccgggtg ttggtgttgc tccgggcgta ggtctggcac cgggtgttgg cgttgcacca    1440
ggtgtaggtg ttgcgccggg cgttggtgta gcaccgggta tcggtccggg tggcgttgcg    1500
gctgctgcga atctgctgc gaaggttgct gcgaaagcgc agctgcgtgc agcagctggt    1560
ctgggtgcgg gcatcccagg tctgggtgta ggtgttggtg ttccgggcct gggtgtaggt    1620
gcagggtac cggcctggg tgttggtgca ggcgttccgg gtttcggtgc tgttccgggc      1680
gcgctggctg ctgcgaaagc ggcgaaatac ggtgcagcgg ttccgggtgt actgggcggt    1740
ctgggtgctc tgggcggtgt tggtatcccg ggcggtgttg taggtgcagg cccagctgca    1800
gctgctgctg cggcaaaggc agcggcgaaa gcagctcagt tcggtctggt tggtgcagca    1860
ggtctgggcg gtctgggtgt tggcggtctg ggtgtaccgg gcgttggtgg tctgggtggc    1920
atcccgccgg cggcggcagc taaagcggct aaatacggtg cagcaggtct gggtggcgtt    1980
ctgggtggtg ctggtcagtt cccactgggc ggtgtagcgg cacgtccggg tttcggtctg    2040
tccccgatct tcccaggcgg tgcatgcctg ggtaaagctt gcggccgtaa acgtaaataa    2100
tgatag                                                                2106
```

<210> SEQ ID NO 2
<211> LENGTH: 1992
<212> TYPE: DNA

<213> ORGANISM: Homo sapiens

<400> SEQUENCE: 2

| | | | | | |
|---|---|---|---|---|---|
| atgggtggcg | ttccgggtgc | tgttccgggt | ggcgttccgg | gtggtgtatt | ctacccaggc | 60 |
| gcgggtttcg | gtgctgttcc | gggtggcgtt | gcagacgcag | ctgctgcgta | caaagcggca | 120 |
| aaggcaggtg | cgggtctggg | cggggtacca | ggtgttggcg | gtctgggtgt | atctgctggc | 180 |
| gcagttgttc | cgcagccggg | tgcaggtgta | aaaccgggca | agttccaggt | gttggtctg | 240 |
| ccgggcgtat | acccgggttt | cggtgctgtt | ccgggcgcgc | gtttcccagg | tgttggtgta | 300 |
| ctgccgggcg | ttccgaccgg | tgcaggtgtt | aaaccgaagg | caccaggtgt | aggcggcgcg | 360 |
| ttcgcgggta | tcccgggtgt | tggcccgttc | ggtggtccgc | agccaggcgt | tccgctgggt | 420 |
| tacccgatca | aagcgccgaa | gcttccaggt | ggctacggtc | tgccgtacac | caccggtaaa | 480 |
| ctgccgtacg | gctacggtcc | gggtggcgta | gcaggtgctg | cgggtaaagc | aggctaccca | 540 |
| accggtactg | tgttggtcc | gcaggctgct | gcggcagctg | cggcgaaggc | agcagcaaaa | 600 |
| ttcggcgcgg | gtgcagcggg | tttcggtgct | gttccgggcg | taggtggtgc | tggcgttccg | 660 |
| ggtgttccag | gtgcgatccc | gggcatcggt | ggtatcgcag | gctaggtac | tccggcggcc | 720 |
| gctgcggctg | cggcagctgc | ggcgaaagca | gctaaatacg | gtgcggcagc | aggcctggtt | 780 |
| ccgggtggtc | caggcttcgg | tccgggtgtt | gtaggcgttc | cgggtttcgg | tgctgttccg | 840 |
| ggcgtaggtg | ttccaggtgc | gggcatcccg | gttgtaccgg | gtgcaggtat | cccgggcgct | 900 |
| gcgggtttcg | gtgctgtatc | cccggaagcg | gcagctaagg | ctgctgcgaa | agctgcgaaa | 960 |
| tacggagctc | gtccgggcgt | tggtgttggt | ggcatcccga | cctacggtgt | aggtgcaggc | 1020 |
| ggtttcccag | gtttcggcgt | tggtgttggt | ggcatcccgg | gtgtagctgg | tgttccgtct | 1080 |
| gttggtggcg | taccgggtgt | tggtggcgtt | ccaggtgtag | gtatctcccc | ggaagcgcag | 1140 |
| gcagctgcgg | cagctaaagc | agcgaagtac | ggcgttggta | ctccggcggc | agcagctgct | 1200 |
| aaagcagcgg | ctaaagcagc | gcagttcgga | ctagttccgg | gcgtaggtgt | tgcgccaggt | 1260 |
| gttggcgtag | caccgggtgt | tggtgttgct | ccgggcgtag | gtctggcacc | gggtgttggc | 1320 |
| gttgcaccag | gtgtaggtgt | tgcgccgggc | gttggtgtag | caccgggtat | cggtccgggt | 1380 |
| ggcgttgcgg | ctgctgcgaa | atctgctgcg | aaggttgctg | cgaaagcgca | gctgcgtgca | 1440 |
| gcagctggtc | tgggtgcggg | catcccaggt | ctgggtgtag | gtgttggtgt | tccgggcctg | 1500 |
| ggtgtaggtg | caggggtacc | gggcctgggt | gttggtgcag | gcgttccggg | tttcggtgct | 1560 |
| gttccgggcg | cgctggctgc | tgcgaaagcg | gcgaaatacg | gtgctgttcc | gggtgtactg | 1620 |
| ggcggtctgg | gtgctctggg | cggtgttggt | atcccgggcg | gtgttgtagg | tgcaggccca | 1680 |
| gctgcagctg | ctgctgcggc | aaaggcagcg | gcgaaagcag | ctcagttcgg | tctgttggt | 1740 |
| gcagcaggtc | tgggcggtct | gggtgttggc | ggtctgggtg | taccgggcgt | tggtggtctg | 1800 |
| ggtggcatcc | cgccggcggc | ggcagctaaa | gcggctaaat | acggtgcagc | aggtctgggt | 1860 |
| ggcgttctgg | gtggtgctgg | tcagttccca | ctgggcggtg | tagcggcacg | tccgggtttc | 1920 |
| ggtctgtccc | cgatcttccc | aggcggtgca | tgcctgggta | aagcttgcgg | ccgtaaacgt | 1980 |
| aaataatgat | ag | | | | | 1992 |

<210> SEQ ID NO 3
<211> LENGTH: 2210
<212> TYPE: DNA
<213> ORGANISM: Homo sapiens
<220> FEATURE:
<221> NAME/KEY: CDS -continued

<222> LOCATION: (9)..(2201)

<400> SEQUENCE: 3

| | | | | | | | | | | | | | | | |
|---|---|---|---|---|---|---|---|---|---|---|---|---|---|---|---|
| gatccatg | ggt | ggc | gtt | ccg | ggt | gct | atc | ccg | ggt | ggc | gtt | ccg | ggt | ggt | 50 |
| | Gly | Gly | Val | Pro | Gly | Ala | Ile | Pro | Gly | Gly | Val | Pro | Gly | Gly | |
| | 1 | | | 5 | | | | | 10 | | | | | | |

| gta | ttc | tac | cca | ggc | gcg | ggt | ctg | ggt | gca | ctg | ggc | ggt | ggt | gcg | ctg | 98 |
|---|---|---|---|---|---|---|---|---|---|---|---|---|---|---|---|---|
| Val | Phe | Tyr | Pro | Gly | Ala | Gly | Leu | Gly | Ala | Leu | Gly | Gly | Gly | Ala | Leu | |
| 15 | | | | 20 | | | | | 25 | | | | | | 30 | |

| ggc | ccg | ggt | ggt | aaa | ccg | ctg | aaa | ccg | gtt | cca | ggt | ctg | gca | ggt | 146 |
|---|---|---|---|---|---|---|---|---|---|---|---|---|---|---|---|
| Gly | Pro | Gly | Gly | Lys | Pro | Leu | Lys | Pro | Val | Pro | Gly | Leu | Ala | Gly | |
| | | | 35 | | | | | 40 | | | | | 45 | | |

| gct | ggt | ctg | ggt | gca | ggt | ctg | ggc | gcg | ttc | ccg | gcg | gtt | acc | ttc | ccg | 194 |
|---|---|---|---|---|---|---|---|---|---|---|---|---|---|---|---|---|
| Ala | Gly | Leu | Gly | Ala | Gly | Leu | Gly | Ala | Phe | Pro | Ala | Val | Thr | Phe | Pro | |
| | | 50 | | | | | 55 | | | | | 60 | | | | |

| ggt | gct | ctg | gtt | ccg | ggt | ggc | gtt | gca | gac | gca | gct | gct | gcg | tac | aaa | 242 |
|---|---|---|---|---|---|---|---|---|---|---|---|---|---|---|---|---|
| Gly | Ala | Leu | Val | Pro | Gly | Gly | Val | Ala | Asp | Ala | Ala | Ala | Ala | Tyr | Lys | |
| | 65 | | | | | 70 | | | | | 75 | | | | | |

| gcg | gca | aag | gca | ggt | gcg | ggt | ctg | ggc | ggg | gta | cca | ggt | gtt | ggc | ggt | 290 |
|---|---|---|---|---|---|---|---|---|---|---|---|---|---|---|---|---|
| Ala | Ala | Lys | Ala | Gly | Ala | Gly | Leu | Gly | Gly | Val | Pro | Gly | Val | Gly | Gly | |
| 80 | | | | | 85 | | | | | 90 | | | | | | |

| ctg | ggt | gta | tct | gct | ggc | gca | gtt | gtt | ccg | cag | ccg | ggt | gca | ggt | gta | 338 |
|---|---|---|---|---|---|---|---|---|---|---|---|---|---|---|---|---|
| Leu | Gly | Val | Ser | Ala | Gly | Ala | Val | Val | Pro | Gln | Pro | Gly | Ala | Gly | Val | |
| 95 | | | | 100 | | | | | 105 | | | | | 110 | | |

| aaa | ccg | ggc | aaa | gtt | cca | ggt | gtt | ggt | ctg | ccg | ggc | gta | tac | ccg | ggt | 386 |
|---|---|---|---|---|---|---|---|---|---|---|---|---|---|---|---|---|
| Lys | Pro | Gly | Lys | Val | Pro | Gly | Val | Gly | Leu | Pro | Gly | Val | Tyr | Pro | Gly | |
| | | | 115 | | | | | 120 | | | | | 125 | | | |

| ggt | gtt | ctg | ccg | ggc | gcg | cgt | ttc | cca | ggt | gtt | ggt | gta | ctg | ccg | ggc | 434 |
|---|---|---|---|---|---|---|---|---|---|---|---|---|---|---|---|---|
| Gly | Val | Leu | Pro | Gly | Ala | Arg | Phe | Pro | Gly | Val | Gly | Val | Leu | Pro | Gly | |
| | | 130 | | | | | 135 | | | | | 140 | | | | |

| gtt | ccg | acc | ggt | gca | ggt | gtt | aaa | ccg | aag | gca | cca | ggt | gta | ggc | ggc | 482 |
|---|---|---|---|---|---|---|---|---|---|---|---|---|---|---|---|---|
| Val | Pro | Thr | Gly | Ala | Gly | Val | Lys | Pro | Lys | Ala | Pro | Gly | Val | Gly | Gly | |
| | | 145 | | | | | 150 | | | | | 155 | | | | |

| gcg | ttc | gcg | ggt | atc | ccg | ggt | gtt | ggc | ccg | ttc | ggt | ggt | ccg | cag | cca | 530 |
|---|---|---|---|---|---|---|---|---|---|---|---|---|---|---|---|---|
| Ala | Phe | Ala | Gly | Ile | Pro | Gly | Val | Gly | Pro | Phe | Gly | Gly | Pro | Gln | Pro | |
| | 160 | | | | | 165 | | | | | 170 | | | | | |

| ggc | gtt | ccg | ctg | ggt | tac | ccg | atc | aaa | gcg | ccg | aag | ctt | cca | ggt | ggc | 578 |
|---|---|---|---|---|---|---|---|---|---|---|---|---|---|---|---|---|
| Gly | Val | Pro | Leu | Gly | Tyr | Pro | Ile | Lys | Ala | Pro | Lys | Leu | Pro | Gly | Gly | |
| 175 | | | | 180 | | | | | 185 | | | | | 190 | | |

| tac | ggt | ctg | ccg | tac | acc | acc | ggt | aaa | ctg | ccg | tac | ggc | tac | ggt | ccg | 626 |
|---|---|---|---|---|---|---|---|---|---|---|---|---|---|---|---|---|
| Tyr | Gly | Leu | Pro | Tyr | Thr | Thr | Gly | Lys | Leu | Pro | Tyr | Gly | Tyr | Gly | Pro | |
| | | | 195 | | | | | 200 | | | | | 205 | | | |

| ggc | ggc | gta | gca | ggt | gct | gcg | ggt | aaa | gca | ggc | tac | cca | acc | ggt | act | 674 |
|---|---|---|---|---|---|---|---|---|---|---|---|---|---|---|---|---|
| Gly | Gly | Val | Ala | Gly | Ala | Ala | Gly | Lys | Ala | Gly | Tyr | Pro | Thr | Gly | Thr | |
| | | 210 | | | | | 215 | | | | | 220 | | | | |

| ggt | gtt | ggt | ccg | cag | gct | gct | gcg | gca | gct | gcg | gcg | aag | gca | gca | gca | 722 |
|---|---|---|---|---|---|---|---|---|---|---|---|---|---|---|---|---|
| Gly | Val | Gly | Pro | Gln | Ala | Ala | Ala | Ala | Ala | Ala | Ala | Lys | Ala | Ala | Ala | |
| | 225 | | | | | 230 | | | | | 235 | | | | | |

| aaa | ttc | ggc | gcg | ggt | gca | gcg | ggt | gtt | ctg | ccg | ggc | gta | ggt | ggt | gct | 770 |
|---|---|---|---|---|---|---|---|---|---|---|---|---|---|---|---|---|
| Lys | Phe | Gly | Ala | Gly | Ala | Ala | Gly | Val | Leu | Pro | Gly | Val | Gly | Gly | Ala | |
| | 240 | | | | | 245 | | | | | 250 | | | | | |

| ggc | gtt | ccg | ggt | gtt | cca | ggt | gcg | atc | ccg | ggc | atc | ggt | ggt | atc | gca | 818 |
|---|---|---|---|---|---|---|---|---|---|---|---|---|---|---|---|---|
| Gly | Val | Pro | Gly | Val | Pro | Gly | Ala | Ile | Pro | Gly | Ile | Gly | Gly | Ile | Ala | |
| 255 | | | | 260 | | | | | 265 | | | | | 270 | | |

| ggc | gta | ggt | act | ccg | gcg | gcc | gct | gcg | gct | gca | gct | gcg | gcg | aaa | 866 |
|---|---|---|---|---|---|---|---|---|---|---|---|---|---|---|---|
| Gly | Val | Gly | Thr | Pro | Ala | Ala | Ala | Ala | Ala | Ala | Ala | Ala | Ala | Lys | |
| | | | 275 | | | | | 280 | | | | | 285 | | |

| gca | gct | aaa | tac | ggt | gcg | gca | gca | ggc | ctg | gtt | ccg | ggt | ggt | cca | ggc | 914 |
|---|---|---|---|---|---|---|---|---|---|---|---|---|---|---|---|---|
| Ala | Ala | Lys | Tyr | Gly | Ala | Ala | Ala | Gly | Leu | Val | Pro | Gly | Gly | Pro | Gly | |
| | | 290 | | | | | 295 | | | | | 300 | | | | |

-continued

| | | |
|---|---|---|
| ttc ggt ccg ggt gtt gta ggc gtt ccg ggt gct ggt gtt ccg ggc gta<br>Phe Gly Pro Gly Val Val Gly Val Pro Gly Ala Gly Val Pro Gly Val<br>        305                    310                  315 | 962 |
| ggt gtt cca ggt gcg ggc atc ccg gtt gta ccg ggt gca ggt atc ccg<br>Gly Val Pro Gly Ala Gly Ile Pro Val Val Pro Gly Ala Gly Ile Pro<br>320                    325                    330 | 1010 |
| ggc gct gcg gtt cca ggt gtt gta tcc ccg gaa gcg gca gct aag gct<br>Gly Ala Ala Val Pro Gly Val Val Ser Pro Glu Ala Ala Ala Lys Ala<br>335                    340                    345                  350 | 1058 |
| gct gcg aaa gct gcg aaa tac gga gct cgt ccg ggc gtt ggt gtt ggt<br>Ala Ala Lys Ala Ala Lys Tyr Gly Ala Arg Pro Gly Val Gly Val Gly<br>                  355                    360                  365 | 1106 |
| ggc atc ccg acc tac ggt gta ggt gca ggc ggt ttc cca ggt ttc ggc<br>Gly Ile Pro Thr Tyr Gly Val Gly Ala Gly Gly Phe Pro Gly Phe Gly<br>            370                    375                  380 | 1154 |
| gtt ggt gtt ggt ggc atc ccg ggt gta gct ggt gtt ccg tct gtt ggt<br>Val Gly Val Gly Gly Ile Pro Gly Val Ala Gly Val Pro Ser Val Gly<br>385                    390                    395 | 1202 |
| ggc gta ccg ggt gtt ggt ggc gtt cca ggt gta ggt atc tcc ccg gaa<br>Gly Val Pro Gly Val Gly Gly Val Pro Gly Val Gly Ile Ser Pro Glu<br>400                    405                    410 | 1250 |
| gcg cag gca gct gcg gca gct aaa gca gcg aag tac ggc gtt ggt act<br>Ala Gln Ala Ala Ala Ala Lys Ala Ala Lys Tyr Gly Val Gly Thr<br>415                    420                    425                  430 | 1298 |
| ccg gcg gca gca gct gct aaa gca gcg gct aaa gca gcg cag ttc gga<br>Pro Ala Ala Ala Ala Ala Lys Ala Ala Lys Ala Ala Gln Phe Gly<br>                  435                    440                  445 | 1346 |
| cta gtt ccg ggc gta ggt gtt gcg cca ggt gtt ggc gta gca ccg ggt<br>Leu Val Pro Gly Val Gly Val Ala Pro Gly Val Gly Val Ala Pro Gly<br>            450                    455                  460 | 1394 |
| gtt ggt gtt gct ccg ggc gta ggt ctg gca ccg ggt gtt ggc gtt gca<br>Val Gly Val Ala Pro Gly Val Gly Leu Ala Pro Gly Val Gly Val Ala<br>465                    470                    475 | 1442 |
| cca ggt gta ggt gtt gcg ccg ggc gtt ggt gta gca ccg ggt atc ggt<br>Pro Gly Val Gly Val Ala Pro Gly Val Gly Val Ala Pro Gly Ile Gly<br>480                    485                    490 | 1490 |
| ccg ggt ggc gtt gcg gct gct gcg aaa tct gct gcg aag gtt gct gcg<br>Pro Gly Gly Val Ala Ala Ala Ala Lys Ser Ala Ala Lys Val Ala Ala<br>495                    500                    505                  510 | 1538 |
| aaa gcg cag ctg cgt gca gca gct ggt ctg ggt gcg ggc atc cca ggt<br>Lys Ala Gln Leu Arg Ala Ala Ala Gly Leu Gly Ala Gly Ile Pro Gly<br>                  515                    520                  525 | 1586 |
| ctg ggt gta ggt gtt ggt gtt ccg ggc ctg ggt gta ggt gca ggg gta<br>Leu Gly Val Gly Val Gly Val Pro Gly Leu Gly Val Gly Ala Gly Val<br>            530                    535                  540 | 1634 |
| ccg ggc ctg ggt gtt ggt gca ggc gtt ccg ggt ttc ggt gct ggc gcg<br>Pro Gly Leu Gly Val Gly Ala Gly Val Pro Gly Phe Gly Ala Gly Ala<br>545                    550                    555 | 1682 |
| gac gaa ggt gta cgt cgt tcc ctg tct cca gaa ctg cgt gaa ggt gac<br>Asp Glu Gly Val Arg Arg Ser Leu Ser Pro Glu Leu Arg Glu Gly Asp<br>560                    565                    570 | 1730 |
| ccg tcc tct tcc cag cac ctg ccg tct acc ccg tcc tct cca cgt gtt<br>Pro Ser Ser Ser Gln His Leu Pro Ser Thr Pro Ser Ser Pro Arg Val<br>575                    580                    585                  590 | 1778 |
| ccg ggc gcg ctg gct gct gcg aaa gcg gcg aaa tac ggt gca gcg gtt<br>Pro Gly Ala Leu Ala Ala Ala Lys Ala Ala Lys Tyr Gly Ala Ala Val<br>                  595                    600                  605 | 1826 |
| ccg ggt gta ctg ggc ggt ctg ggt gct ctg ggc ggt gtt ggt atc ccg<br>Pro Gly Val Leu Gly Gly Leu Gly Ala Leu Gly Gly Val Gly Ile Pro | 1874 |

-continued

```
                610                615                620
ggc ggt gtt gta ggt gca ggc cca gct gca gct gct gcg gca aag    1922
Gly Gly Val Gly Ala Gly Pro Ala Ala Ala Ala Ala Ala Lys
            625                630                635 gca gcg gcg aaa gca gct cag ttc ggt ctg gtt ggt gca gca ggt ctg    1970
Ala Ala Ala Lys Ala Ala Gln Phe Gly Leu Val Gly Ala Ala Gly Leu
        640                645                650 ggc ggt ctg ggt gtt ggc ggt ctg ggt gta ccg ggc gtt ggt ggt ctg    2018
Gly Gly Leu Gly Val Gly Gly Leu Gly Val Pro Gly Val Gly Gly Leu
655                660                665                670 ggt ggc atc ccg ccg gcg gcg gca gct aaa gcg gct aaa tac ggt gca    2066
Gly Gly Ile Pro Pro Ala Ala Ala Ala Lys Ala Ala Lys Tyr Gly Ala
                675                680                685 gca ggt ctg ggt ggc gtt ctg ggt ggt gct ggt cag ttc cca ctg ggc    2114
Ala Gly Leu Gly Gly Val Leu Gly Gly Ala Gly Gln Phe Pro Leu Gly
            690                695                700 ggt gta gcg gca cgt ccg ggt ttc ggt ctg tcc ccg atc ttc cca ggc    2162
Gly Val Ala Ala Arg Pro Gly Phe Gly Leu Ser Pro Ile Phe Pro Gly
        705                710                715 ggt gca tgc ctg ggt aaa gct tgc ggc cgt aaa cgt aaa taatgatag    2210
Gly Ala Cys Leu Gly Lys Ala Cys Gly Arg Lys Arg Lys
720                725                730
```

<210> SEQ ID NO 4
<211> LENGTH: 731
<212> TYPE: PRT
<213> ORGANISM: Homo sapiens

<400> SEQUENCE: 4

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
210                 215                 220
```

```
Gly Pro Gln Ala Ala Ala Ala Ala Lys Ala Ala Lys Phe
225                 230                 235                 240

Gly Ala Gly Ala Ala Gly Val Leu Pro Gly Val Gly Ala Gly Val
                245                 250                 255

Pro Gly Val Pro Gly Ala Ile Pro Gly Ile Gly Ile Ala Gly Val
                260                 265                 270

Gly Thr Pro Ala Ala Ala Ala Ala Ala Ala Ala Lys Ala Ala
        275                 280                 285

Lys Tyr Gly Ala Ala Ala Gly Leu Val Pro Gly Pro Gly Phe Gly
        290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Lys Ala Ala Ala
                340                 345                 350

Lys Ala Ala Lys Tyr Gly Ala Arg Pro Gly Val Gly Val Gly Gly Ile
                355                 360                 365

Pro Thr Tyr Gly Val Gly Ala Gly Gly Phe Pro Gly Phe Gly Val Gly
        370                 375                 380

Val Gly Gly Ile Pro Gly Val Ala Gly Val Pro Ser Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Val Gly Thr Pro Ala
                420                 425                 430

Ala Ala Ala Lys Ala Ala Ala Lys Ala Ala Gln Phe Gly Leu Val
        435                 440                 445

Pro Gly Val Gly Val Ala Pro Gly Val Gly Val Ala Pro Gly Val Gly
        450                 455                 460

Val Ala Pro Gly Val Gly Leu Ala Pro Gly Val Gly Val Ala Pro Gly
465                 470                 475                 480

Val Gly Val Ala Pro Gly Val Gly Val Ala Pro Gly Ile Gly Pro Gly
                485                 490                 495

Gly Val Ala Ala Ala Lys Ser Ala Ala Lys Val Ala Ala Lys Ala
                500                 505                 510

Gln Leu Arg Ala Ala Ala Gly Leu Gly Ala Gly Ile Pro Gly Leu Gly
        515                 520                 525

Val Gly Val Gly Val Pro Gly Leu Gly Val Gly Ala Gly Val Pro Gly
        530                 535                 540

Leu Gly Val Gly Ala Gly Val Pro Gly Phe Gly Ala Gly Ala Asp Glu
545                 550                 555                 560

Gly Val Arg Arg Ser Leu Ser Pro Glu Leu Arg Glu Gly Asp Pro Ser
                565                 570                 575

Ser Ser Gln His Leu Pro Ser Thr Pro Ser Ser Pro Arg Val Pro Gly
                580                 585                 590

Ala Leu Ala Ala Ala Lys Ala Ala Lys Tyr Gly Ala Ala Val Pro Gly
        595                 600                 605

Val Leu Gly Gly Leu Gly Ala Leu Gly Gly Val Gly Ile Pro Gly Gly
        610                 615                 620

Val Val Gly Ala Gly Pro Ala Ala Ala Ala Ala Ala Ala Lys Ala Ala
625                 630                 635                 640
```

-continued

```
Ala Lys Ala Ala Gln Phe Gly Leu Val Gly Ala Ala Gly Leu Gly Gly
                645                 650                 655

Leu Gly Val Gly Gly Leu Gly Val Pro Gly Val Gly Gly Leu Gly Gly
            660                 665                 670

Ile Pro Pro Ala Ala Ala Lys Ala Ala Lys Tyr Gly Ala Ala Gly
                675                 680                 685

Leu Gly Gly Val Leu Gly Gly Ala Gln Phe Pro Leu Gly Gly Val
            690                 695                 700

Ala Ala Arg Pro Gly Phe Gly Leu Ser Pro Ile Phe Pro Gly Gly Ala
705                 710                 715                 720

Cys Leu Gly Lys Ala Cys Gly Arg Lys Arg Lys
                725                 730
```

<210> SEQ ID NO 5
<211> LENGTH: 698
<212> TYPE: PRT
<213> ORGANISM: Homo sapiens

<400> SEQUENCE: 5

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
                20                  25                  30

Gly Gly Lys Pro Leu Lys Pro Val Pro Gly Gly Leu Ala Gly Ala Gly
                35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
                100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
        130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
            210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Lys Ala Ala
            275                 280                 285
```

```
Lys Tyr Gly Ala Ala Gly Leu Val Pro Gly Gly Pro Gly Phe Gly
    290                 295                 300
Pro Gly Val Val Gly Val Pro Gly Ala Gly Val Pro Gly Val Gly Val
305                 310                 315                 320
Pro Gly Ala Gly Ile Pro Val Val Pro Gly Ala Gly Ile Pro Gly Ala
                325                 330                 335
Ala Val Pro Gly Val Val Ser Pro Glu Ala Ala Lys Ala Ala Ala
                340                 345                 350
Lys Ala Ala Lys Tyr Gly Ala Arg Pro Gly Val Gly Val Gly Gly Ile
                355                 360                 365
Pro Thr Tyr Gly Val Gly Ala Gly Gly Phe Pro Gly Phe Gly Val Gly
    370                 375                 380
Val Gly Gly Ile Pro Gly Val Ala Gly Val Pro Ser Val Gly Gly Val
385                 390                 395                 400
Pro Gly Val Gly Gly Val Pro Gly Val Gly Ile Ser Pro Glu Ala Gln
                405                 410                 415
Ala Ala Ala Ala Ala Lys Ala Ala Lys Tyr Gly Val Gly Thr Pro Ala
                420                 425                 430
Ala Ala Ala Ala Lys Ala Ala Ala Lys Ala Ala Gln Phe Gly Leu Val
                435                 440                 445
Pro Gly Val Gly Val Ala Pro Gly Val Gly Val Ala Pro Gly Val Gly
    450                 455                 460
Val Ala Pro Gly Val Gly Leu Ala Pro Gly Val Gly Val Ala Pro Gly
465                 470                 475                 480
Val Gly Val Ala Pro Gly Val Gly Val Ala Pro Gly Ile Gly Pro Gly
                485                 490                 495
Gly Val Ala Ala Ala Lys Ser Ala Ala Lys Val Ala Ala Lys Ala
                500                 505                 510
Gln Leu Arg Ala Ala Gly Leu Gly Ala Gly Ile Pro Gly Leu Gly
    515                 520                 525
Val Gly Val Gly Val Pro Gly Leu Gly Val Gly Ala Gly Val Pro Gly
    530                 535                 540
Leu Gly Val Gly Ala Gly Val Pro Gly Phe Gly Ala Val Pro Gly Ala
545                 550                 555                 560
Leu Ala Ala Ala Lys Ala Ala Lys Tyr Gly Ala Ala Val Pro Gly Val
                565                 570                 575
Leu Gly Gly Leu Gly Ala Leu Gly Gly Val Gly Ile Pro Gly Gly Val
                580                 585                 590
Val Gly Ala Gly Pro Ala Ala Ala Ala Ala Ala Lys Ala Ala Ala
    595                 600                 605
Lys Ala Ala Gln Phe Gly Leu Val Gly Ala Ala Gly Leu Gly Gly Leu
    610                 615                 620
Gly Val Gly Gly Leu Gly Val Pro Gly Val Gly Gly Leu Gly Gly Ile
625                 630                 635                 640
Pro Pro Ala Ala Ala Ala Lys Ala Ala Lys Tyr Gly Ala Ala Gly Leu
                645                 650                 655
Gly Gly Val Leu Gly Gly Ala Gly Gln Phe Pro Leu Gly Gly Val Ala
                660                 665                 670
Ala Arg Pro Gly Phe Gly Leu Ser Pro Ile Phe Pro Gly Gly Ala Cys
                675                 680                 685
Leu Gly Lys Ala Cys Gly Arg Lys Arg Lys
    690                 695
```

<210> SEQ ID NO 6
<211> LENGTH: 661
<212> TYPE: PRT
<213> ORGANISM: Homo sapiens

<400> SEQUENCE: 6

```
Met Gly Gly Val Pro Gly Ala Val Pro Gly Gly Val Pro Gly Gly Val
1               5                   10                  15

Phe Tyr Pro Gly Ala Gly Phe Gly Ala Val Pro Gly Gly Val Ala Asp
            20                  25                  30

Ala Ala Ala Ala Tyr Lys Ala Ala Lys Ala Gly Ala Gly Leu Gly Gly
        35                  40                  45

Val Pro Gly Val Gly Gly Leu Gly Val Ser Ala Gly Ala Val Val Pro
    50                  55                  60

Gln Pro Gly Ala Gly Val Lys Pro Gly Lys Val Pro Gly Val Gly Leu
65                  70                  75                  80

Pro Gly Val Tyr Pro Gly Phe Gly Ala Val Pro Gly Ala Arg Phe Pro
                85                  90                  95

Gly Val Gly Val Leu Pro Gly Val Pro Thr Gly Ala Gly Val Lys Pro
            100                 105                 110

Lys Ala Pro Gly Val Gly Gly Ala Phe Ala Gly Ile Pro Gly Val Gly
        115                 120                 125

Pro Phe Gly Gly Pro Gln Pro Gly Val Pro Leu Gly Tyr Pro Ile Lys
    130                 135                 140

Ala Pro Lys Leu Pro Gly Gly Tyr Gly Leu Pro Tyr Thr Thr Gly Lys
145                 150                 155                 160

Leu Pro Tyr Gly Tyr Gly Pro Gly Gly Val Ala Gly Ala Ala Gly Lys
                165                 170                 175

Ala Gly Tyr Pro Thr Gly Thr Gly Val Gly Pro Gln Ala Ala Ala Ala
            180                 185                 190

Ala Ala Ala Lys Ala Ala Ala Lys Phe Gly Ala Gly Ala Ala Gly Phe
        195                 200                 205

Gly Ala Val Pro Gly Val Gly Gly Ala Gly Val Pro Gly Val Pro Gly
    210                 215                 220

Ala Ile Pro Gly Ile Gly Gly Ile Ala Gly Val Gly Thr Pro Ala Ala
225                 230                 235                 240

Ala Ala Ala Ala Ala Ala Ala Lys Ala Ala Lys Tyr Gly Ala Ala Ala
                245                 250                 255

Ala Gly Leu Val Pro Gly Gly Pro Gly Phe Gly Pro Gly Val Val Gly
            260                 265                 270

Val Pro Gly Phe Gly Ala Val Pro Gly Val Val Pro Gly Ala Gly
                275                 280                 285

Ile Pro Val Val Pro Gly Ala Gly Ile Pro Gly Ala Ala Gly Phe Gly
    290                 295                 300

Ala Val Ser Pro Glu Ala Ala Ala Lys Ala Ala Lys Ala Ala Ala Lys
305                 310                 315                 320

Tyr Gly Ala Arg Pro Gly Val Gly Val Gly Ile Pro Thr Tyr Gly
                325                 330                 335

Val Gly Ala Gly Gly Phe Pro Gly Phe Gly Val Gly Val Gly Gly Ile
            340                 345                 350

Pro Gly Val Ala Gly Val Pro Ser Val Gly Gly Val Pro Gly Val Gly
        355                 360                 365

Gly Val Pro Gly Val Gly Ile Ser Pro Glu Ala Gln Ala Ala Ala Ala
    370                 375                 380
```

```
Ala Lys Ala Ala Lys Tyr Gly Val Gly Thr Pro Ala Ala Ala Ala
385                 390                 395                 400

Lys Ala Ala Lys Ala Ala Gln Phe Gly Leu Val Pro Gly Val Gly
                405                 410                 415

Val Ala Pro Gly Val Gly Val Ala Pro Gly Val Gly Val Ala Pro Gly
            420                 425                 430

Val Gly Leu Ala Pro Gly Val Ala Pro Gly Val Gly Val Ala
            435                 440                 445

Pro Gly Val Gly Val Ala Pro Gly Ile Gly Pro Gly Val Ala Ala
            450                 455                 460

Ala Ala Lys Ser Ala Ala Lys Val Ala Lys Ala Gln Leu Arg Ala
465                 470                 475                 480

Ala Ala Gly Leu Gly Ala Gly Ile Pro Gly Leu Gly Val Gly Val Gly
                485                 490                 495

Val Pro Gly Leu Gly Val Gly Ala Gly Val Pro Gly Leu Gly Val Gly
            500                 505                 510

Ala Gly Val Pro Gly Phe Gly Ala Val Pro Gly Ala Leu Ala Ala Ala
            515                 520                 525

Lys Ala Ala Lys Tyr Gly Ala Val Pro Gly Val Leu Gly Gly Leu Gly
530                 535                 540

Ala Leu Gly Gly Val Gly Ile Pro Gly Gly Val Val Gly Ala Gly Pro
545                 550                 555                 560

Ala Ala Ala Ala Ala Ala Lys Ala Ala Lys Ala Ala Gln Phe
                565                 570                 575

Gly Leu Val Gly Ala Ala Gly Leu Gly Gly Leu Gly Val Gly Gly Leu
                580                 585                 590

Gly Val Pro Gly Val Gly Gly Leu Gly Gly Ile Pro Pro Ala Ala Ala
            595                 600                 605

Ala Lys Ala Ala Lys Tyr Gly Ala Ala Gly Leu Gly Gly Val Leu Gly
            610                 615                 620

Gly Ala Gly Gln Phe Pro Leu Gly Gly Val Ala Ala Arg Pro Gly Phe
625                 630                 635                 640

Gly Leu Ser Pro Ile Phe Pro Gly Gly Ala Cys Leu Gly Lys Ala Cys
                645                 650                 655

Gly Arg Lys Arg Lys
            660

<210> SEQ ID NO 7
<211> LENGTH: 571
<212> TYPE: PRT
<213> ORGANISM: Homo sapiens

<400> SEQUENCE: 7

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
                20                  25                  30

Gly Gly Lys Pro Leu Lys Pro Val Pro Gly Gly Leu Ala Gly Ala Gly
            35                  40                  45

Leu Gly Ala Gly Leu Gly Ala Phe Pro Ala Val Thr Phe Pro Gly Ala
        50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
```

-continued

|     |     |     |     |     | 85  |     |     |     |     | 90  |     |     |     |     | 95  |     |
| --- | --- | --- | --- | --- | --- | --- | --- | --- | --- | --- | --- | --- | --- | --- | --- | --- |

Val Ser Ala Gly Ala Val Pro Gln Pro Gly Ala Gly Val Lys Pro
           100                      105                 110

Gly Lys Val Pro Gly Val Gly Leu Pro Gly Val Tyr Pro Gly Gly Val
        115                   120                 125

Leu Pro Gly Ala Arg Phe Pro Gly Val Gly Val Leu Pro Gly Val Pro
130                    135                 140

Thr Gly Ala Gly Val Lys Pro Lys Ala Pro Gly Val Gly Ala Phe
145                  150                 155                 160

Ala Gly Ile Pro Gly Val Gly Pro Phe Gly Pro Gln Pro Gly Val
        165                   170                 175

Pro Leu Gly Tyr Pro Ile Lys Ala Pro Lys Leu Pro Gly Gly Tyr Gly
        180                   185                 190

Leu Pro Tyr Thr Thr Gly Lys Leu Pro Tyr Gly Tyr Gly Pro Gly Gly
        195                   200                 205

Val Ala Gly Ala Ala Gly Lys Ala Gly Tyr Pro Thr Gly Thr Gly Val
210                    215                 220

Gly Pro Gln Ala Ala Ala Ala Ala Ala Lys Ala Ala Ala Lys Phe
225                  230                 235                 240

Gly Ala Gly Ala Ala Gly Val Leu Pro Gly Val Gly Ala Gly Val
        245                   250                 255

Pro Gly Val Pro Gly Ala Ile Pro Gly Ile Gly Ile Ala Gly Val
        260                   265                 270

Gly Thr Pro Ala Ala Ala Ala Ala Ala Ala Ala Lys Ala Ala
        275                   280                 285

Lys Tyr Gly Ala Ala Ala Gly Leu Val Pro Gly Gly Pro Gly Phe Gly
        290                   295                 300

Pro Gly Val Val Gly Val Pro Gly Ala Gly Val Pro Gly Val Gly Val
305                    310                 315                 320

Pro Gly Ala Gly Ile Pro Val Val Pro Gly Ala Gly Ile Pro Gly Ala
        325                   330                 335

Ala Val Pro Gly Val Val Ser Pro Glu Ala Ala Lys Ala Ala Ala
        340                   345                 350

Lys Ala Ala Lys Tyr Gly Ala Arg Pro Gly Val Gly Val Gly Gly Ile
        355                   360                 365

Pro Thr Tyr Gly Val Gly Ala Gly Gly Phe Pro Gly Phe Gly Val Gly
        370                   375                 380

Val Gly Gly Ile Pro Gly Val Ala Gly Val Pro Ser Val Gly Gly Val
385                    390                 395                 400

Pro Gly Val Gly Gly Val Pro Gly Val Gly Ile Ser Pro Glu Ala Gln
                    405                 410                 415

Ala Ala Ala Ala Lys Ala Ala Lys Tyr Gly Val Gly Thr Pro Ala
        420                   425                 430

Ala Ala Ala Lys Ala Ala Lys Ala Ala Gln Phe Gly Leu Val
        435                   440                 445

Pro Gly Val Gly Val Ala Pro Gly Val Gly Val Ala Pro Gly Val Gly
        450                   455                 460

Val Ala Pro Gly Val Gly Leu Ala Pro Gly Val Gly Val Ala Pro Gly
465                    470                 475                 480

Val Gly Val Ala Pro Gly Val Gly Val Ala Pro Gly Ile Gly Pro Gly
                    485                 490                 495

Gly Val Ala Ala Ala Lys Ser Ala Ala Lys Val Ala Ala Lys Ala
        500                   505                 510

```
Gln Leu Arg Ala Ala Gly Leu Gly Ala Gly Ile Pro Gly Leu Gly
        515                 520                 525

Val Gly Val Gly Val Pro Gly Leu Gly Val Gly Ala Gly Val Pro Gly
            530                 535                 540

Leu Gly Val Gly Ala Gly Cys Ser Gly Phe Arg Cys Trp Arg Gly Arg
545                 550                 555                 560

Arg Cys Thr Ser Phe Pro Val Ser Arg Thr Ala
                565                 570

<210> SEQ ID NO 8
<211> LENGTH: 9
<212> TYPE: PRT
<213> ORGANISM: Homo sapiens

<400> SEQUENCE: 8

Lys Ala Pro Gly Val Gly Gly Ala Phe
1               5

<210> SEQ ID NO 9
<211> LENGTH: 7
<212> TYPE: PRT
<213> ORGANISM: Homo sapiens

<400> SEQUENCE: 9

Arg Ala Ala Ala Gly Leu Gly
1               5

<210> SEQ ID NO 10
<211> LENGTH: 11
<212> TYPE: PRT
<213> ORGANISM: Homo sapiens

<400> SEQUENCE: 10

Arg Ser Leu Ser Pro Glu Leu Arg Glu Gly Asp
1               5                   10

<210> SEQ ID NO 11
<211> LENGTH: 9
<212> TYPE: PRT
<213> ORGANISM: Homo sapiens

<400> SEQUENCE: 11

Lys Ala Ala Lys Ala Gly Ala Gly Leu
1               5

<210> SEQ ID NO 12
<211> LENGTH: 9
<212> TYPE: PRT
<213> ORGANISM: Homo sapiens

<400> SEQUENCE: 12

Lys Ala Gly Ala Gly Leu Gly Gly Val
1               5

<210> SEQ ID NO 13
<211> LENGTH: 13
<212> TYPE: PRT
<213> ORGANISM: Homo sapiens

<400> SEQUENCE: 13

Ala Leu Ala Ala Ala Lys Ala Ala Lys Tyr Gly Ala Ala
1               5                   10
```

<210> SEQ ID NO 14
<211> LENGTH: 11
<212> TYPE: PRT
<213> ORGANISM: Homo sapiens

<400> SEQUENCE: 14

Lys Ala Ala Gln Phe Gly Leu Val Pro Gly Val
1               5                   10

<210> SEQ ID NO 15
<211> LENGTH: 11
<212> TYPE: PRT
<213> ORGANISM: Homo sapiens

<400> SEQUENCE: 15

Lys Ser Ala Ala Lys Val Ala Ala Lys Ala Gln
1               5                   10

<210> SEQ ID NO 16
<211> LENGTH: 9
<212> TYPE: PRT
<213> ORGANISM: Homo sapiens

<400> SEQUENCE: 16

Arg Ser Leu Ser Pro Glu Leu Arg Glu
1               5

<210> SEQ ID NO 17
<211> LENGTH: 8
<212> TYPE: PRT
<213> ORGANISM: Homo sapiens

<400> SEQUENCE: 17

Gly Gln Leu Arg Ala Ala Ala Gly
1               5

<210> SEQ ID NO 18
<211> LENGTH: 8
<212> TYPE: PRT
<213> ORGANISM: Homo sapiens

<400> SEQUENCE: 18

Val Gln Leu Arg Ala Ala Ala Gly
1               5

<210> SEQ ID NO 19
<211> LENGTH: 8
<212> TYPE: PRT
<213> ORGANISM: Homo sapiens

<400> SEQUENCE: 19

Ile Gln Leu Arg Ala Ala Ala Gly
1               5

<210> SEQ ID NO 20
<211> LENGTH: 8
<212> TYPE: PRT
<213> ORGANISM: Homo sapiens

<400> SEQUENCE: 20

Leu Gln Leu Arg Ala Ala Ala Gly
1               5

<210> SEQ ID NO 21

```
<211> LENGTH: 8
<212> TYPE: PRT
<213> ORGANISM: Homo sapiens

<400> SEQUENCE: 21

Ala Asn Leu Arg Ala Ala Ala Gly
1               5

<210> SEQ ID NO 22
<211> LENGTH: 8
<212> TYPE: PRT
<213> ORGANISM: Homo sapiens

<400> SEQUENCE: 22

Ala Gly Leu Arg Ala Ala Ala Gly
1               5

<210> SEQ ID NO 23
<211> LENGTH: 8
<212> TYPE: PRT
<213> ORGANISM: Homo sapiens

<400> SEQUENCE: 23

Ala Val Leu Arg Ala Ala Ala Gly
1               5

<210> SEQ ID NO 24
<211> LENGTH: 8
<212> TYPE: PRT
<213> ORGANISM: Homo sapiens

<400> SEQUENCE: 24

Ala Ser Leu Arg Ala Ala Ala Gly
1               5

<210> SEQ ID NO 25
<211> LENGTH: 8
<212> TYPE: PRT
<213> ORGANISM: Homo sapiens

<400> SEQUENCE: 25

Ala Gln Gly Arg Ala Ala Ala Gly
1               5

<210> SEQ ID NO 26
<211> LENGTH: 8
<212> TYPE: PRT
<213> ORGANISM: Homo sapiens

<400> SEQUENCE: 26

Ala Gln Val Arg Ala Ala Ala Gly
1               5

<210> SEQ ID NO 27
<211> LENGTH: 8
<212> TYPE: PRT
<213> ORGANISM: Homo sapiens

<400> SEQUENCE: 27

Ala Gln Ile Arg Ala Ala Ala Gly
1               5

<210> SEQ ID NO 28
<211> LENGTH: 8
<212> TYPE: PRT
```

<213> ORGANISM: Homo sapiens

<400> SEQUENCE: 28

Ala Gln Ala Arg Ala Ala Ala Gly
1               5

<210> SEQ ID NO 29
<211> LENGTH: 8
<212> TYPE: PRT
<213> ORGANISM: Homo sapiens

<400> SEQUENCE: 29

Ala Gln Leu Arg Gly Ala Ala Gly
1               5

<210> SEQ ID NO 30
<211> LENGTH: 8
<212> TYPE: PRT
<213> ORGANISM: Homo sapiens

<400> SEQUENCE: 30

Ala Gln Leu Arg Val Ala Ala Gly
1               5

<210> SEQ ID NO 31
<211> LENGTH: 8
<212> TYPE: PRT
<213> ORGANISM: Homo sapiens

<400> SEQUENCE: 31

Ala Gln Leu Arg Ile Ala Ala Gly
1               5

<210> SEQ ID NO 32
<211> LENGTH: 8
<212> TYPE: PRT
<213> ORGANISM: Homo sapiens

<400> SEQUENCE: 32

Ala Gln Leu Arg Leu Ala Ala Gly
1               5

<210> SEQ ID NO 33
<211> LENGTH: 8
<212> TYPE: PRT
<213> ORGANISM: Homo sapiens

<400> SEQUENCE: 33

Ala Gln Leu Arg Ala Gly Ala Gly
1               5

<210> SEQ ID NO 34
<211> LENGTH: 8
<212> TYPE: PRT
<213> ORGANISM: Homo sapiens

<400> SEQUENCE: 34

Ala Gln Leu Arg Ala Val Ala Gly
1               5

<210> SEQ ID NO 35
<211> LENGTH: 8
<212> TYPE: PRT
<213> ORGANISM: Homo sapiens

```
<400> SEQUENCE: 35

Ala Gln Leu Arg Ala Ile Ala Gly
1               5

<210> SEQ ID NO 36
<211> LENGTH: 8
<212> TYPE: PRT
<213> ORGANISM: Homo sapiens

<400> SEQUENCE: 36

Ala Gln Leu Arg Ala Leu Ala Gly
1               5

<210> SEQ ID NO 37
<211> LENGTH: 8
<212> TYPE: PRT
<213> ORGANISM: Homo sapiens

<400> SEQUENCE: 37

Ala Gln Leu Arg Ala Ala Gly Gly
1               5

<210> SEQ ID NO 38
<211> LENGTH: 8
<212> TYPE: PRT
<213> ORGANISM: Homo sapiens

<400> SEQUENCE: 38

Ala Gln Leu Arg Ala Ala Val Gly
1               5

<210> SEQ ID NO 39
<211> LENGTH: 8
<212> TYPE: PRT
<213> ORGANISM: Homo sapiens

<400> SEQUENCE: 39

Ala Gln Leu Arg Ala Ala Ile Gly
1               5

<210> SEQ ID NO 40
<211> LENGTH: 8
<212> TYPE: PRT
<213> ORGANISM: Homo sapiens

<400> SEQUENCE: 40

Ala Gln Leu Arg Ala Ala Leu Gly
1               5

<210> SEQ ID NO 41
<211> LENGTH: 8
<212> TYPE: PRT
<213> ORGANISM: Homo sapiens

<400> SEQUENCE: 41

Ala Gln Leu Arg Ala Ala Ala Ala
1               5

<210> SEQ ID NO 42
<211> LENGTH: 8
<212> TYPE: PRT
<213> ORGANISM: Homo sapiens

<400> SEQUENCE: 42
```

Ala Gln Leu Arg Ala Ala Ala Ile
1               5

<210> SEQ ID NO 43
<211> LENGTH: 8
<212> TYPE: PRT
<213> ORGANISM: Homo sapiens

<400> SEQUENCE: 43

Ala Gln Leu Arg Ala Ala Ala Val
1               5

<210> SEQ ID NO 44
<211> LENGTH: 8
<212> TYPE: PRT
<213> ORGANISM: Homo sapiens

<400> SEQUENCE: 44

Ala Gln Leu Arg Ala Ala Ala Leu
1               5

<210> SEQ ID NO 45
<211> LENGTH: 8
<212> TYPE: PRT
<213> ORGANISM: Homo sapiens

<400> SEQUENCE: 45

Val Gly Gly Ala Leu Ala Ala Ala
1               5

<210> SEQ ID NO 46
<211> LENGTH: 8
<212> TYPE: PRT
<213> ORGANISM: Homo sapiens

<400> SEQUENCE: 46

Gly Pro Gly Ala Leu Ala Ala Ala
1               5

<210> SEQ ID NO 47
<211> LENGTH: 8
<212> TYPE: PRT
<213> ORGANISM: Homo sapiens

<400> SEQUENCE: 47

Ile Pro Gly Ala Leu Ala Ala Ala
1               5

<210> SEQ ID NO 48
<211> LENGTH: 8
<212> TYPE: PRT
<213> ORGANISM: Homo sapiens

<400> SEQUENCE: 48

Leu Pro Gly Ala Leu Ala Ala Ala
1               5

<210> SEQ ID NO 49
<211> LENGTH: 8
<212> TYPE: PRT
<213> ORGANISM: Homo sapiens

<400> SEQUENCE: 49

Ala Pro Gly Ala Leu Ala Ala Ala
1               5

<210> SEQ ID NO 50
<211> LENGTH: 8
<212> TYPE: PRT
<213> ORGANISM: Homo sapiens

<400> SEQUENCE: 50

Val Pro Gly Ala Leu Ala Ala Ala
1               5

<210> SEQ ID NO 51
<211> LENGTH: 8
<212> TYPE: PRT
<213> ORGANISM: Homo sapiens

<400> SEQUENCE: 51

Val Pro Ile Ala Leu Ala Ala Ala
1               5

<210> SEQ ID NO 52
<211> LENGTH: 8
<212> TYPE: PRT
<213> ORGANISM: Homo sapiens

<400> SEQUENCE: 52

Val Pro Leu Ala Leu Ala Ala Ala
1               5

<210> SEQ ID NO 53
<211> LENGTH: 8
<212> TYPE: PRT
<213> ORGANISM: Homo sapiens

<400> SEQUENCE: 53

Val Pro Val Ala Leu Ala Ala Ala
1               5

<210> SEQ ID NO 54
<211> LENGTH: 8
<212> TYPE: PRT
<213> ORGANISM: Homo sapiens

<400> SEQUENCE: 54

Val Pro Gly Ala Gly Ala Ala Ala
1               5

<210> SEQ ID NO 55
<211> LENGTH: 8
<212> TYPE: PRT
<213> ORGANISM: Homo sapiens

<400> SEQUENCE: 55

Val Pro Gly Ala Ile Ala Ala Ala
1               5

<210> SEQ ID NO 56
<211> LENGTH: 8
<212> TYPE: PRT
<213> ORGANISM: Homo sapiens

<400> SEQUENCE: 56

Val Pro Gly Ala Ala Ala Ala Ala
1               5

<210> SEQ ID NO 57
<211> LENGTH: 8
<212> TYPE: PRT
<213> ORGANISM: Homo sapiens

<400> SEQUENCE: 57

Val Pro Gly Ala Val Ala Ala Ala
1               5

<210> SEQ ID NO 58
<211> LENGTH: 8
<212> TYPE: PRT
<213> ORGANISM: Homo sapiens

<400> SEQUENCE: 58

Val Pro Gly Ala Leu Gly Ala Ala
1               5

<210> SEQ ID NO 59
<211> LENGTH: 8
<212> TYPE: PRT
<213> ORGANISM: Homo sapiens

<400> SEQUENCE: 59

Val Pro Gly Ala Leu Ile Ala Ala
1               5

<210> SEQ ID NO 60
<211> LENGTH: 8
<212> TYPE: PRT
<213> ORGANISM: Homo sapiens

<400> SEQUENCE: 60

Val Pro Gly Ala Leu Leu Ala Ala
1               5

<210> SEQ ID NO 61
<211> LENGTH: 8
<212> TYPE: PRT
<213> ORGANISM: Homo sapiens

<400> SEQUENCE: 61

Val Pro Gly Ala Leu Val Ala Ala
1               5

<210> SEQ ID NO 62
<211> LENGTH: 8
<212> TYPE: PRT
<213> ORGANISM: Homo sapiens

<400> SEQUENCE: 62

Val Pro Gly Ala Leu Ala Gly Ala
1               5

<210> SEQ ID NO 63
<211> LENGTH: 8
<212> TYPE: PRT
<213> ORGANISM: Homo sapiens

<400> SEQUENCE: 63

Val Pro Gly Ala Leu Ala Ile Ala
1               5

<210> SEQ ID NO 64
<211> LENGTH: 8

```
<212> TYPE: PRT
<213> ORGANISM: Homo sapiens

<400> SEQUENCE: 64

Val Pro Gly Ala Leu Ala Leu Ala
1               5

<210> SEQ ID NO 65
<211> LENGTH: 8
<212> TYPE: PRT
<213> ORGANISM: Homo sapiens

<400> SEQUENCE: 65

Val Pro Gly Ala Leu Ala Val Ala
1               5

<210> SEQ ID NO 66
<211> LENGTH: 8
<212> TYPE: PRT
<213> ORGANISM: Homo sapiens

<400> SEQUENCE: 66

Val Pro Gly Ala Leu Ala Ala Ala
1               5

<210> SEQ ID NO 67
<211> LENGTH: 8
<212> TYPE: PRT
<213> ORGANISM: Homo sapiens

<400> SEQUENCE: 67

Val Pro Gly Ala Leu Ala Ala Gly
1               5

<210> SEQ ID NO 68
<211> LENGTH: 8
<212> TYPE: PRT
<213> ORGANISM: Homo sapiens

<400> SEQUENCE: 68

Val Pro Gly Ala Leu Ala Ala Ile
1               5

<210> SEQ ID NO 69
<211> LENGTH: 8
<212> TYPE: PRT
<213> ORGANISM: Homo sapiens

<400> SEQUENCE: 69

Val Pro Gly Ala Leu Ala Ala Leu
1               5

<210> SEQ ID NO 70
<211> LENGTH: 8
<212> TYPE: PRT
<213> ORGANISM: Homo sapiens

<400> SEQUENCE: 70

Val Pro Gly Ala Leu Ala Ala Val
1               5

<210> SEQ ID NO 71
<211> LENGTH: 515
<212> TYPE: PRT
<213> ORGANISM: Homo sapiens
```

<400> SEQUENCE: 71

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
            35                  40                  45

Leu Gly Ala Gly Leu Gly Ala Phe Pro Ala Val Thr Phe Pro Gly Ala
        50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
            85                  90                  95

Val Ser Ala Gly Ala Val Val Pro Gln Pro Gly Ala Gly Val Lys Pro
        100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
        130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
            165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
        210                 215                 220

Gly Pro Gln Ala Ala Ala Ala Ala Ala Lys Ala Ala Ala Lys Phe
225                 230                 235                 240

Gly Ala Gly Ala Ala Gly Val Leu Pro Gly Val Gly Ala Gly Val
            245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Lys Ala Ala
            275                 280                 285

Lys Tyr Gly Ala Ala Gly Leu Val Pro Gly Gly Pro Gly Phe Gly
290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
            325                 330                 335

Ala Val Pro Gly Val Val Ser Pro Glu Ala Ala Lys Ala Ala Ala
            340                 345                 350

Lys Ala Ala Lys Tyr Gly Ala Arg Pro Gly Val Gly Val Gly Gly Ile
            355                 360                 365

Pro Thr Tyr Gly Val Gly Ala Gly Phe Pro Gly Phe Gly Val Gly
            370                 375                 380

Val Gly Gly Ile Pro Gly Val Ala Gly Val Pro Ser Val Gly Gly Val
385                 390                 395                 400

Pro Gly Val Gly Gly Val Pro Gly Val Gly Ile Ser Pro Glu Ala Gln

-continued

```
                405                 410                 415
Ala Ala Ala Ala Lys Ala Ala Lys Tyr Gly Val Gly Thr Pro Ala
            420                 425                 430

Ala Ala Ala Ala Lys Ala Ala Lys Ala Ala Gln Phe Gly Leu Val
        435                 440                 445

Pro Gly Val Gly Val Ala Pro Gly Val Gly Val Ala Pro Gly Val Gly
    450                 455                 460

Val Ala Pro Gly Val Gly Leu Ala Pro Gly Val Gly Val Ala Pro Gly
465                 470                 475                 480

Val Gly Val Ala Pro Gly Val Gly Val Ala Pro Gly Ile Gly Pro Gly
            485                 490                 495

Gly Val Ala Ala Ala Lys Ser Ala Ala Lys Val Ala Ala Lys Ala
            500                 505                 510

Gln Leu Arg
        515

<210> SEQ ID NO 72
<211> LENGTH: 49
<212> TYPE: PRT
<213> ORGANISM: Homo sapiens

<400> SEQUENCE: 72

Ala Ala Ala Gly Leu Gly Ala Gly Ile Pro Gly Leu Gly Val Gly Val
1               5                   10                  15

Gly Val Pro Gly Leu Gly Val Gly Ala Gly Val Pro Gly Leu Gly Val
            20                  25                  30

Gly Ala Gly Val Pro Gly Phe Gly Ala Gly Ala Asp Glu Gly Val Arg
        35                  40                  45

Arg

<210> SEQ ID NO 73
<211> LENGTH: 171
<212> TYPE: PRT
<213> ORGANISM: Homo sapiens

<400> SEQUENCE: 73

Gly Val Arg Arg Ser Leu Ser Pro Glu Leu Arg Glu Gly Asp Pro Ser
1               5                   10                  15

Ser Ser Gln His Leu Pro Ser Thr Pro Ser Ser Pro Arg Val Pro Gly
            20                  25                  30

Ala Leu Ala Ala Ala Lys Ala Ala Lys Tyr Gly Ala Ala Val Pro Gly
        35                  40                  45

Val Leu Gly Gly Leu Gly Ala Leu Gly Val Gly Ile Pro Gly Gly
    50                  55                  60

Val Val Gly Ala Gly Pro Ala Ala Ala Ala Ala Lys Ala Ala
65                  70                  75                  80

Ala Lys Ala Ala Gln Phe Gly Leu Val Ala Ala Gly Leu Gly Gly
            85                  90                  95

Leu Gly Val Gly Gly Leu Gly Val Pro Gly Val Gly Gly Leu Gly Gly
        100                 105                 110

Ile Pro Pro Ala Ala Ala Lys Ala Ala Lys Tyr Gly Ala Ala Gly
            115                 120                 125

Leu Gly Gly Val Leu Gly Gly Ala Gly Gln Phe Pro Leu Gly Gly Val
        130                 135                 140

Ala Ala Arg Pro Gly Phe Gly Leu Ser Pro Ile Phe Pro Gly Gly Ala
145                 150                 155                 160
```

```
Cys Leu Gly Lys Ala Cys Gly Arg Lys Arg Lys
            165                 170
```

<210> SEQ ID NO 74
<211> LENGTH: 183
<212> TYPE: PRT
<213> ORGANISM: Homo sapiens

<400> SEQUENCE: 74

```
Ala Ala Ala Gly Leu Gly Ala Gly Ile Pro Gly Leu Gly Val Gly Val
1               5                   10                  15

Gly Val Pro Gly Leu Gly Val Gly Ala Gly Val Pro Gly Leu Gly Val
                20                  25                  30

Gly Ala Gly Val Pro Gly Phe Gly Ala Val Pro Gly Ala Leu Ala Ala
                35                  40                  45

Ala Lys Ala Ala Lys Tyr Gly Ala Ala Val Pro Gly Val Leu Gly Gly
        50                  55                  60

Leu Gly Ala Leu Gly Gly Val Gly Ile Pro Gly Val Val Gly Ala
65                  70                  75                  80

Gly Pro Ala Ala Ala Ala Ala Ala Lys Ala Ala Lys Ala Ala
                85                  90                  95

Gln Phe Gly Leu Val Gly Ala Ala Gly Leu Gly Gly Leu Gly Val Gly
            100                 105                 110

Gly Leu Gly Val Pro Gly Val Gly Gly Leu Gly Ile Pro Pro Ala
            115                 120                 125

Ala Ala Ala Lys Ala Ala Lys Tyr Gly Ala Ala Gly Leu Gly Gly Val
        130                 135                 140

Leu Gly Gly Ala Gly Gln Phe Pro Leu Gly Gly Val Ala Ala Arg Pro
145                 150                 155                 160

Gly Phe Gly Leu Ser Pro Ile Phe Pro Gly Gly Ala Cys Leu Gly Lys
                165                 170                 175

Ala Cys Gly Arg Lys Arg Lys
                180
```

<210> SEQ ID NO 75
<211> LENGTH: 18
<212> TYPE: PRT
<213> ORGANISM: bovine tropoelastin

<400> SEQUENCE: 75

```
Val Pro Thr Gly Ala Gly Val Lys Pro Lys Ala Pro Gly Gly Gly Gly
1               5                   10                  15

Ala Phe
```

<210> SEQ ID NO 76
<211> LENGTH: 17
<212> TYPE: PRT
<213> ORGANISM: mouse tropoelastin

<400> SEQUENCE: 76

```
Val Pro Thr Gly Thr Gly Val Lys Ala Lys Ala Pro Gly Gly Gly Ala
1               5                   10                  15

Phe
```

<210> SEQ ID NO 77
<211> LENGTH: 18
<212> TYPE: PRT
<213> ORGANISM: bovine elastin

```
<400> SEQUENCE: 77

Val Pro Thr Gly Ala Gly Val Lys Pro Lys Ala Gln Val Gly Ala Gly
1               5                   10                  15

Ala Phe

<210> SEQ ID NO 78
<211> LENGTH: 16
<212> TYPE: PRT
<213> ORGANISM: rat tropoelastin

<400> SEQUENCE: 78

Val Pro Thr Gly Thr Gly Val Lys Ala Lys Val Pro Gly Gly Gly Gly
1               5                   10                  15

<210> SEQ ID NO 79
<211> LENGTH: 15
<212> TYPE: PRT
<213> ORGANISM: chicken tropoelastin

<400> SEQUENCE: 79

Val Pro Thr Gly Thr Gly Ile Lys Ala Lys Gly Pro Gly Ala Gly
1               5                   10                  15

<210> SEQ ID NO 80
<211> LENGTH: 17
<212> TYPE: PRT
<213> ORGANISM: mouse tropoelastin

<400> SEQUENCE: 80

Lys Ala Ala Ala Lys Ala Gln Tyr Arg Ala Ala Ala Gly Leu Gly Ala
1               5                   10                  15

Gly

<210> SEQ ID NO 81
<211> LENGTH: 17
<212> TYPE: PRT
<213> ORGANISM: bovine elastin

<400> SEQUENCE: 81

Lys Ala Ala Ala Lys Ala Gln Phe Arg Ala Ala Ala Gly Leu Pro Ala
1               5                   10                  15

Gly

<210> SEQ ID NO 82
<211> LENGTH: 20
<212> TYPE: PRT
<213> ORGANISM: Artificial
<220> FEATURE:
<223> OTHER INFORMATION: tropoelastin consensus sequence
<220> FEATURE:
<221> NAME/KEY: MISC_FEATURE
<222> LOCATION: (9)..(9)
<223> OTHER INFORMATION: IS AN AROMATIC OR HYDROPHOBIC RESIDUE
<220> FEATURE:
<221> NAME/KEY: MISC_FEATURE
<222> LOCATION: (16)..(16)
<223> OTHER INFORMATION: can be either Pro or Gly
<220> FEATURE:
<221> NAME/KEY: MISC_FEATURE
<222> LOCATION: (19)..(19)
<223> OTHER INFORMATION: is a hydrophobic residue

<400> SEQUENCE: 82

Ala Lys Ala Ala Ala Lys Ala Gln Xaa Arg Ala Ala Ala Gly Leu Xaa
```

-continued

```
                1               5                  10                 15
Ala Gly Xaa Pro
         20

<210> SEQ ID NO 83
<211> LENGTH: 14
<212> TYPE: PRT
<213> ORGANISM: Homo sapiens
<220> FEATURE:
<221> NAME/KEY: VARIANT
<222> LOCATION: (7)..(8)
<223> OTHER INFORMATION: there is a reduced peptide bond between Arg and
      Ala

<400> SEQUENCE: 83

Ala Ala Lys Ala Gln Leu Arg Ala Ala Ala Gly Leu Gly Ala
1               5                   10

<210> SEQ ID NO 84
<211> LENGTH: 14
<212> TYPE: PRT
<213> ORGANISM: Homo sapiens
<220> FEATURE:
<221> NAME/KEY: VARIANT
<222> LOCATION: (7)..(8)
<223> OTHER INFORMATION: there is a reduced peptide bond between Ala and
      Arg

<400> SEQUENCE: 84

Ala Gly Leu Gly Ala Ala Ala Arg Leu Gln Ala Lys Ala Ala
1               5                   10

<210> SEQ ID NO 85
<211> LENGTH: 14
<212> TYPE: PRT
<213> ORGANISM: Homo sapiens

<400> SEQUENCE: 85

Ala Gly Leu Gly Ala Ala Ala Arg Leu Gln Ala Lys Ala Ala
1               5                   10

<210> SEQ ID NO 86
<211> LENGTH: 8
<212> TYPE: PRT
<213> ORGANISM: Homo sapiens
<220> FEATURE:
<221> NAME/KEY: VARIANT
<222> LOCATION: (4)..(5)
<223> OTHER INFORMATION: there is a reduced peptide bond between Ala and
      Leu

<400> SEQUENCE: 86

Val Pro Gly Ala Leu Ala Ala Ala
1               5

<210> SEQ ID NO 87
<211> LENGTH: 8
<212> TYPE: PRT
<213> ORGANISM: Homo sapiens
<220> FEATURE:
<221> NAME/KEY: VARIANT
<222> LOCATION: (4)..(5)
<223> OTHER INFORMATION: there is a reduced peptide bond between Leu and
      Ala

<400> SEQUENCE: 87

Ala Ala Ala Leu Ala Gly Pro Val
1               5
```

<210> SEQ ID NO 88
<211> LENGTH: 8
<212> TYPE: PRT
<213> ORGANISM: Homo sapiens

<400> SEQUENCE: 88

Ala Ala Ala Leu Ala Gly Pro Val
1               5

<210> SEQ ID NO 89
<211> LENGTH: 30
<212> TYPE: DNA
<213> ORGANISM: Artificial
<220> FEATURE:
<223> OTHER INFORMATION: mutagenic primer

<400> SEQUENCE: 89
cgggtttcgg tgctgttccg ggcgcgctgg                                      30

<210> SEQ ID NO 90
<211> LENGTH: 20
<212> TYPE: DNA
<213> ORGANISM: Artificial
<220> FEATURE:
<223> OTHER INFORMATION: primer

<400> SEQUENCE: 90
gggtgttggc gttgcaccag                                                 20

<210> SEQ ID NO 91
<211> LENGTH: 20
<212> TYPE: DNA
<213> ORGANISM: Artificial
<220> FEATURE:
<223> OTHER INFORMATION: primer

<400> SEQUENCE: 91
tgcacctaca acaccgcccg                                                 20

<210> SEQ ID NO 92
<211> LENGTH: 20
<212> TYPE: DNA
<213> ORGANISM: Artificial
<220> FEATURE:
<223> OTHER INFORMATION: primer

<400> SEQUENCE: 92
tgcctttgcc ggtttgtacg                                                 20

<210> SEQ ID NO 93
<211> LENGTH: 20
<212> TYPE: DNA
<213> ORGANISM: Artificial
<220> FEATURE:
<223> OTHER INFORMATION: primer

<400> SEQUENCE: 93
tccaggtggc tacggtctgc                                                 20

<210> SEQ ID NO 94
<211> LENGTH: 21
<212> TYPE: DNA
<213> ORGANISM: Artificial
<220> FEATURE:
<223> OTHER INFORMATION: primer

```
<400> SEQUENCE: 94
gagtacctac gcctgcgata c                                              21

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95
ggagtaccaa cgccgtactt                                                20

<210> SEQ ID NO 96
<211> LENGTH: 20
<212> TYPE: DNA
<213> ORGANISM: Artificial
<220> FEATURE:
<223> OTHER INFORMATION: primer

<400> SEQUENCE: 96
gggtgttggc gttgcaccag                                                20

<210> SEQ ID NO 97
<211> LENGTH: 20
<212> TYPE: DNA
<213> ORGANISM: Artificial
<220> FEATURE:
<223> OTHER INFORMATION: primer

<400> SEQUENCE: 97
tgcacctaca acaccgcccg                                                20

<210> SEQ ID NO 98
<211> LENGTH: 20
<212> TYPE: DNA
<213> ORGANISM: Artificial
<220> FEATURE:
<223> OTHER INFORMATION: primer

<400> SEQUENCE: 98
gcactcacta tagggagacc                                                20

<210> SEQ ID NO 99
<211> LENGTH: 20
<212> TYPE: DNA
<213> ORGANISM: Artificial
<220> FEATURE:
<223> OTHER INFORMATION: primer

<400> SEQUENCE: 99
gccaactcag cttcctttcg                                                20

<210> SEQ ID NO 100
<211> LENGTH: 20
<212> TYPE: DNA
<213> ORGANISM: Artificial
<220> FEATURE:
<223> OTHER INFORMATION: primer

<400> SEQUENCE: 100
taatacgact cactataggg                                                20

<210> SEQ ID NO 101
```

```
<211> LENGTH: 15
<212> TYPE: PRT
<213> ORGANISM: Homo sapiens

<400> SEQUENCE: 101

Val Val Gly Ser Pro Ser Ala Gln Asp Glu Ala Ser Pro Leu Ser
1               5                   10                  15

<210> SEQ ID NO 102
<211> LENGTH: 10
<212> TYPE: PRT
<213> ORGANISM: Homo sapiens

<400> SEQUENCE: 102

Lys Ala Ala Lys Ala Gly Ala Gly Leu
1               5                   10

<210> SEQ ID NO 103
<211> LENGTH: 12
<212> TYPE: PRT
<213> ORGANISM: Homo sapiens

<400> SEQUENCE: 103

Ala Leu Ala Ala Lys Ala Ala Lys Tyr Gly Ala Ala
1               5                   10

<210> SEQ ID NO 104
<211> LENGTH: 11
<212> TYPE: PRT
<213> ORGANISM: Homo sapiens

<400> SEQUENCE: 104

Lys Ala Ala Gln Phe Gly Leu Val Pro Gly Val
1               5                   10

<210> SEQ ID NO 105
<211> LENGTH: 18
<212> TYPE: PRT
<213> ORGANISM: Homo sapiens

<400> SEQUENCE: 105

Gly Gly Val Pro Gly Ala Ile Pro Gly Gly Val Pro Gly Gly Phe Tyr
1               5                   10                  15

Pro Gly

<210> SEQ ID NO 106
<211> LENGTH: 5
<212> TYPE: PRT
<213> ORGANISM: Homo sapiens

<400> SEQUENCE: 106

Arg Ala Ala Ala Gly
1               5
```

The invention claimed is:

1. A method of reducing the susceptibility of tropoelastin to proteolysis by thrombin, kallikrein or serum, comprising mutating one or more of the amino acid residues of the amino acid sequence corresponding to SEQ ID NO: 106 (RAAAG) in the tropoelastin, so that susceptibility of the tropoelastin to cleavage by thrombin, kallikrein or serum is reduced.

2. The method of claim 1, wherein before the mutation the tropoelastin has the amino acid sequence of SEQ ID NO: 4 or 5.

3. The method of claim 2, wherein the amino acid sequence corresponding to SEQ ID NO: 106 (RAAAG) is the amino acid sequence at position 515 to position 519 of SEQ ID NO: 4 or 5.

4. The method according to claim 1 wherein one amino acid residue in the amino acid sequence corresponding to SEQ ID NO: 106 (RAAAG) is mutated.

5. The method according to claim 1, wherein the arginine residue of the amino acid sequence corresponding to SEQ ID NO: 106 (RAAAG) is mutated.

6. The method of claim 1, wherein the arginine residue of the amino acid sequence corresponding to SEQ ID NO: 106 (RAAAG) is replaced with an alanine residue.

7. The method of claim 1, wherein the arginine residue of the amino acid sequence corresponding to SEQ ID NO: 106 (RAAAG) is replaced with a leucine residue.

8. The method of claim 1, further comprising mutating one or more of the amino acid residues of the amino acid sequence corresponding to SEQ ID NO: 8 of SEQ ID NO: 4 or 5, to thereby further reduce the susceptibility of the tropoelastin to cleavage by thrombin.

9. The method of claim 1, wherein before the mutation the tropoelastin has the amino acid sequence of SEQ ID NO: 4, and further comprising mutating one or more of the amino acid residues of the amino acid sequence corresponding to SEQ ID NO: 10 of SEQ ID NO: 4, to thereby further reduce the susceptibility of the tropoelastin to cleavage by kallikrein.

10. The method of claim 1, further comprising mutating one or more of the amino acid residues of the amino acid sequence corresponding to SEQ ID NO: 14 of SEQ ID NO: 4 or 5, to thereby further reduce the susceptibility of the tropoelastin to cleavage by serum.

11. The method of claim 1, wherein before the mutation the tropoelastin has the amino acid sequence of SEQ ID NO: 4, and further comprising mutating one or more of the amino acid residues of the amino acid sequence corresponding to SEQ ID NO: 15 or 16 of SEQ ID NO: 4, to thereby further reduce the susceptibility of the tropoelastin to cleavage by serum.

12. The method of claim 1, further comprising mutating one or more of the amino acid residues of the amino acid sequence corresponding to SEQ ID NO: 11 or 12 of SEQ ID NO: 4 or 5, to thereby reduce the susceptibility of the tropoelastin to cleavage by plasmin.

13. The method of claim 1, wherein before the mutation the tropoelastin has the amino acid sequence of SEQ ID NO: 4, and further comprising mutating one or more of the amino acid residues of the amino acid sequence corresponding to SEQ ID NO: 13 of SEQ ID NO: 4, to thereby reduce the susceptibility of the tropoelastin to cleavage by gelatinase B.

14. An isolated tropoelastin molecule produced by the method of claim 1.

15. A method of reducing the susceptibility of tropoelastin to thrombin cleavage comprising replacing the alanine at any one of residues 516, 517 or 518 of SEQ ID NO:4 with another amino acid.

16. A method according to claim 15, wherein the alanine corresponding to residue 516 of SEQ ID NO:4 is replaced with another amino acid.

17. A method of reducing the susceptibility of tropoelastin to cleavage by thrombin, kallikrein or serum, wherein the arginine residue corresponding to 515 of SEQ ID NO:4 is replaced with alanine.

18. A method of reducing the susceptibility of tropoelastin to proteolysis by thrombin, kallikrein or serum, consisting of mutating one or more of the amino acid residues corresponding to position 515 to 521 of SEQ ID NO: 4 in the tropoelastin, so that susceptibility of the tropoelastin to cleavage by thrombin, kallikrein or serum is reduced.

19. The method of claim 18, wherein the amino acid residue at position 515 is arginine and is mutated.

20. The method of claim 18, wherein the amino acid residue at position 515 is arginine and is replaced with alanine or leucine.

21. A method of reducing the susceptibility of tropoelastin to proteolysis by thrombin, kallikrein or serum protease, consisting of mutating arginine of the amino acid sequence corresponding to position 515 to 521 of SEQ ID NO: 4, so that susceptibility of the tropoelastin to cleavage by thrombin, kallikrein or serum is reduced.

22. The method of claim 21, wherein the R in the amino acid sequence is replaced with A or L.

23. The method according to claim 21 wherein the tropoelastin is human tropoelastin.

* * * * *